(12) United States Patent
Brodie et al.

(10) Patent No.: US 10,034,902 B2
(45) Date of Patent: Jul. 31, 2018

(54) MICRORNAS FOR THE GENERATION OF ASTROCYTES

(71) Applicants: BrainStem Biotec Ltd., Tel-Aviv (IL); Henry Ford Health System, Detroit, MI (US)

(72) Inventors: Chaya Brodie, Southfield, MI (US); Shimon Slavin, Tel-Aviv (IL)

(73) Assignees: EXOSTEM BIOTEC LTD., Tel-Aviv (IL); HENRY FORD HEALTH SYSTEM, Detroit, MI (US)

( * ) Notice: Subject to any disclaimer, the term of this patent is extended or adjusted under 35 U.S.C. 154(b) by 0 days.

(21) Appl. No.: 14/380,155

(22) PCT Filed: Feb. 21, 2013

(86) PCT No.: PCT/IB2013/051430
§ 371 (c)(1),
(2) Date: Aug. 21, 2014

(87) PCT Pub. No.: WO2013/124817
PCT Pub. Date: Aug. 29, 2013

(65) Prior Publication Data
US 2015/0037298 A1 Feb. 5, 2015

Related U.S. Application Data

(60) Provisional application No. 61/601,624, filed on Feb. 22, 2012.

(51) Int. Cl.
*A61K 35/30* (2015.01)
*C12N 5/079* (2010.01)
*A61K 35/28* (2015.01)
*A61K 35/50* (2015.01)
*A61K 35/51* (2015.01)
*C12Q 1/6876* (2018.01)
*C12N 15/113* (2010.01)

(52) U.S. Cl.
CPC ............. *A61K 35/30* (2013.01); *A61K 35/28* (2013.01); *A61K 35/50* (2013.01); *A61K 35/51* (2013.01); *C12N 5/0622* (2013.01); *C12Q 1/6876* (2013.01); *C12N 15/113* (2013.01); *C12N 2310/141* (2013.01); *C12N 2320/11* (2013.01); *C12N 2330/10* (2013.01); *C12N 2501/01* (2013.01); *C12N 2501/11* (2013.01); *C12N 2501/115* (2013.01); *C12N 2501/135* (2013.01); *C12N 2501/195* (2013.01); *C12N 2501/41* (2013.01); *C12N 2501/65* (2013.01); *C12N 2502/13* (2013.01); *C12N 2502/1305* (2013.01); *C12N 2502/137* (2013.01); *C12N 2502/1311* (2013.01); *C12N 2502/1317* (2013.01); *C12N 2502/1323* (2013.01); *C12N 2502/1329* (2013.01); *C12N 2502/1335* (2013.01); *C12N 2502/1341* (2013.01); *C12N 2502/1347* (2013.01); *C12N 2502/1352* (2013.01); *C12N 2502/1358* (2013.01); *C12N 2502/1364* (2013.01); *C12N 2502/1376* (2013.01); *C12N 2502/1382* (2013.01); *C12N 2502/1388* (2013.01); *C12N 2502/1394* (2013.01); *C12N 2506/025* (2013.01); *C12N 2506/1353* (2013.01); *C12N 2506/1369* (2013.01); *C12N 2506/1384* (2013.01); *C12N 2506/1392* (2013.01); *C12N 2510/00* (2013.01); *C12Q 2600/178* (2013.01)

(58) Field of Classification Search
None
See application file for complete search history.

(56) References Cited

U.S. PATENT DOCUMENTS

| 7,452,677 | B2* | 11/2008 | Lundgren-Åkerlund ................... C07K 16/2839 435/326 |
| 9,803,175 | B2* | 10/2017 | Brodie ................ C12N 5/0623 |
| 2008/0171715 | A1 | 7/2008 | Brown et al. |
| 2008/0176328 | A1 | 7/2008 | Chang et al. |
| 2008/0206256 | A1 | 8/2008 | Spong et al. |
| 2008/0241115 | A1 | 10/2008 | Suh et al. |
| 2009/0010895 | A1 | 1/2009 | Offen et al. |
| 2010/0003751 | A1 | 1/2010 | Revel et al. |

(Continued)

FOREIGN PATENT DOCUMENTS

| EP | 1506997 | 2/2005 |
| EP | 1705245 | 9/2006 |

(Continued)

OTHER PUBLICATIONS

Roush et al Review The let-7 family of microRNAs Trends in Cell Biology vol. 18, Issue 10, Oct. 2008, pp. 505-516.*

(Continued)

*Primary Examiner* — Maria G Leavitt
(74) *Attorney, Agent, or Firm* — The Roy Gross Law Firm, LLC; Roy Gross

(57) ABSTRACT

A method of generating a population of cells useful for treating a nerve disease or disorder in a subject, the method comprising up-regulating a level of at least one exogenous miRNA in mesenchymal stem cells (MSCs) and/or down-regulating a level of at least one miRNA using a polynucleotide agent that hybridizes to the miRNA, thereby generating the population of cells useful for treating the nerve disease or disorder. Isolated populations of cells with an astrocytic phenotype generated thereby and uses thereof are also provided.

9 Claims, 10 Drawing Sheets
(10 of 10 Drawing Sheet(s) Filed in Color)

(56) References Cited

U.S. PATENT DOCUMENTS

| | | |
|---|---|---|
| 2010/0021434 A1 | 1/2010 | Melamed et al. |
| 2010/0150947 A1 | 6/2010 | Siemionow |
| 2011/0311984 A1 | 12/2011 | Paek et al. |
| 2013/0149288 A1 | 6/2013 | Slavin et al. |
| 2015/0024966 A1 | 1/2015 | Brodie et al. |
| 2015/0037299 A1 | 2/2015 | Brodie et al. |

FOREIGN PATENT DOCUMENTS

| | | |
|---|---|---|
| WO | WO 2006/134602 | 12/2006 |
| WO | WO 2009/023525 | 2/2009 |
| WO | WO 2009/122413 | 10/2009 |
| WO | WO 2009/144718 | 12/2009 |
| WO | WO 2010/111522 | 9/2010 |
| WO | WO 2010/144698 | 12/2010 |
| WO | WO 2010144698 | * 12/2010 |
| WO | WO 2011/030336 | 3/2011 |
| WO | WO 2011/159075 | 12/2011 |
| WO | WO 2012/023132 | 2/2012 |
| WO | WO 2013/124815 | 8/2013 |
| WO | WO 2013/124816 | 8/2013 |
| WO | WO 2013/124817 | 8/2013 |

OTHER PUBLICATIONS

Krichevsky Specific MicroRNAs Modulate Embryonic Stem Cell-Derived Neurogenesis Stem Cells. Apr. 2006; 24(4): 857-864.*
DataSheet GeneChip® miRNA 4.0 Array Affymetrix® miRNA 4.1 Array Strip (Affymetrix, Santa Clara, CA, USA) downloaded Nov. 6, 2015.*
Yuan et al 2009 Transfer of MicroRNAs by Embryonic Stem Cell Microvesicles PLoS ONE e4722-e4722.*
Brodie et al 2015 Mesenchymal stem cells and their secreted exosomes deliver exogenous mirnas and sirnas to neural cells: Therapeuticimpact in mouse and in vitro models of als Neurodegenerative Diseases, (Mar. 2015) vol. 15, Supp. Suppl. 1, pp. 1961. Abstract No. ADPD5-2086.Meeting Info: 12th International Conference Alzheimer's an Abstract.*
Lee et al., Mesenchymal Stem Cells Deliver Exogenous miRNAs to Neural Cells and Induce Their Differentiation and Glutamate Transporter Expression Stem Cells and Development vol. 23, No. 23, 2014 pp. 2851-2861.*
Silber et al., miR-124 and miR-137 inhibit proliferation of glioblastoma multiforme cells and induce differentiation of brain tumor stem cells BMC Medicine 2008,pp. 1-17.*
Communication Pursuant to Article 94(3) EPC dated Mar. 3, 2015 From the European Patent Office Re. Application No. 11817858.1.
Restriction Official Action dated May 13, 2015 From the US Patent and Trademark Office Re. U.S. Appl. No. 14/380,165.
Restriction Official Action dated Jul. 31, 2015 From the US Patent and Trademark Office Re. U.S. Appl. No. 14/380,174.
Communication Pursuant to Rule 70(2) and 70a(2) EPC dated Jan. 9, 2014 From the European Patent Office Re. Application No. 11817858.1.
Communication Relating to the Results of the Partial International Search dated Aug. 12, 2013 From the International Searching Authority Re. Application No. PCT/IB2013/051430.
Communication Relating to the Results of the Partial International Search dated Aug. 14, 2013 From the International Searching Authority Re. Application No. PCT/IB2013/051429.
International Preliminary Report on Patentability dated Sep. 4, 2014 From the International Bureau of WIPO Re. Application No. PCT/IB2013/051428.
International Preliminary Report on Patentability dated Sep. 4, 2014 From the International Bureau of WIPO Re. Application No. PCT/IB2013/051429.
International Preliminary Report on Patentability dated Sep. 4, 2014 From the International Bureau of WIPO Re. Application No. PCT/IB2013/051430.
International Preliminary Report on Patentability dated Feb. 28, 2013 From the International Bureau of WIPO Re. Application No. PCT/IL2011/000660.
International Search Report and the Written Opinion dated Oct. 10, 2013 From the International Searching Authority Re. Application No. PCT/IB2013/051429.
International Search Report and the Written Opinion dated Oct. 10, 2013 From the International Searching Authority Re. Application No. PCT/IB2013/051430.
International Search Report and the Written Opinion dated Aug. 21, 2013 From the International Searching Authority Re. Application No. PCT/IB2013/051428.
International Search Report and the Written Opinion dated Dec. 28, 2011 From the International Searching Authority Re. Application No. PCT/IL2011/000660.
Official Action dated Mar. 12, 2015 From the US Patent and Trademark Office Re. U.S. Appl. No. 13/817,535.
Official Action dated May 12, 2014 From the US Patent and Trademark Office Re. U.S. Appl. No. 13/817,535.
Official Action dated Jul. 22, 2013 From the US Patent and Trademark Office Re. U.S. Appl. No. 13/817,535.
Restriction Official Action dated May 6, 2013 From the US Patent and Trademark Office Re. U.S. Appl. No. 13/817,535.
Search Report and Written Opinion dated Dec. 13, 2013 From the Intellectual Property Office of Singapore Issued by the Danish Patent and Trademark Office Re. Application No. 201301101-0.
Supplementary European Search Report and the European Search Opinion dated Dec. 17, 2013 From the European Patent Office Re. Application No. 11817858.1.
Akerblom et al. "Functional Studies of MicroRNAs in Neural Stem Cells: Problems and Perspectives", Frontiers in Neuroscience, XP055074176, 6(Art.14): 1-10, Feb. 2012.
Gao "Context-Dependent Functions of Specific MicroRNAs in Neuronal Development", Neuronal Development, XP021081673, 5(25): 1-9, Oct. 2010.
Gong et al. "Immortalized Mesenchymal Stem Cells: An Alternative to Primary Mesenchymal Stem Cells in Neuronal Differentiation and Neurogeneration Associated Studies", Journal of Biomedical Science, XP021111456, 18(87): 1-16, Nov. 25, 2011.
Kang et al. "Kaposi's Sarcoma-Associated Herpesvirus ORF57 Promotes Escape of Viarl and Human Interleukin-6 From MicroRNA-Mediated Suppression", Journal of Virology, XP055073965, 85(6): 2620-2630, Mar. 2011.
Karaoz et al. "Human Dental Pulp Stem Cells Demonstrate Better Neural and Epithelial Stem Cell Properties Than Bone Marrow-Derived Mesenchymal Stem Cells", Histochemistry and Cell Biology, XP055074788, 136(4): 455-473, Oct. 31, 2011.
Katsushima et al. "Contribution of MicroRNA-1275 to Claudin 11 Protein Suppression Via a Polycomb-Mediated Silencing Mechanism in Human Glioma Stem-Like Cells", The Journal of Biological Chemistry, XP055074166, 287(33): 27396-27406, Aug. 10, 2012.
Kim et al. "A Development Taxonomy of Gliobastoma Defined and Maintained by MicroRNAs", Cancer Research, XP055073956, 71(9): 3387-3399, May 2011.
Kosztowski et al. "Applications of Neural and Mesenchymal Stem Cells in the Treatment of Gliomas", Expert Review of Anticancer Therapy, 9(5): 597-612, May 2009.
Lakshmipathy et al. "Concise Review: MicroRNA Expression in Multipotent Mesenchymal Stromal Cells", Stem Cells, 26: 356-363, 2008. p. 356, Abstract, p. 357, Left Col., Para 5, p. 358, Right Col., Table 2, Para 2, p. 359, Left Col., Para 4, Right Col., Last Para, p. 360, Right Col., Para 2.
Letzen et al. "MicroRNA Expression Profiling of Oligodendrocyte Differentiation From Human Embryonic Stem Cells", PLoS ONE, XP055091734, 5(5): e-10480-1-e10480-12, May 2010. p. 2, col. 2, Para 2, Fig.2, Table 1.
Liu et al. "Induction of Oligodendrocyte Differentiation by Olig2 and Sox10: Evidence for Reciprocal Interactions and Dosage-Dependent Mechanisms", Developmental Biology, 302: 683-693, 2007.
Liu et al. "MicroRNAs Regulation Modulated Self-Renewal and Lineage Differentiation of Stem Cells", Cell Transplantation, XP002605501, 18(9): 1039-1045, Jan. 2009.

(56) References Cited

OTHER PUBLICATIONS

Luo et al. "Connective Tissue Growth Factor (CTGF) Is Regulated by Wnt and Bone Morphogenetic Proteins Signaling in Osteoblast Differentiation of Mesenchymal Stem Cells", The Journal of Biological Chemistry, 279(53): 55958-55968, Dec. 31, 2004. p. 55958, Abstract, p. 55967, Fig.7.

Maisel et al. "Genome-Wide Expression Profiling and Functional Network Analysis Upon Neuroectodermal Conversion of Human Mesenchymal Stem Cells Suggest HIF-1 and MiR-124a as Important Regulators", Experimental Cell Research, XP055074156, 316(17): 2760-2778, Oct. 2010.

Nakamizo et al. "Human Bone Marrow-Derived Mesenchymal Stem Cells in the Treatment of Gliomas", Cancer Research, 65(8): 3307-3318, Apr. 15, 2005.

Ozata et al. "The Role of MicroRNA Deregulation in the Pathogenesis of Adrenocortical Carcinoma", Endocrine-Related Cancer, XP055074162, 18(6): 643-655, Oct. 27, 2011.

Phillips et al. "Genetic Modification of Stem Cells for Transplantation", Advanced Drug Delivery Reviews, 60(2): 160-172, Jan. 14, 2008.

Riggi et al. "EWS-FLI-1 Modulates MiRNA145 and SOX2 Expression to Initiate Mesenchymal Stem Cell Reprogramming Toward Ewing Sarcoma Cancer Stem Cells", Genes & Development, 24: 916-932, 2010.

Sasportas et al. "Assessment of Therapeutic Efficacy and Fated of Engineered Human Mesenchymal Stem Cells for Cancer Therapy", Proc. Natl. Acad. Sci. USA, PNAS, 106(12): 4322-4327, Mar. 24, 2009.

Shookhoff et al. "The Emerging Role of MicroRNAs in Adult Stem Cells", Adult Stem Cells: Biology and Methods of Analysis, XP008163996, Chap.3: 57-97, 2011.

Silber et al. "MiR-124 and MiR-137 Inhibit Proliferation of Glioblastoma Multiforme Cells and Induce Differentiation of Brain Tumor Stem Cells", BMC Medicine, 6(14): 1-17, Jun. 24, 2008.

Song et al. "Connective Tissue Growth Factor (CTGF) Acts as a Downstream Mediator of TGF-Beta1 to Induce Mesenchymal Cell Condensation", Journal of Cellular Physiology, 210: 398-410, 2007. p. 398, Abstract, p. 399, Left Col. Para 2, p. 402, Fig.2, p. 405, Right Col., Para 1.

Xin et al. "Exosome-Mediated Transfer of MiR-133b From Multipotent Mesenchymal Stromal Cells to Neural Cells Contributes to Neurite Outgrowth", Stem Cells, XP055073957, 30(7): 1556-1564, Jul. 18, 2012.

Zhang et al. "Isolation and Characterization of Mesenchymal Stem Cells Derived From Bone Marrow Patients With Parkinson's Disease", In Vitro Cellular & Developmental Biology—Animal, XP055074787, 44(5-6): 169-177, Jun. 2008.

Zhao et al. "MicroRNA-Mediated Control of Oligodendrocyte Differentiation", Neuron, XP055091729, 65(5): 612-626, Mar. 11, 2010. p. 613, col. 2, Para 2, Figs.3, 4.

Wang et al., Differential expression of microRNA-125b in the neuronal differentiation of adipose-derived Flk1+ mesenchymal stem cells, Journal of Clinical Rehabilitative Tissue Engineering Research, 2010, vol. 14, No. 10, pp. 1711-1715, Beijing, China.

\* cited by examiner

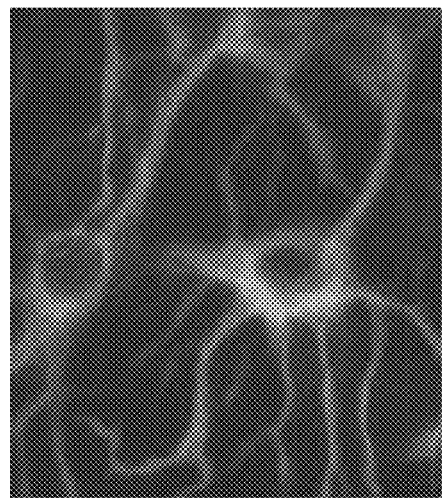
FIG. 9A Unmodified MSCs
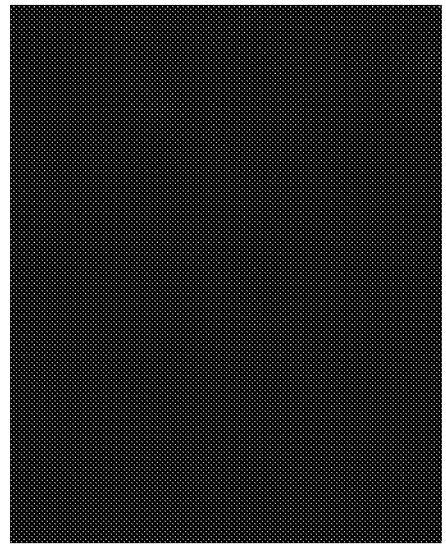
FIG. 9B An-miR-138 + miR-101

MICRORNAS FOR THE GENERATION OF ASTROCYTES

RELATED APPLICATIONS

This application is a National Phase of PCT Patent Application No. PCT/IB2013/051430 having International filing date of Feb. 21, 2013, which claims the benefit of priority under 35 USC § 119(e) of U.S. Provisional Patent Application No. 61/601,624 filed on Feb. 22, 2012. The contents of the above applications are all incorporated by reference as if fully set forth herein in their entirety.

SEQUENCE LISTING STATEMENT

The ASCII file, entitled 60302SequenceListing.txt, created on Aug. 19, 2014, comprising 89,962 bytes, submitted concurrently with the filing of this application is incorporated herein by reference.

FIELD AND BACKGROUND OF THE INVENTION

The present invention, in some embodiments thereof, relates to methods of ex vivo differentiating mesenchymal stem cells towards astrocytic cells using microRNAs.

Mesenchymal stem cells (MSCs) are a heterogeneous population of stromal cells that can be isolated from multiple species, residing in most connective tissues including bone marrow, adipose, placenta, umbilical cord and perivascular tissues. MSCs can also be isolated from the placenta and cord's Wharton's jelly.

The concentration of MSCs in all tissues, including bone marrow and adipose tissue is very low but their number can be expanded in vitro. Typically, expansion of MSCs using up to 15 passages does not result in mutations indicating genetic stability.

MSC can differentiate into cells of the mesenchymal lineage, such as bone, cartilage and fat but, under certain conditions, have been reported to acquire the phenotype of cells of the endodermal and neuroectodermal lineage, suggesting some potential for "transdifferentiation".

Within the bone marrow compartment, these cells are tightly intermingled with and support hematopoiesis and the survival of hematopoietic stem cells in acquiescent state (7). In addition, after expansion in culture, MSCs retain their ability to modulate innate and adaptive immunity (8). Furthermore, MSCs migrate actively to sites of inflammation and protect damaged tissues, including the CNS, properties that supported their use as new immunosuppressive or rather immunoregulatory or anti-inflammatory agents for the treatment of inflammatory and immune-mediated diseases including autoimmune disorders (9). These features of MSCs merited their use to control life-threatening graft-versus-host-disease (GVHD) following allogeneic bone marrow transplantation, thus controlling one of the most serious complications of allogeneic bone marrow transplantation, helping to lower transplant-related toxicity and mortality associated with multi-system organ injury (10).

Several studies have shown that MSCs following exposure to different factors in vitro, change their phenotype and demonstrate neuronal and glial markers [Kopen, G. C., et al., Proc Natl Acad USA. 96(19):10711-6, 1999; Sanchez-Ramos, et al. Exp Neurol. 164(2): 247-56. 2000; Woodbury, D., J Neurosci Res. 61(4): 364-70, 2000; Woodbury, D., et al., J Neurosci Res. 69(6):908-17, 2002; Black, I. B., Woodbury, D. Blood Cells Mol Dis. 27(3):632-6, 2001; Kohyama, J., et al. Differentiation. 68(4-5):235-44, 2001; Levy, Y. S. J Mol Neurosci. 21(2):121-32, 2003].

Accordingly, MSCs (both ex-vivo differentiated and non-differentiated) have been proposed as candidates for cell replacement therapy for the treatment of various neurological disorders including multiple sclerosis, Parkinson's disease, ALS, Alzheimer's disease, spinal cord injury and stroke.

As an alternative to neuronal cell replacement strategy, in order to increase the survival of existing functional and morphologically normal cells, cell therapy may be aimed at restoring or reestablishing the normal anatomy (e.g. connectivity) and physiology (e.g. appropriate synaptic contacts and functioning neurotransmitters and neuroregulators) of a diseased or damaged tissue.

Astrocytes are the most abundant type of glial cells in the central nervous system and play major roles in the development and normal physiological functions of the brain. Mature astrocytes are divided into two types: fibrous and protoplasmic astrocytes.

Fibrous astrocytes populate the white matter and typically have a 'star-like' appearance with dense glial filaments that can be stained with the intermediate filament marker glial fibrillary acidic protein (GFAP). Protoplasmic astrocytes are found in the grey matter, have more irregular, 'bushy', processes and typically have few glial filaments. These cells come into contact with and ensheath thin processes, some of which also contact blood vessels.

Astrocytes also regulate water balance, redox potential and ion and neurotransmitter concentrations, secrete neurotrophic factors, remove toxins and debris from the cerebrospinal fluid (CSF) and maintain the blood-brain bather. They also participate in cell-cell signaling by regulating calcium flux, releasing d-serine, producing neuropeptides and modulating synaptic transmission.

Since astrocytes provide structural and physiological support in the central nervous system, differentiation of MSCs towards an astrocytic lineage has been proposed for the treatment of neurological disorders.

Various cells type produce GDNF including glia cells (oligodendrocytes and astrocytes), neuroblastoma and glioblastoma cell lines. It has been shown that rat BMSCs cultured in DMEM supplemented with 20% fetal bovine serum, at passage 6 express GDNF and NGF [Garcia R, et al., Biochem Biophys Res Commun. 316(3):753-4, 2004].

International Patent Publications WO2006/134602 and WO2009/144718 teach differentiation of mesenchymal stem cells into cells which produce neurotrophic factors.

International Patent Publication WO2010/111522 teaches mesenchymal stem cells which secrete and deliver microRNAs for the treatment of diseases.

International Patent Publication WO2010/144698 teaches expression of miRNAs in mesenchymal stem cells to induce neuronal differentiation thereof.

International Application No. IL2011/000660 teaches expression of miRNAs in mesenchymal stem cells to induce oligodendrocytic differentiation thereof.

SUMMARY OF THE INVENTION

According to an aspect of some embodiments of the present invention there is provided a method of generating a population of cells useful for treating a nerve disease or disorder in a subject, the method comprising up-regulating a level of at least one exogenous miRNA being selected from the group consisting of miR-1293, miR-18, miR-1182, miR-1185, miR-1276, miR-17-5p, miR-141, miR-302b, miR- 20b, miR-101, miR-126, miR-146a, miR-146b, miR-3a, miR-29, miR-504, miR-891, miR-874 and miR-132 in mesenchymal stem cells (MSCs), thereby generating the population of cells useful for treating the nerve disease or disorder.

According to an aspect of some embodiments of the present invention there is provided a method of generating a population of cells useful for treating a nerve disease or disorder in a subject, the method comprising down-regulating an expression of at least one miRNA, the miRNA being selected from the group consisting of mi-R-193b, mi-R-1238, miR-889, mi-R-370, mi-R-548-d1, mi-R-221, mi-R-135a, mi-R-149, mi-R-222, mi-R-199a, mi-R-302a, miR-302b, mi-R-302c, mi-R-302d, mi-R-369-3p, mi-R-let7a, mi-R-let7b, mi-R-10b, mi-R-23a, mi-R-23b, mi-R-138, mi-R-182, mi-R-487, mi-R-214, mi-R-409, miR-133, miR-145 and mi-R-32, wherein the down-regulating is effected by up-regulating a level of at least one polynucleotide agent that hybridizes and inhibits a function of the at least one miRNA thereby generating the population of cells useful for treating the nerve disease or disorder.

According to an aspect of some embodiments of the present invention there is provided a method of generating a population of cells useful for treating a nerve disease or disorder in a subject, the method comprising up-regulating a level of exogenous miR-9 and exogenous miR-20b in a population of MSCs, thereby generating the population of cells.

According to an aspect of some embodiments of the present invention there is provided a method of generating a population of cells useful for treating a nerve disease or disorder in a subject, the method comprising up-regulating a level of exogenous miR-9, exogenous miR-146 and exogenous miR-101 in a population of MSCs and down-regulating an expression of miR-10b and miR-302 using in the population of MSCs thereby generating the population of cells.

According to an aspect of some embodiments of the present invention there is provided a method of generating a population of cells useful for treating a nerve disease or disorder in a subject, the method comprising up-regulating a level of exogenous miR-101 in a population of MSCs and down-regulating an expression of miR-138 in the population of MSCs thereby generating the population of cells.

According to an aspect of some embodiments of the present invention there is provided a genetically modified isolated population of cells which comprise at least one exogenous miRNA selected from the group consisting of miR-18, miR-17-5p, miR-141, miR-302b, miR-20b, miR-101, miR-126, miR-146a, miR-146b, miR-9, miR-504, miR-891, miR-874, miR-1182, miR-1185, miR-1276, miR-1293 and miR-132 and/or at least one polynucleotide agent that hybridizes and inhibits a function of a miRNA being selected from the group consisting of mi-R-193b, mi-R-221, mi-R-135a, mi-R-149, mi-R-222, mi-R-199a, mi-R-302a, mi-R-302c, mi-R-302d, mi-R-369-3p, mi-R-370, mi-R-let7a, mi-R-let7b, mi-R-10b, mi-R-23a, mi-R-23b, mi-R-138, mi-R-182, mi-R-487, mi-R-214, mi-R-409, mi-R-548-d1, mi-R-889, mi-R-1238 and mi-R-32, the cells having an astrocytic phenotype.

According to an aspect of some embodiments of the present invention there is provided a method of treating a nerve disease or disorder in a subject in need thereof, the method comprising administering to the subject a therapeutically effective amount of the isolated population of cells described herein, thereby treating the nerve disease or disorder.

According to an aspect of some embodiments of the present invention there is provided a pharmaceutical composition comprising the isolated population of cells described herein and a pharmaceutically acceptable carrier.

According to an aspect of some embodiments of the present invention there is provided a method of selecting a miRNA which may be regulated for the treatment of a nerve disease or disorder comprising:

(a) differentiating a population of MSCs towards an astrocytic phenotype; and (b) analyzing a change in expression of a miRNA in the population of MSCs prior to and following the differentiating of the MSCs towards an astrocytic phenotype, wherein a change of expression of a miRNA above or below a predetermined level is indicative that the miRNA may be regulated for the treatment of the nerve disease or disorder.

According to an aspect of some embodiments of the present invention there is provided a method of generating a population of cells useful for treating a nerve disease or disorder in a subject, the method comprising up-regulating a level of at least one exogenous miRNA set forth in Table 1 in mesenchymal stem cells (MSCs), thereby generating the population of cells useful for treating the nerve disease or disorder.

According to an aspect of some embodiments of the present invention there is provided a method of generating a population of cells useful for treating a nerve disease or disorder in a subject, the method comprising down-regulating a level of at least one exogenous miRNA set forth in Table 2 in mesenchymal stem cells (MSCs), thereby generating the population of cells useful for treating the nerve disease or disorder.

According to an aspect of some embodiments of the present invention there is provided a method of treating Parkinson's disease in a subject in need thereof, comprising administering to the subject a therapeutically effective amount of MSCs which have been modified to express an exogenous miR504, thereby treating Parkinson's.

According to an aspect of some embodiments of the present invention there is provided a genetically modified isolated population of cells which comprise at least one exogenous miRNA selected from the group consisting of miR-18, miR-1293, miR-1182, miR-1185 and miR-1276 and/or at least one polynucleotide agent that hybridizes and inhibits a function of a miRNA being selected from the group consisting of mi-R-193b, mi-R-1238, miR-889, mi-R-370 and mi-R-548-d1, said cells having an astrocytic phenotype.

According to some embodiments of the invention, the at least one miRNA is selected from the group consisting of miR-18, miR-1293, miR-1182, miR-1185 and miR-1276.

According to some embodiments of the invention, the at least one miRNA is selected from the group consisting of miR-20b, miR-146, miR-101 and miR-141.

According to some embodiments of the invention, the at least one miRNA is selected from the group consisting of miR-32, miR-221, miR-302a and miR-302b.

According to some embodiments of the invention, the at least one miRNA is selected from the group consisting of mi-R-193b, mi-R-1238, miR-889, mi-R-370 and mi-R-548-d1.

According to some embodiments of the invention, the at least one miRNA comprises each of the miR-20b, the miR-101 and the miR-146a.

According to some embodiments of the invention, the MSCs are isolated from a tissue selected from the group consisting of bone marrow, adipose tissue, placenta, cord blood and umbilical cord.

According to some embodiments of the invention, the MSCs are autologous to the subject.

According to some embodiments of the invention, the MSCs are non-autologous to the subject.

According to some embodiments of the invention, the MSCs are semi-allogeneic to the subject.

According to some embodiments of the invention, the up-regulating comprises introducing into the MSCs the miRNAs.

According to some embodiments of the invention, the up-regulating is effected by transfecting the MSCs with an expression vector which comprises a polynucleotide sequence which encodes a pre-miRNA of the at least one miRNA.

According to some embodiments of the invention, the up-regulating is effected by transfecting the MSCs with an expression vector which comprises a polynucleotide sequence which encodes the at least one miRNA.

According to some embodiments of the invention, the method further comprises analyzing an expression of at least one marker selected from the group consisting of S100, GFAP, glutamine synthetase, EAAT1 and EAAT2 following the generating.

According to some embodiments of the invention, the method is effected in vivo.

According to some embodiments of the invention, the method is effected ex vivo.

According to some embodiments of the invention, the method further comprises incubating the MSCs in a differentiation medium comprising at least one agent selected from the group consisting of platelet derived growth factor (PDGF), neuregulin, FGF-b and a c-AMP inducing agent following, prior to or concomitant with the contacting.

According to some embodiments of the invention, at least 50% of the population of cells express at least one marker selected from the group consisting of S100, GFAP, glutamine synthetase, EAAT1 and EAAT2.

According to some embodiments of the invention, the isolated population of cells is for use in treating a brain disease or disorder.

According to some embodiments of the invention, the brain disease or disorder is a neurodegenerative disorder.

According to some embodiments of the invention, the neurodegenerative disorder is selected from the group consisting of multiple sclerosis, Parkinson's, epilepsy, amyotrophic lateral sclerosis (ALS), stroke, Rett Syndrome, autoimmune encephalomyelitis, stroke, Alzheimer's disease and Huntingdon's disease.

According to some embodiments of the invention, the nerve disease or disorder is a neurodegenerative disorder.

According to some embodiments of the invention, the neurodegenerative disorder is selected from the group consisting of multiple sclerosis, Parkinson's, epilepsy, amyotrophic lateral sclerosis (ALS), stroke, Rett Syndrome, autoimmune encephalomyelitis, stroke, Alzheimer's disease and Huntingdon's disease.

According to some embodiments of the invention, the method further comprises analyzing expression of an astrocyte specific gene following step (a) and prior to step (b).

According to some embodiments of the invention, the astrocyte specific gene is GFAP.

According to some embodiments of the invention, the neurodegenerative disorder is selected from the group consisting of multiple sclerosis, Parkinson's, epilepsy, amyotrophic lateral sclerosis (ALS), stroke, Rett Syndrome, autoimmune encephalomyelitis, stroke, Alzheimer's disease and Huntingdon's disease.

Unless otherwise defined, all technical and/or scientific terms used herein have the same meaning as commonly understood by one of ordinary skill in the art to which the invention pertains. Although methods and materials similar or equivalent to those described herein can be used in the practice or testing of embodiments of the invention, exemplary methods and/or materials are described below. In case of conflict, the patent specification, including definitions, will control. In addition, the materials, methods, and examples are illustrative only and are not intended to be necessarily limiting.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

Some embodiments of the invention are herein described, by way of example only, with reference to the accompanying drawings. With specific reference now to the drawings in detail, it is stressed that the particulars shown are by way of example and for purposes of illustrative discussion of embodiments of the invention. In this regard, the description taken with the drawings makes apparent to those skilled in the art how embodiments of the invention may be practiced.

In the drawings:

FIGS. 1A-F are photographs illustrating that MSCs may be differentiated into astrocyte-like cells. BM-MSCs were incubated with the differentiation media and were then analyzed for cell morphology using phase contrast microscopy and were stained with anti-GFAP antibody. Similar results were obtained with AD-MSCs and with MSCs derived from cord and from placenta (data not shown).

Figure 2:
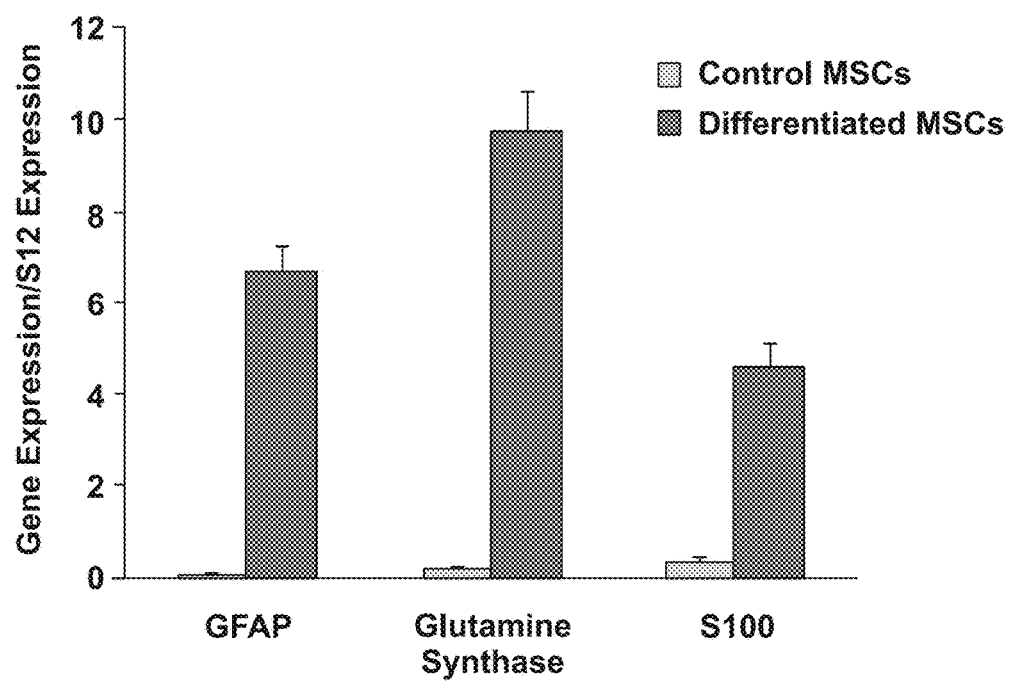

FIG. 2 is a bar graph illustrating that differentiated MSCs express astrocytic markers. Control and differentiated MSCs were treated as described in the methods. RNA was extracted and qRT-PCR was performed using primers for GFAP, glutamine synthetase and S100.

Figure 3:
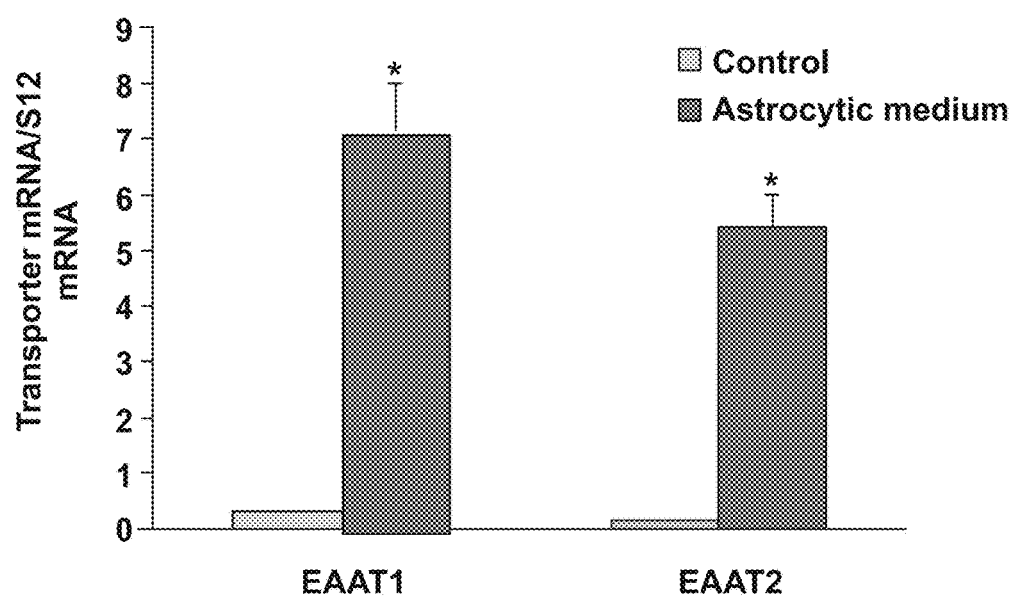

FIG. 3 is a bar graph illustrating that differentiated MSCs express glutamate transporters. Control and differentiated MSCs were treated as described in the methods. RNA was extracted and qRT-PCR was performed using primers for glutamate transporters.

Figure 4:
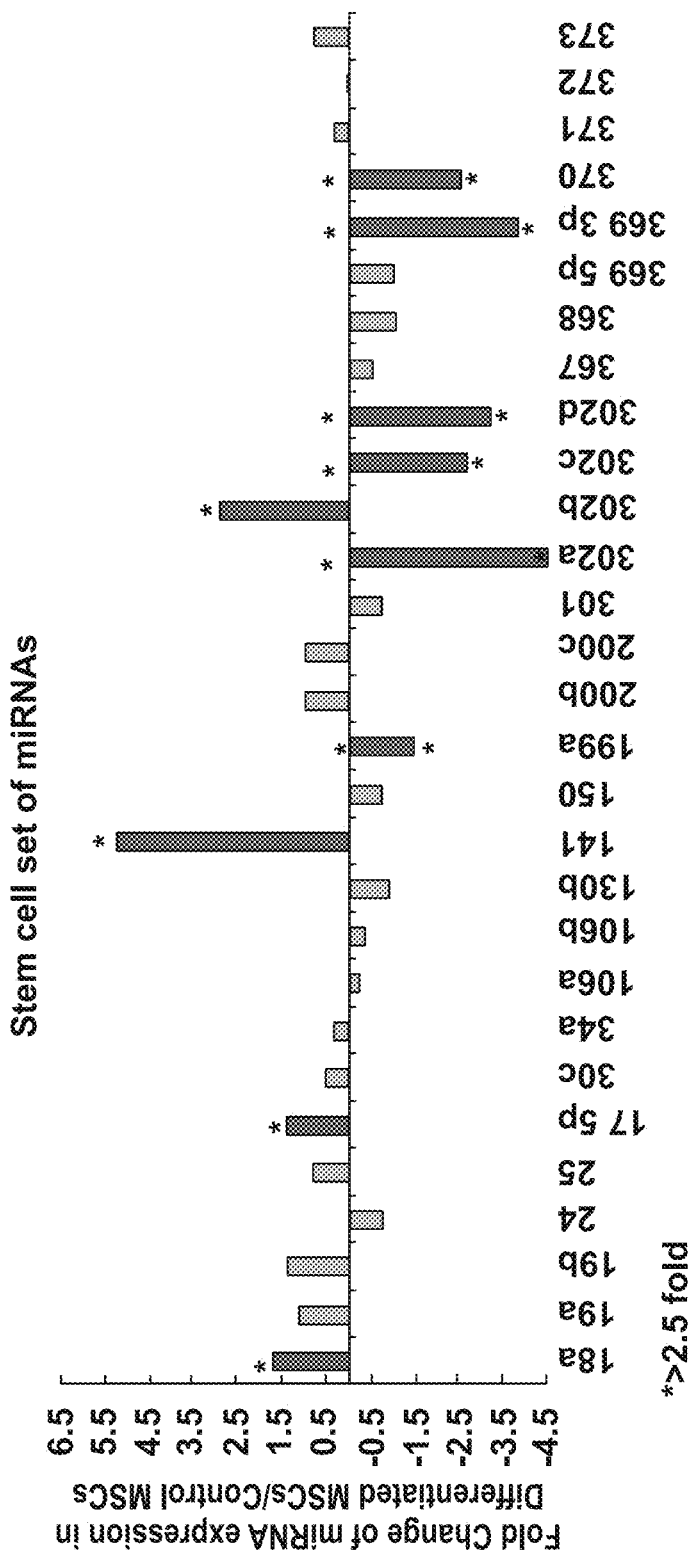

FIG. 4 is a bar graph representing results of the analysis of miRNA signature of stem cell sets of miRNAs. This set consists of miRNAs that are associated with stem cell signature and self renewal.

Figure 5:
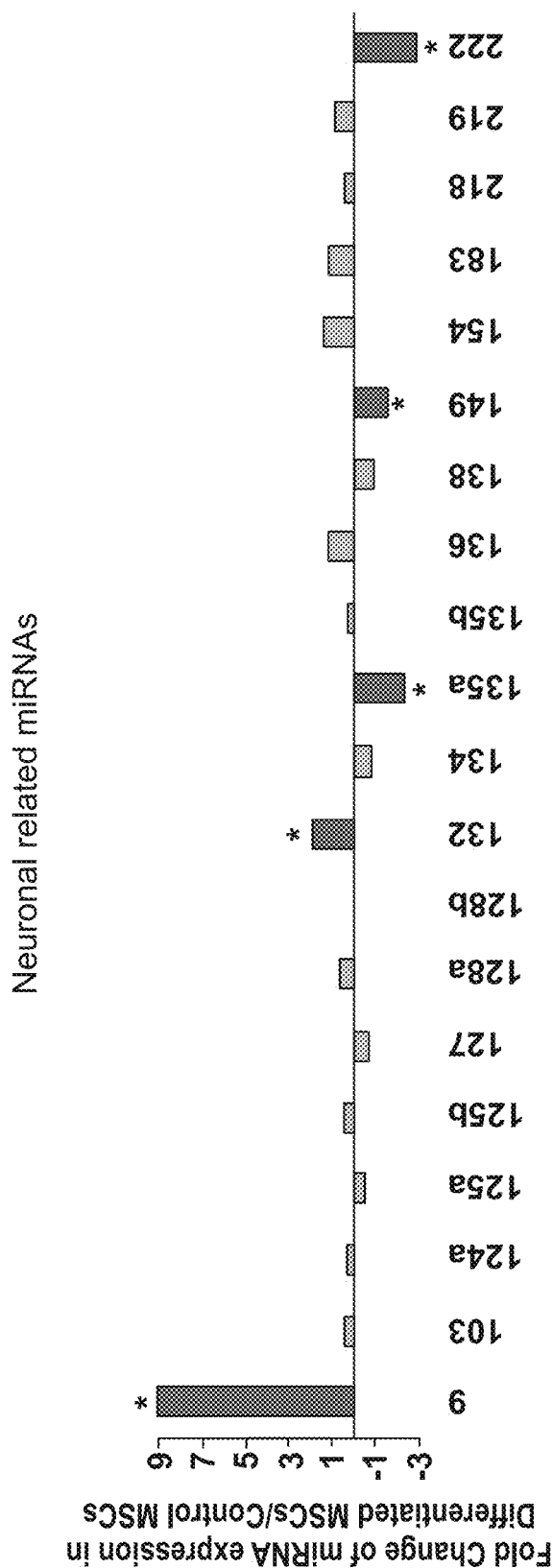

FIG. 5 is a bar graph representing results of the analysis of miRNA signature of the neural set of miRNAs. This set consists of miRNAs that are associated with neural development.

Figure 6:
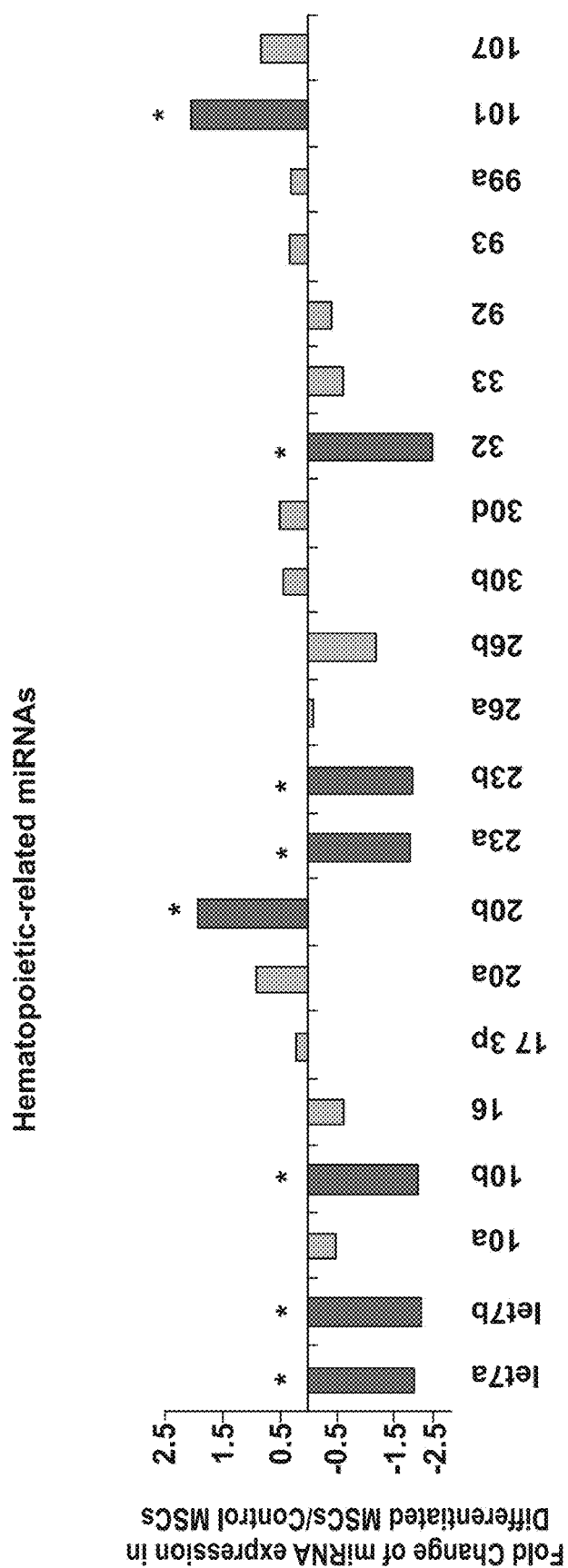

FIG. 6 is a bar graph representing results of the analysis of miRNA signature of the hematopoietic set of miRNAs. This set consists of miRNAs that are associated with hematopoiesis.

Figure 7:
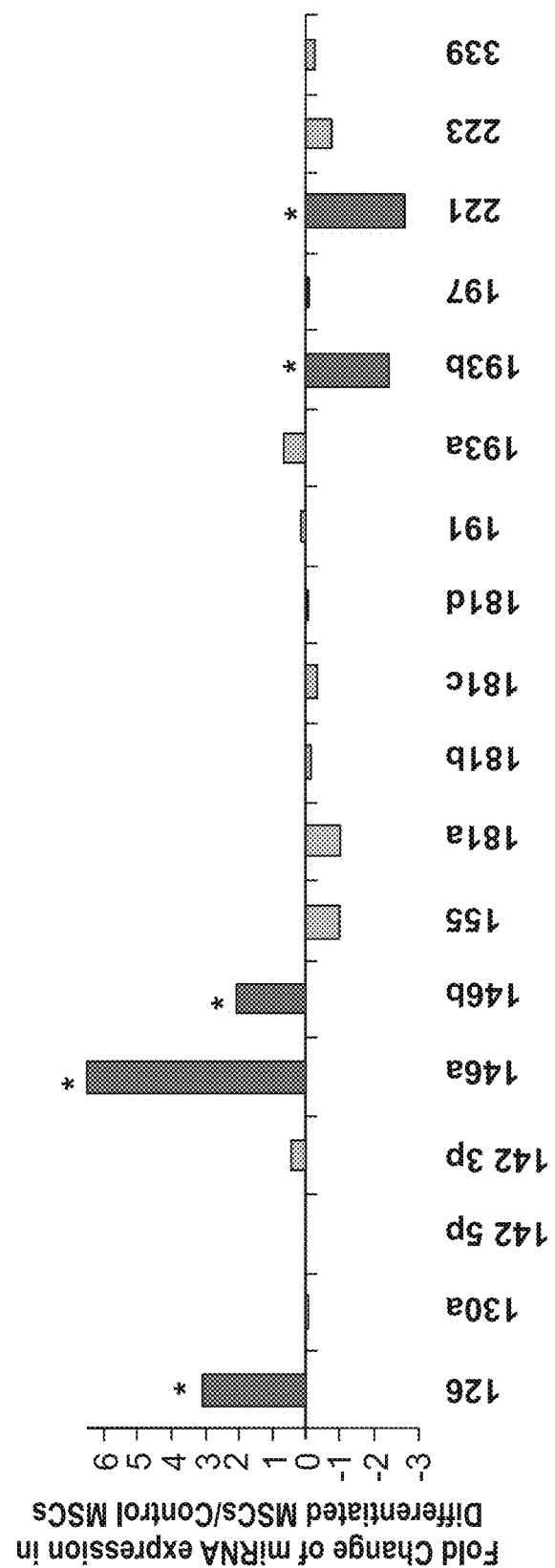

FIG. 7 is a bar graph representing analysis of miRNA signature of the organ set of miRNAs. This set consists of miRNA that are associated with differentiated tissue identification.

Figure 8:
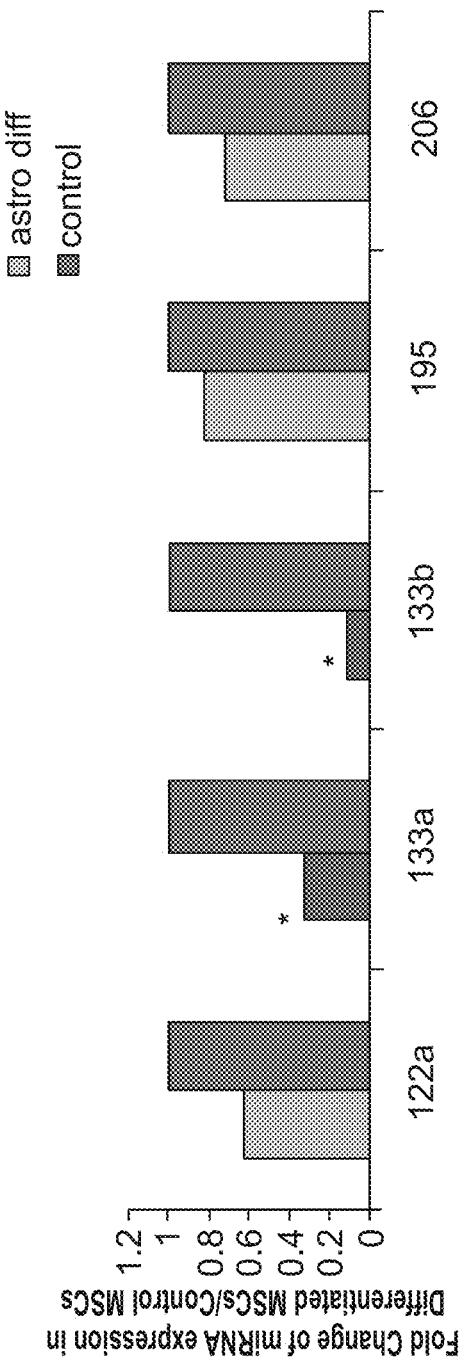

FIG. 8 is a bar graph illustrating a change in expression of exemplary miRNAs during astrocytic differentiation of MSCs as measured by quantitative RT-PCR.

FIGS. 9A-B are photographs of BM-MSCs transduced with a GFAP-GFP reporter. In FIG. 9B, the MSCs were transfected with both antagomiR-138 and miR-101. The cells were viewed under a fluorescence microscope after 10 days.

Figure 10:
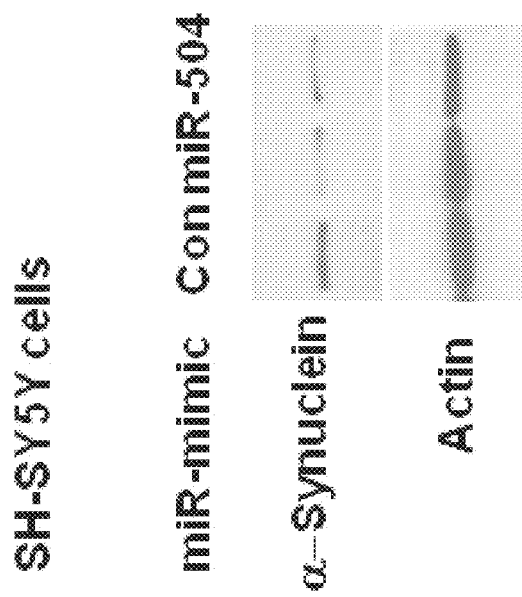

FIG. 10 is a photograph of results of a Western blot analysis illustrating that miRNA 504 downregulates a synuclein in SH-SY5Y cells (lane 1=control; lanes 2+3=miRNA 504).

DESCRIPTION OF SPECIFIC EMBODIMENTS OF THE INVENTION

The present invention, in some embodiments thereof, relates to methods of ex vivo differentiating mesenchymal stem cells towards astrocytic cells using microRNAs.

Before explaining at least one embodiment of the invention in detail, it is to be understood that the invention is not necessarily limited in its application to the details set forth in the following description or exemplified by the Examples. The invention is capable of other embodiments or of being practiced or carried out in various ways.

Astrocytes are the most abundant type of glial cells in the central nervous system and play major roles in the development and normal physiological functions of the brain. Mature astrocytes are divided into two types: fibrous and protoplasmic astrocytes.

Fibrous astrocytes populate the white matter and typically have a 'star-like' appearance with dense glial filaments that can be stained with the intermediate filament marker glial fibrillary acidic protein (GFAP). Protoplasmic astrocytes are found in the grey matter, have more irregular, 'bushy', processes and typically have few glial filaments. These cells come into contact with and ensheath of thin processes, some of which also contact blood vessels.

Astrocytes also regulate water balance, redox potential and ion and neurotransmitter concentrations, secrete neurotrophic factors, remove toxins and debris from the cerebrospinal fluid (CSF) and maintain the blood-brain bather. They also participate in cell-cell signaling by regulating calcium flux, releasing d-serine, producing neuropeptides and modulating synaptic transmission.

Since astrocytes provide structural and physiological support in the central nervous system, generation of cells which have an astrocytic phenotype has been proposed for the treatment of neurological disorders.

Whilst reducing the present invention to practice, the present inventors have found that out of a vast number of potential micro RNAs (miRNAs), only up-regulation of particular miRNAs including miR-18, miR-17-5p, miR-141, miR-302b, miR-20b, miR-101, miR-126, miR-146a, miR-146b, miR-3a, miR-26, miR-29, miR-504, miR-891, miR-874, miR-1182, miR-1185, miR-1276, miR-1293 and miR-132 induces astrocytic differentiation of mesenchymal stem cells (MSCs) and propose that such differentiated MSCs may be used to treat patients with brain diseases or disorders.

Specifically, the present inventors have shown that transfection of MSCs with particular combinations of the miRNAs listed above (e.g. the combination of miR-9 and miR-20b as well as the combination of miR-20b, 101 and 146a) changed the morphological appearance of the cells and further increased expression of various astrocytic markers therein (e.g. GFAP expression).

In addition, the present inventors have identified a number of miRNAs whose down-regulation is associated with astrocytic differentiation of MSCs. Included in this list are mi-R-193b, mi-R-221, mi-R-135a, mi-R-149, mi-R-222, mi-R-199a, mi-R-302a, mi-R-302c, mi-R-302d, mi-R-369-3p, mi-R-370, mi-R-let7a, mi-R-let7b, mi-R-10b, mi-R-23a, mi-R-23b, mi-R-32, miR-133, mi-R-145, mi-R-138, mi-R-182, mi-R-487, mi-R-214, mi-R-409, mi-R-548-d1, mi-R-889 and mi-R-1238. Further it was found that inhibiting miR-10b and miR-302 whilst at the same time over expressing miR-9, 146 and 101 enhanced differentiation towards an astrocytic phenotype as measured by GFAP expression. In addition, it was found that inhibiting miR-138, whilst at the same time overexpressing miR-101 enhanced differentiation towards an astrocytic phenotype as measured by GFAP expression.

Thus, according to one aspect of the present invention, there is provided a method of generating a population of cells useful for treating a nerve disease or disorder in a subject, the method comprising up-regulating a level of at least one exogenous miRNA being selected from the group consisting of miR-18, miR-17-5p, miR-141, miR-302b, miR-20b, miR-101, miR-126, miR-146a, miR-146b, miR-3a, miR-26, miR-29, miR-132, miR-504, miR-891, miR-874, miR-1182, miR-1185, miR-1276 and miR-1293 in mesenchymal stem cells (MSCs), thereby generating the population of cells useful for treating the nerve disease or disorder.

Additional miRNAs contemplated for upregulation are provided herein below. miR-92ap, miR-21, miR-26a, miR-18a, miR-124, miR-99a, miR-30c, miR-301a, miR-145-50, miR-143-3p, miR-373, miR-20b, miR-29c, miR-29b, miR-143, let-7g, let-7a, let-7b, miR-98, miR-30a*, miR-17, miR-1, miR-192, miR-155, miR-516-ap, miR-31, miR-181a, miR-181b, miR-181c, miR-34-c, miR-34b*, miR-103a, miR-210, miR-16, miR-30a, miR-31, miR-222, miR-17, miR-17*, miR-200b, miR-200c, miR-128, miR-503, miR-424, miR-195, miR-1256, miR-203a, miR-199, miR-93, miR-98, miR-125-a, miR-133a, miR-133b, miR-126, miR-194, miR-346, miR-15b, miR-338-3p, miR-373, miR-205, miR-210, miR-125, miR-1226, miR-708, miR-449, miR-422, miR-340, miR-605, miR-522, miR-663, miR-130a, miR-130b, miR-942, miR-572, miR-520, miR-639, miR-654, miR-519, mir-202, mir-767-5p, mir-29a, mir-29b, mir-29c, let-7a, let-7b, let-7c, let-7d, let-7e, let-7f, let-7g, let-7i, mir-4458, mir-4500, mir-98, mir-148a, mir-148b, mir-152, mir-4658, mir-3662, mir-25, mir-32, mir-363, mir-367, mir-92a, mir-92b, mir-520d-5p, mir-524-5p, mir-4724-3p, mir-1294, mir-143, mir-4770, mir-3659, mir-145, mir-3163, mir-181a, mir-181b, mir-181c, mir-181d, mir-4262, mir-4279, mir-144, mir-642b, mir-4742-3p, mir-3177-5p, mir-656, mir-3121-3p, mir-106a, mir-106b, mir-17, mir-20a, mir-20b, mir-519d, mir-93, mir-1297, mir-26a, mir-26b, mir-4465, mir-326, mir-330-5p, mir-3927 and mir-2113.

Additional miRNAs contemplated for upregulation include, mir-372, mir-373, mir-520a-3p, mir-520b, mir-520c-3p, mir-520d-3p, mir-520e, mir-199a-3p, mir-199b-3p, mir-3129-5p.

The upregulation may be effected in vivo or ex vivo.

Mesenchymal stem cells give rise to one or more mesenchymal tissues (e.g., adipose, osseous, cartilaginous, elastic and fibrous connective tissues, myoblasts) as well as to tissues other than those originating in the embryonic mesoderm (e.g., neural cells) depending upon various influences from bioactive factors such as cytokines. Although such cells can be isolated from embryonic yolk sac, placenta, umbilical cord, fetal and adolescent skin, blood and other tissues, their abundance in the easily accessible fat tissue and BM far exceeds their abundance in other tissues and as such isolation from BM and fat tissue is presently preferred.

Methods of isolating, purifying and expanding mesenchymal stem cells (MSCs) are known in the arts and include, for example, those disclosed by Caplan and Haynesworth in U.S. Pat. No. 5,486,359 and Jones E. A. et al., 2002, Isolation and characterization of bone marrow multipotential mesenchymal progenitor cells, Arthritis Rheum. 46(12): 3349-60.

Mesenchymal stem cells may be isolated from various tissues including but not limited to bone marrow, peripheral blood, blood, placenta (e.g. chorionic and/or amniotic), cord blood, umbilical cord, amniotic fluid and from adipose tissue.

A method of isolating mesenchymal stem cells from peripheral blood is described by Kassis et al [Bone Marrow Transplant. 2006 May; 37(10):967-76]. A method of isolating mesenchymal stem cells from placental tissue is described by Zhang et al [Chinese Medical Journal, 2004, 117 (6):882-887]. Methods of isolating and culturing adipose tissue, placental and cord blood mesenchymal stem cells are described by Kern et al [Stem Cells, 2006; 24:1294-1301].

According to a preferred embodiment of this aspect of the present invention, the mesenchymal stem cells are human.

According to another embodiment of this aspect of the present invention, the mesenchymal stem cells are isolated from placenta and umbilical cord of newborn humans.

Bone marrow can be isolated from the iliac crest of an individual by aspiration. Low-density BM mononuclear cells (BMMNC) may be separated by a FICOL-PAQUE density gradient or by elimination of red blood cells using Hetastarch (hydroxyethyl starch). Preferably, mesenchymal stem cell cultures are generated by diluting BM aspirates (usually 20 ml) with equal volumes of Hank's balanced salt solution (HBSS; GIBCO Laboratories, Grand Island, N.Y., USA) and layering the diluted cells over about 10 ml of a Ficoll column (Ficoll-Paque; Pharmacia, Piscataway, N.J., USA). Following 30 minutes of centrifugation at 2,500×g, the mononuclear cell layer is removed from the interface and suspended in HBSS. Cells are then centrifuged at 1,500×g for 15 minutes and resuspended in a complete medium (MEM, a medium without deoxyribonucleotides or ribonucleotides; GIBCO); 20% fetal calf serum (FCS) derived from a lot selected for rapid growth of MSCs (Atlanta Biologicals, Norcross, Ga.); 100 units/ml penicillin (GIBCO), 100 μg/ml streptomycin (GIBCO); and 2 mM L-glutamine (GIBCO). Resuspended cells are plated in about 25 ml of medium in a 10 cm culture dish (Corning Glass Works, Corning, N.Y.) and incubated at 37° C. with 5% humidified $CO_2$. Following 24 hours in culture, non-adherent cells are discarded, and the adherent cells are thoroughly washed twice with phosphate buffered saline (PBS). The medium is replaced with a fresh complete medium every 3 or 4 days for about 14 days.

Adherent cells are then harvested with 0.25% trypsin and 1 mM EDTA (Trypsin/EDTA, GIBCO) for 5 min at 37° C., replated in a 6-cm plate and cultured for another 14 days. Cells are then trypsinized and counted using a cell counting device such as for example, a hemocytometer (Hausser Scientific, Horsham, Pa.). Cultured cells are recovered by centrifugation and resuspended with 5% DMSO and 30% FCS at a concentration of 1 to $2 \times 10^6$ cells per ml. Aliquots of about 1 ml each are slowly frozen and stored in liquid nitrogen.

Adipose tissue-derived MSCs can be obtained by liposuction and mononuclear cells can be isolated manually by removal of the fat and fat cells, or using the Celution System (Cytori Therapeutics) following the same procedure as described above for preparation of MSCs.

According to one embodiment the populations are plated on polystyrene plastic surfaces (e.g. in a flask) and mesenchymal stem cells are isolated by removing non-adherent cells. Alternatively mesenchymal stem cell may be isolated by FACS using mesenchymal stem cell markers.

Preferably the MSCs are at least 50% purified, more preferably at least 75% purified and even more preferably at least 90% purified.

To expand the mesenchymal stem cell fraction, frozen cells are thawed at 37° C., diluted with a complete medium and recovered by centrifugation to remove the DMSO.

Cells are resuspended in a complete medium and plated at a concentration of about 5,000 cells/$cm^2$. Following 24 hours in culture, non-adherent cells are removed and the adherent cells are harvested using Trypsin/EDTA, dissociated by passage through a narrowed Pasteur pipette, and preferably replated at a density of about 1.5 to about 3.0 cells/$cm^2$. Under these conditions, MSC cultures can grow for about 50 population doublings and be expanded for about 2000 fold [Colter D C., et al. Rapid expansion of recycling stem cells in cultures of plastic-adherent cells from human bone marrow. Proc Natl Acad Sci USA. 97: 3213-3218, 2000].

MSC cultures utilized by some embodiments of the invention preferably include three groups of cells which are defined by their morphological features: small and agranular cells (referred to as RS-1, herein below), small and granular cells (referred to as RS-2, herein below) and large and moderately granular cells (referred to as mature MSCs, herein below). The presence and concentration of such cells in culture can be assayed by identifying a presence or absence of various cell surface markers, by using, for example, immunofluorescence, in situ hybridization, and activity assays.

When MSCs are cultured under the culturing conditions of some embodiments of the invention they exhibit negative staining for the hematopoietic stem cell markers CD34, CD11B, CD43 and CD45. A small fraction of cells (less than 10%) are dimly positive for CD31 and/or CD38 markers. In addition, mature MSCs are dimly positive for the hematopoietic stem cell marker, CD117 (c-Kit), moderately positive for the osteogenic MSCs marker, Stro-1 [Simmons, P. J. & Torok-Storb, B. (1991). Blood 78, 5562] and positive for the thymocytes and peripheral T lymphocytes marker, CD90 (Thy-1). On the other hand, the RS-1 cells are negative for the CD117 and Stro1 markers and are dimly positive for the CD90 marker, and the RS-2 cells are negative for all of these markers.

The mesenchymal stem cells of the present invention may be of autologous, syngeneic or allogeneic related (matched siblings or haploidentical family members) or unrelated fully mismatched source, as further described herein below.

Culturing of the mesenchymal stem cells can be performed in any media that support (or at least does not inhibit) the differentiation of the cells towards astrocytic cells such as those described in U.S. Pat. No. 6,528,245 and by Sanchez-Ramos et al. (2000); Woodburry et al. (2000); Woodburry et al. (J. Neurosci. Res. 96:908-917, 2001); Black and Woodbury (Blood Cells Mol. Dis. 27:632-635, 2001); Deng et al. (2001), Kohyama et al. (2001), Reyes and Verfatile (Ann N.Y. Acad. Sci. 938:231-235, 2001) and Jiang et al. (Nature 418:47-49, 2002).

The media may be G5, neurobasal medium, DMEM or DMEM/F12, OptiMEM™ or any other medium that supports neuronal or astrocytic growth.

According to a particular embodiment the miRNA comprises at least one of miR-20b, miR-146, miR-101 and miR-141.

A particular combination contemplated by the present inventors includes up-regulating each of miR-20b, miR-101 and miR-146a in the MSC population.

Another combination contemplated by the present inventors is up-regulating the level of exogenous miR-9 and exogenous miR-20b in the MSC population.

The term "microRNA", "miRNA", and "miR" are synonymous and refer to a collection of non-coding single-stranded RNA molecules of about 19-28 nucleotides in length, which regulate gene expression. MiRNAs are found in a wide range of organisms and have been shown to play a role in development, homeostasis, and disease etiology.

Below is a brief description of the mechanism of miRNA activity.

Genes coding for miRNAs are transcribed leading to production of an miRNA precursor known as the pri-miRNA. The pri-miRNA is typically part of a polycistronic RNA comprising multiple pri-miRNAs. The pri-miRNA may form a hairpin with a stem and loop. The stem may comprise mismatched bases.

The hairpin structure of the pri-miRNA is recognized by Drosha, which is an RNase III endonuclease. Drosha typically recognizes terminal loops in the pri-miRNA and cleaves approximately two helical turns into the stem to produce a 60-70 nt precursor known as the pre-miRNA. Drosha cleaves the pri-miRNA with a staggered cut typical of RNase III endonucleases yielding a pre-miRNA stem loop with a 5' phosphate and ~2 nucleotide 3' overhang. It is estimated that approximately one helical turn of stem (~10 nucleotides) extending beyond the Drosha cleavage site is essential for efficient processing. The pre-miRNA is then actively transported from the nucleus to the cytoplasm by Ran-GTP and the export receptor exportin-5.

The double-stranded stem of the pre-miRNA is then recognized by Dicer, which is also an RNase III endonuclease. Dicer may also recognize the 5' phosphate and 3' overhang at the base of the stem loop. Dicer then cleaves off the terminal loop two helical turns away from the base of the stem loop leaving an additional 5' phosphate and ~2 nucleotide 3' overhang. The resulting siRNA-like duplex, which may comprise mismatches, comprises the mature miRNA and a similar-sized fragment known as the miRNA*. The miRNA and miRNA* may be derived from opposing arms of the pri-miRNA and pre-miRNA. miRNA* sequences may be found in libraries of cloned miRNAs but typically at lower frequency than the miRNAs.

Although initially present as a double-stranded species with miRNA*, the miRNA eventually become incorporated as a single-stranded RNA into a ribonucleoprotein complex known as the RNA-induced silencing complex (RISC). Various proteins can form the RISC, which can lead to variability in specificity for miRNA/miRNA* duplexes, binding site of the target gene, activity of miRNA (repress or activate), and which strand of the miRNA/miRNA* duplex is loaded in to the RISC.

When the miRNA strand of the miRNA:miRNA* duplex is loaded into the RISC, the miRNA* is removed and degraded. The strand of the miRNA:miRNA* duplex that is loaded into the RISC is the strand whose 5' end is less tightly paired. In cases where both ends of the miRNA:miRNA* have roughly equivalent 5' pairing, both miRNA and miRNA* may have gene silencing activity.

The RISC identifies target nucleic acids based on high levels of complementarity between the miRNA and the mRNA, especially by nucleotides 2-7 of the miRNA.

A number of studies have looked at the base-pairing requirement between miRNA and its mRNA target for achieving efficient inhibition of translation (reviewed by Bartel 2004, Cell 116-281). In mammalian cells, the first 8 nucleotides of the miRNA may be important (Doench & Sharp 2004 Genes Dev 2004-504). However, other parts of the microRNA may also participate in mRNA binding. Moreover, sufficient base pairing at the 3' can compensate for insufficient pairing at the 5' (Brennecke et al, 2005 PLoS 3-e85). Computation studies, analyzing miRNA binding on whole genomes have suggested a specific role for bases 2-7 at the 5' of the miRNA in target binding but the role of the first nucleotide, found usually to be "A" was also recognized (Lewis et at 2005 Cell 120-15). Similarly, nucleotides 1-7 or 2-8 were used to identify and validate targets by Krek et al (2005, Nat Genet 37-495).

The target sites in the mRNA may be in the 5' UTR, the 3' UTR or in the coding region. Interestingly, multiple miRNAs may regulate the same mRNA target by recognizing the same or multiple sites. The presence of multiple miRNA binding sites in most genetically identified targets may indicate that the cooperative action of multiple RISCs provides the most efficient translational inhibition.

miRNAs may direct the RISC to downregulate gene expression by either of two mechanisms: mRNA cleavage or translational repression. The miRNA may specify cleavage of the mRNA if the mRNA has a certain degree of complementarity to the miRNA. When a miRNA guides cleavage, the cut is typically between the nucleotides pairing to residues 10 and 11 of the miRNA. Alternatively, the miRNA may repress translation if the miRNA does not have the requisite degree of complementarity to the miRNA. Translational repression may be more prevalent in animals since animals may have a lower degree of complementarity between the miRNA and binding site.

It should be noted that there may be variability in the 5' and 3' ends of any pair of miRNA and miRNA*. This variability may be due to variability in the enzymatic processing of Drosha and Dicer with respect to the site of cleavage. Variability at the 5' and 3' ends of miRNA and miRNA* may also be due to mismatches in the stem structures of the pri-miRNA and pre-miRNA. The mismatches of the stem strands may lead to a population of different hairpin structures. Variability in the stem structures may also lead to variability in the products of cleavage by Drosha and Dicer.

The term "microRNA mimic" refers to synthetic non-coding RNAs that are capable of entering the RNAi pathway and regulating gene expression. miRNA mimics imitate the function of endogenous microRNAs (miRNAs) and can be designed as mature, double stranded molecules or mimic precursors (e.g., or pre-miRNAs). miRNA mimics can be comprised of modified or unmodified RNA, DNA, RNA-DNA hybrids, or alternative nucleic acid chemistries (e.g., LNAs or 2'-O, 4'-C-ethylene-bridged nucleic acids (ENA)). Other modifications are described herein below. For mature, double stranded miRNA mimics, the length of the duplex region can vary between 13-33, 18-24 or 21-23 nucleotides. The miRNA may also comprise a total of at least 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39 or 40 nucleotides. The sequence of the miRNA may be the first 13-33 nucleotides of the pre-miRNA. The sequence of the miRNA may also be the last 13-33 nucleotides of the pre-miRNA. The sequence of the miRNA may comprise any of the sequences of the disclosed miRNAs, or variants thereof.

It will be appreciated from the description provided herein above, that contacting mesenchymal stem cells may be affected in a number of ways:

1. Transiently transfecting the mesenchymal stem cells with the mature miRNA (or modified form thereof, as described herein below). The miRNAs designed according to the teachings of the present invention can be generated according to any oligonucleotide synthesis method known in the art, including both enzymatic syntheses and solid-phase syntheses. Equipment and reagents for executing solid-phase synthesis are commercially available from, for example, Applied Biosystems. Any other means for such synthesis may also be employed; the actual synthesis of the oligonucleotides is well within the capabilities of one skilled in the art and can be accomplished via established methodologies as detailed in, for example: Sambrook, J. and Russell, D. W. (2001), "Molecular Cloning: A Laboratory Manual"; Ausubel, R. M. et al., eds. (1994, 1989), "Current Protocols in Molecular Biology," Volumes I-III, John Wiley & Sons, Baltimore, Md.; Perbal, B. (1988), "A Practical Guide to Molecular Cloning," John Wiley & Sons, New York; and Gait, M. J., ed. (1984), "Oligonucleotide Synthesis"; utilizing solid-phase chemistry, e.g. cyanoethyl phosphoramidite followed by deprotection, desalting, and purification by, for example, an automated trityl-on method or HPLC.

2. Stably, or transiently transfecting the mesenchymal stem cells with an expression vector which encodes the mature miRNA.

3. Stably, or transiently transfecting the mesenchymal stem cells with an expression vector which encodes the pre-miRNA. The pre-miRNA sequence may comprise from 45-90, 60-80 or 60-70 nucleotides. The sequence of the pre-miRNA may comprise a miRNA and a miRNA* as set forth herein. The sequence of the pre-miRNA may also be that of a pri-miRNA excluding from 0-160 nucleotides from the 5' and 3' ends of the pri-miRNA. The sequence of the pre-miRNA may comprise the sequence of the miRNA.

4. Stably, or transiently transfecting the mesenchymal stem cells with an expression vector which encodes the pri-miRNA. The pri-miRNA sequence may comprise from 45-30,000, 50-25,000, 100-20,000, 1,000-1,500 or 80-100 nucleotides. The sequence of the pri-miRNA may comprise a pre-miRNA, miRNA and miRNA*, as set forth herein, and variants thereof. Preparation of miRNAs mimics can be effected by chemical synthesis methods or by recombinant methods.

As mentioned, the present invention also contemplates differentiation of mesenchymal stem cells towards an astrocytic phenotype by down-regulation of particular miR-NAs—namely mi-R-193b, mi-R-221, mi-R-135a, mi-R-149, mi-R-222, mi-R-199a, mi-R-302, mi-R-302c, mi-R-302d, mi-R-369-3p, mi-R-370, mi-R-let7a, mi-R-let7b, mi-R-10b, mi-R-23a, mi-R-23b, mi-R-32, miR-145, miR-133, mi-R-138, mi-R-182, mi-R-487, mi-R-214, mi-R-409, mi-R-548-d1, mi-R-889, as well as mi-R-1238.

Additional miRNAs contemplated for down-regulation are set forth below. miR-204, miR-224, miR-616, miR-122, miR-299, miR-100, miR-138, miR-140, miR-375, miR-217, miR-302, miR-372, miR-96, miR-127-3p, miR-449, miR-135b, miR-101, miR-326, miR-324, miR-335, miR-14, miR-16.

Additional miRNAs contemplated for down-regulation are set forth below. mir-410, mir-3163, mir-148a, mir-148b, mir-152, mir-3121-3p, mir-495, mir-203, mir-4680-3p.

According to a particular embodiment, at least one of miR-32, miR-221, miR-302a, miR-138 and miR-302b is down-regulated in order to produce the astrocyte-like cells of the present invention.

Down-regulating miRNAs can be affected using a polynucleotide which is hybridizable in cells under physiological conditions to the miRNA.

According to a particular embodiment, the cell population is generated by up-regulating an expression of miR-9, miR-146 and miR-101 in a population of MSCs and down-regulating an expression of miR-10b and miR-302 in the population of MSCs.

According to another embodiment, the cell population is generated by up-regulating an expression of miR-101 and down-regulating an expression of miR-138.

As used herein, the term "hybridizable" refers to capable of hybridizing, i.e., forming a double strand molecule such as RNA:RNA, RNA:DNA and/or DNA:DNA molecules. "Physiological conditions" refer to the conditions present in cells, tissue or a whole organism or body. Preferably, the physiological conditions used by the present invention include a temperature between 34-40° C., more preferably, a temperature between 35-38° C., more preferably, a temperature between 36 and 37.5° C., most preferably, a temperature between 37 to 37.5° C.; salt concentrations (e.g., sodium chloride NaCl) between 0.8-1%, more preferably, about 0.9%; and/or pH values in the range of 6.5-8, more preferably, 6.5-7.5, most preferably, pH of 7-7.5.

As mentioned herein above, the polynucleotides which downregulate the above list of miRNAs and the miRNAs described herein above may be provided as modified polynucleotides using various methods known in the art.

For example, the oligonucleotides (e.g. miRNAs) or polynucleotides of the present invention may comprise heterocylic nucleosides consisting of purines and the pyrimidines bases, bonded in a 3'-to-5' phosphodiester linkage.

Preferably used oligonucleotides or polynucleotides are those modified either in backbone, internucleoside linkages, or bases, as is broadly described herein under.

Specific examples of preferred oligonucleotides or polynucleotides useful according to this aspect of the present invention include oligonucleotides or polynucleotides containing modified backbones or non-natural internucleoside linkages.

Oligonucleotides or polynucleotides having modified backbones include those that retain a phosphorus atom in the backbone, as disclosed in U.S. Pat. Nos. 4,469,863; 4,476,301; 5,023,243; 5,177,196; 5,188,897; 5,264,423; 5,276,019; 5,278,302; 5,286,717; 5,321,131; 5,399,676; 5,405,939; 5,453,496; 5,455,233; 5,466,677; 5,476,925; 5,519,126; 5,536,821; 5,541,306; 5,550,111; 5,563,253; 5,571,799; 5,587,361; and 5,625,050.

Preferred modified oligonucleotide or polynucleotide backbones include, for example: phosphorothioates; chiral phosphorothioates; phosphorodithioates; phosphotriesters; aminoalkyl phosphotriesters; methyl and other alkyl phosphonates, including 3'-alkylene phosphonates and chiral phosphonates; phosphinates; phosphoramidates, including 3'-amino phosphoramidate and aminoalkylphosphoramidates; thionophosphoramidates; thionoalkylphosphonates; thionoalkylphosphotriesters; and boranophosphates having normal 3'-5' linkages, 2'-5' linked analogues of these, and those having inverted polarity wherein the adjacent pairs of nucleoside units are linked 3'-5' to 5'-3' or 2'-5' to 5'-2'.

Various salts, mixed salts, and free acid forms of the above modifications can also be used.

Alternatively, modified oligonucleotide or polynucleotide backbones that do not include a phosphorus atom therein have backbones that are formed by short-chain alkyl or cycloalkyl internucleoside linkages, mixed heteroatom and alkyl or cycloalkyl internucleoside linkages, or one or more short-chain heteroatomic or heterocyclic internucleoside linkages. These include those having morpholino linkages (formed in part from the sugar portion of a nucleoside); siloxane backbones; sulfide, sulfoxide, and sulfone backbones; formacetyl and thioformacetyl backbones; methylene formacetyl and thioformacetyl backbones; alkene-containing backbones; sulfamate backbones; methyleneimino and methylenehydrazino backbones; sulfonate and sulfonamide backbones; amide backbones; and others having mixed N, O, S and $CH_2$ component parts, as disclosed in U.S. Pat. Nos. 5,034,506; 5,166,315; 5,185,444; 5,214,134; 5,216,141; 5,235,033; 5,264,562; 5,264,564; 5,405,938; 5,434,257; 5,466,677; 5,470,967; 5,489,677; 5,541,307; 5,561,225; 5,596,086; 5,602,240; 5,610,289; 5,602,240; 5,608,046; 5,610,289; 5,618,704; 5,623,070; 5,663,312; 5,633,360; 5,677,437; and 5,677,439.

Other oligonucleotides or polynucleotides which may be used according to the present invention are those modified in both sugar and the internucleoside linkage, i.e., the backbone of the nucleotide units is replaced with novel groups. The base units are maintained for complementation with the appropriate polynucleotide target. An example of such an oligonucleotide mimetic includes a peptide nucleic acid (PNA). A PNA oligonucleotide refers to an oligonucleotide where the sugar-backbone is replaced with an amide-containing backbone, in particular an aminoethylglycine backbone. The bases are retained and are bound directly or indirectly to aza-nitrogen atoms of the amide portion of the backbone. United States patents that teach the preparation of PNA compounds include, but are not limited to, U.S. Pat. Nos. 5,539,082; 5,714,331; and 5,719,262; each of which is herein incorporated by reference. Other backbone modifications which may be used in the present invention are disclosed in U.S. Pat. No. 6,303,374.

Oligonucleotides or polynucleotides of the present invention may also include base modifications or substitutions. As used herein, "unmodified" or "natural" bases include the purine bases adenine (A) and guanine (G) and the pyrimidine bases thymine (T), cytosine (C), and uracil (U). "Modified" bases include but are not limited to other synthetic and natural bases, such as: 5-methylcytosine (5-me-C); 5-hydroxymethyl cytosine; xanthine; hypoxanthine; 2-aminoadenine; 6-methyl and other alkyl derivatives of adenine and guanine; 2-propyl and other alkyl derivatives of adenine and guanine; 2-thiouracil, 2-thiothymine, and 2-thiocytosine; 5-halouracil and cytosine; 5-propynyl uracil and cytosine; 6-azo uracil, cytosine, and thymine; 5-uracil (pseudouracil); 4-thiouracil; 8-halo, 8-amino, 8-thiol, 8-thioalkyl, 8-hydroxyl, and other 8-substituted adenines and guanines; 5-halo, particularly 5-bromo, 5-trifluoromethyl, and other 5-substituted uracils and cytosines; 7-methylguanine and 7-methyladenine; 8-azaguanine and 8-azaadenine; 7-deazaguanine and 7-deazaadenine; and 3-deazaguanine and 3-deazaadenine. Additional modified bases include those disclosed in: U.S. Pat. No. 3,687,808; Kroschwitz, J. I., ed. (1990), "The Concise Encyclopedia Of Polymer Science And Engineering," pages 858-859, John Wiley & Sons; Englisch et al. (1991), "Angewandte Chemie," International Edition, 30, 613; and Sanghvi, Y. S., "Antisense Research and Applications," Chapter 15, pages 289-302, S. T. Crooke and B. Lebleu, eds., CRC Press, 1993. Such modified bases are particularly useful for increasing the binding affinity of the oligomeric compounds of the invention. These include 5-substituted pyrimidines, 6-azapyrimidines, and N-2, N-6, and O-6-substituted purines, including 2-aminopropyladenine, 5-propynyluracil, and 5-propynylcytosine. 5-methylcytosine substitutions have been shown to increase nucleic acid duplex stability by 0.6-1.2° C. (Sanghvi, Y. S. et al. (1993), "Antisense Research and Applications," pages 276-278, CRC Press, Boca Raton), and are presently preferred base substitutions, even more particularly when combined with 2'-O-methoxyethyl sugar modifications.

To express miRNAs or polynucleotide agents which regulate miRNAs in mesencyhymal stem cells, a polynucleotide sequence encoding the miRNA (or pre-miRNA, or pri-miRNA, or polynucleotide which down-regulates the miRNAs) is preferably ligated into a nucleic acid construct suitable for mesenchymal stem cell expression. Such a nucleic acid construct includes a promoter sequence for directing transcription of the polynucleotide sequence in the cell in a constitutive or inducible manner.

It will be appreciated that the nucleic acid construct of some embodiments of the invention can also utilize miRNA homologues which exhibit the desired activity (i.e., astrocytic differentiating ability). Such homologues can be, for example, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any of the sequences provided, as determined using the BestFit software of the Wisconsin sequence analysis package, utilizing the Smith and Waterman algorithm, where gap weight equals 50, length weight equals 3, average match equals 10 and average mismatch equals −9.

In addition, the homologues can be, for example, at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99% or 100% identical to any of the sequences provided herein, as determined using the BestFit software of the Wisconsin sequence analysis package, utilizing the Smith and Waterman algorithm, where gap weight equals 50, length weight equals 3, average match equals 10 and average mismatch equals −9.

Constitutive promoters suitable for use with some embodiments of the invention are promoter sequences which are active under most environmental conditions and most types of cells such as the cytomegalovirus (CMV) and Rous sarcoma virus (RSV).

Inducible promoters suitable for use with some embodiments of the invention include for example tetracycline-inducible promoter (Zabala M, et al., Cancer Res. 2004, 64(8): 2799-804).

Eukaryotic promoters typically contain two types of recognition sequences, the TATA box and upstream promoter elements. The TATA box, located 25-30 base pairs upstream of the transcription initiation site, is thought to be involved in directing RNA polymerase to begin RNA synthesis. The other upstream promoter elements determine the rate at which transcription is initiated.

Preferably, the promoter utilized by the nucleic acid construct of some embodiments of the invention is active in the specific cell population transformed—i.e. mesenchymal stem cells.

Enhancer elements can stimulate transcription up to 1,000 fold from linked homologous or heterologous promoters. Enhancers are active when placed downstream or upstream from the transcription initiation site. Many enhancer elements derived from viruses have a broad host range and are active in a variety of tissues. For example, the SV40 early gene enhancer is suitable for many cell types. Other enhancer/promoter combinations that are suitable for some embodiments of the invention include those derived from polyoma virus, human or murine cytomegalovirus (CMV), the long term repeat from various retroviruses such as murine leukemia virus, murine or Rous sarcoma virus and HIV. See, Enhancers and Eukaryotic Expression, Cold Spring Harbor Press, Cold Spring Harbor, N.Y. 1983, which is incorporated herein by reference.

In the construction of the expression vector, the promoter is preferably positioned approximately the same distance from the heterologous transcription start site as it is from the transcription start site in its natural setting. As is known in the art, however, some variation in this distance can be accommodated without loss of promoter function.

In addition to the elements already described, the expression vector of some embodiments of the invention may typically contain other specialized elements intended to increase the level of expression of cloned nucleic acids or to facilitate the identification of cells that carry the recombinant DNA. For example, a number of animal viruses contain DNA sequences that promote the extra chromosomal replication of the viral genome in permissive cell types. Plasmids bearing these viral replicons are replicated episomally as long as the appropriate factors are provided by genes either carried on the plasmid or with the genome of the host cell.

The vector may or may not include a eukaryotic replicon. If a eukaryotic replicon is present, then the vector is amplifiable in eukaryotic cells using the appropriate selectable marker. If the vector does not comprise a eukaryotic replicon, no episomal amplification is possible. Instead, the recombinant DNA integrates into the genome of the engineered cell, where the promoter directs expression of the desired nucleic acid.

Examples for mammalian expression vectors include, but are not limited to, pcDNA3, pcDNA3.1(+/−), pGL3, pZeoSV2(+/−), pSecTag2, pDisplay, pEF/myc/cyto, pCMV/myc/cyto, pCR3.1, pSinRep5, DH26S, DHBB, pNMT1, pNMT41, pNMT81, which are available from Invitrogen, pCI which is available from Promega, pMbac, pPbac, pBK-RSV and pBK-CMV which are available from Strategene, pTRES which is available from Clontech, and their derivatives.

Expression vectors containing regulatory elements from eukaryotic viruses such as retroviruses can be also used. SV40 vectors include pSVT7 and pMT2. Vectors derived from bovine papilloma virus include pBV-1MTHA, and vectors derived from Epstein Bar virus include pHEBO, and p2O5. Other exemplary vectors include pMSG, pAV009/A+, pMTO10/A+, pMAMneo-5, baculovirus pDSVE, and any other vector allowing expression of proteins under the direction of the SV-40 early promoter, SV-40 later promoter, metallothionein promoter, murine mammary tumor virus promoter, Rous sarcoma virus promoter, polyhedrin promoter, or other promoters shown effective for expression in eukaryotic cells.

As described above, viruses are very specialized infectious agents that have evolved, in many cases, to elude host defense mechanisms. Typically, viruses infect and propagate in specific cell types. The targeting specificity of viral vectors utilizes its natural specificity to specifically target predetermined cell types and thereby introduce a recombinant gene into the infected cell. Thus, the type of vector used by some embodiments of the invention will depend on the cell type transformed. The ability to select suitable vectors according to the cell type transformed is well within the capabilities of the ordinary skilled artisan and as such no general description of selection consideration is provided herein. For example, bone marrow cells can be targeted using the human T cell leukemia virus type I (HTLV-I) and kidney cells may be targeted using the heterologous promoter present in the baculovirus Autographa californica nucleopolyhedrovirus (AcMNPV) as described in Liang C Y et al., 2004 (Arch Virol. 149: 51-60).

According to one embodiment, a lentiviral vector is used to transfect the mesenchymal stem cells.

Various methods can be used to introduce the expression vector of some embodiments of the invention into mesenchymal stem cells. Such methods are generally described in Sambrook et al., Molecular Cloning: A Laboratory Manual, Cold Springs Harbor Laboratory, New York (1989, 1992), in Ausubel et al., Current Protocols in Molecular Biology, John Wiley and Sons, Baltimore, Md. (1989), Chang et al., Somatic Gene Therapy, CRC Press, Ann Arbor, Mich. (1995), Vega et al., Gene Targeting, CRC Press, Ann Arbor Mich. (1995), Vectors: A Survey of Molecular Cloning Vectors and Their Uses, Butterworths, Boston Mass. (1988) and Gilboa et at. [Biotechniques 4 (6): 504-512, 1986] and include, for example, stable or transient transfection, lipofection, electroporation and infection with recombinant viral vectors. In addition, see U.S. Pat. Nos. 5,464,764 and 5,487,992 for positive-negative selection methods.

Introduction of nucleic acids by viral infection offers several advantages over other methods such as lipofection and electroporation, since higher transfection efficiency can be obtained due to the infectious nature of viruses.

Other vectors can be used that are non-viral, such as cationic lipids, polylysine, and dendrimers.

The miRNAs, miRNA mimics and pre-miRs can be transfected into cells also using nanoparticels such as gold nanoparticles and by ferric oxide magnetic NP—see for example Ghosh et al., Biomaterials. 2013 January; 34(3): 807-16; Crew E, et al., Anal Chem. 2012 Jan. 3; 84(1):26-9. As mentioned herein above, the polynucleotides which down-regulate the miRNAs described herein above may be provided as modified polynucleotides using various methods known in the art.

Other modes of transfection that do not involved integration include the use of minicircle DNA vectors or the use of PiggyBac transposon that allows the transfection of genes that can be later removed from the genome.

As mentioned hereinabove, a variety of prokaryotic or eukaryotic cells can be used as host-expression systems to express the miRNAs or polynucleotide agent capable of down-regulating the miRNA of some embodiments of the invention. These include, but are not limited to, microorganisms, such as bacteria transformed with a recombinant bacteriophage DNA, plasmid DNA or cosmid DNA expression vector containing the coding sequence; yeast transformed with recombinant yeast expression vectors containing the coding sequence; plant cell systems infected with recombinant virus expression vectors (e.g., cauliflower mosaic virus, CaMV; tobacco mosaic virus, TMV) or transformed with recombinant plasmid expression vectors, such as Ti plasmid, containing the coding sequence. Mammalian expression systems can also be used to express the miRNAs of some embodiments of the invention.

Examples of bacterial constructs include the pET series of E. coli expression vectors [Studier et al. (1990) Methods in Enzymol. 185:60-89).

In yeast, a number of vectors containing constitutive or inducible promoters can be used, as disclosed in U.S. Pat. No. 5,932,447. Alternatively, vectors can be used which promote integration of foreign DNA sequences into the yeast chromosome.

The conditions used for contacting the mesenchymal stem cells are selected for a time period/concentration of cells/concentration of miRNA/ratio between cells and miRNA which enable the miRNA (or inhibitors thereof) to induce differentiation thereof. The present invention further contemplates incubation of the mesenchymal stem cells with a differentiation factor which promotes differentiation towards an astrocytic lineage. The incubation with such differentiation factors may be affected prior to, concomitant with or following the contacting with the miRNA. According to this embodiment the medium may be supplemented with at least one of SHH (e.g. about 250 ng/ml), FGFb (e.g. 50 ng/ml), EGF (e.g. about 50 ng/ml), a cAMP inducer (e.g. IBMX or dbcycAMP), PDGF (e.g. about 5 ng/ml) neuregulin (e.g. about 50 ng/ml) and FGFb (e.g. about 20 ng/ml).

Alternatively, or additionally, the mesenchymal stem cells may be genetically modified so as to express such differentiation factors, using expression constructs such as those described herein above.

During or following the differentiation step the mesenchymal stem cells may be monitored for their differentiation state. Cell differentiation can be determined upon examination of cell or tissue-specific markers which are known to be indicative of differentiation. For example, the differentiated cells may express the following markers: S100 beta, glial fibrillary acidic protein (GFAP), glutamine synthetase, GLT-1, Excitatory Amino Acid Transporter 1 (EAAT1) and Excitatory Amino Acid Transporter 2 (EAAT2). Further, the differentiated cells may secrete a neurotrophic factor including for example glial derived neurotrophic factor (GDNF), GenBank accession nos. L19063, L15306; nerve growth factor (NGF), GenBank accession no. CAA37703; brain-derived neurotrophic factor (BDNF), GenBank accession no CAA62632; neurotrophin-3 (NT-3), GenBank Accession No. M37763; neurotrophin-4/5; Neurturin (NTN), GenBank Accession No. NP_004549; Neurotrophin-4, GenBank Accession No. M86528; Persephin, GenBank accession no. AAC39640; brain derived neurotrophic factor, (BDNF), GenBank accession no. CAA42761; artemin (ART), GenBank accession no. AAD13110; ciliary neurotrophic factor (CNTF), GenBank accession no. NP_000605; insulin growth factor-I (IGF-1), GenBank accession no. NP_000609; and/or Neublastin GenBank accession no. AAD21075.

It will be appreciated that the differentiation time may be selected so as to obtain early progenitors of astrocytes or more mature astrocytes. Enrichment for a particular early or mature astrocytic cell is also contemplated. Selection for cells which express markers such as CD44, A2B5 and S100 allows for the enrichment of progenitor type astrocytes, whereas selection for cells which express markers such as GFAP and glutamine synthase allows for selection of mature astrocytes.

Tissue/cell specific markers can be detected using immunological techniques well known in the art [Thomson J A et al., (1998). Science 282: 1145-7]. Examples include, but are not limited to, flow cytometry for membrane-bound markers, immunohistochemistry for extracellular and intracellular markers and enzymatic immunoassay, for secreted molecular markers.

In addition, cell differentiation can be also followed by specific reporters that are tagged with GFP or RFP and exhibit increased fluorescence upon differentiation.

Isolated cell populations obtained according to the methods describe herein are typically non-homogeneous, although homogeneous cell populations are also contemplated.

According to a particular embodiment, the cell populations are genetically modified to express a miRNA or a polynucleotide agent capable of down-regulating the miRNA.

The term "isolated" as used herein refers to a population of cells that has been removed from its in-vivo location (e.g. bone marrow, neural tissue). Preferably the isolated cell population is substantially free from other substances (e.g., other cells) that are present in its in-vivo location.

Cell populations may be selected such that more than about 50% of the cells express at least one, at least two, at least three, at least four, at least five or all of the following markers: S100 beta, glial fibrillary acidic protein (GFAP), glutamine sythetase, GLT-1, GDNF, BDNF, IGF-1 and GLAST.

Cell populations may be selected such that more than about 60% of the cells express at least one, at least two, at least three, at least four, at least five or all of the following markers: S100 beta, glial fibrillary acidic protein (GFAP), glutamine sythetase, GLT-1, GDNF, BDNF, IGF-1 and GLAST.

Cell populations may be selected such that more than about 70% of the cells express at least one, at least two, at least three, at least four, at least five or all of the following markers: S100 beta, glial fibrillary acidic protein (GFAP), glutamine sythetase, GLT-1, GDNF, BDNF, IGF-1 and GLAST.

Cell populations may be selected such that more than about 80% of the cells express at least one, at least two, at least three, at least four, at least five or all of the following markers: S100 beta, glial fibrillary acidic protein (GFAP), glutamine sythetase, GLT-1, GDNF, BDNF, IGF-1 and GLAST.

Cell populations may be selected such that more than about 90% of the cells express at least one, at least two, at least three, at least four, at least five or all of the following markers: S100 beta, glial fibrillary acidic protein (GFAP), glutamine sythetase, GLT-1, GDNF, BDNF, IGF-1 and GLAST.

Cell populations may be selected such that more than about 95% of the cells express at least one, at least two, at least three, at least four, at least five or all of the following markers: S100 beta, glial fibrillary acidic protein (GFAP), glutamine sythetase, GLT-1, GDNF, BDNF, IGF-1 and GLAST.

Isolation of particular subpopulations of cells may be effected using techniques known in the art including fluorescent activated cell sorting and/or magnetic separation of cells.

The cells of the populations of this aspect of the present invention may comprise structural astrocytic phenotypes including a cell size, a cell shape, an organelle size and an organelle number. Thus, mature astrocytic structural phenotypes include a round nucleus, a "star shaped" body and many long processes that end as vascular foot plates on the small blood vessels of the CNS.

These structural phenotypes may be analyzed using microscopic techniques (e.g. scanning electron microscopy). Antibodies or dyes may be used to highlight distinguishing features in order to aid in the analysis.

The present inventors have further shown that a particular miRNA (miRNA 504) which is upregulated on differentiation of MSCs towards an astrocytic phenotype targets α-Synuclein (see FIG. 10). Mutations within the α-Synuclein gene are associated with autosomal dominant familial PD.

Thus, the present inventors further propose use of MSCs as a cargo cell to transport miRNA 504 to the brain where the miRNA then targets the α-Synuclein as a treatment for Parkinson's.

Another miRNA (miRNA 152) which is upregulated on differentiation of MSCs towards an astrocytic phenotype targets Huntingdon (HTT) gene. Mutations within this gene are associated with Huntingdon disease (HD).

Thus, the present inventors further propose use of MSCs as a cargo cell to transport miRNA 152 to the brain where the miRNA then targets the α-Synuclein as a treatment for Huntingdon's disease.

Another miRNA (miRNA 665) which is upregulated on differentiation of MSCs towards an astrocytic phenotype targets the prion gene (PRNP). Thus, the present inventors further propose use of MSCs as a cargo cell to transport miRNA 665 to the brain where the miRNA then targets PRNP.

Another miRNA (miRNA 340) which is upregulated on differentiation of MSCs towards an astrocytic phenotype targets SOD1 gene. Mutations within this gene are associated with ALS.

Thus, the present inventors further propose use of MSCs as a cargo cell to transport miRNA 340 to the brain where the miRNA then targets the SOD1 gene as a treatment for ALS.

According to this aspect of the invention, the MSCs may be manipulated to express the miRNA (or mimic thereof) and cultured so that they differentiate towards the astrocytic phenotype as described herein above. Alternatively, the MSCs may be manipulated to express the miRNA (or mimic thereof) and administered to the patient (e.g. a patient with Parkinson's) without allowing for astrocytic differentiation.

The cells and cell populations of the present invention may be useful for a variety of therapeutic purposes. Representative examples of CNS diseases or disorders that can be beneficially treated with the cells described herein include, but are not limited to, a pain disorder, a motion disorder, a dissociative disorder, a mood disorder, an affective disorder, a neurodegenerative disease or disorder and a convulsive disorder.

More specific examples of such conditions include, but are not limited to, Parkinson's, ALS, Multiple Sclerosis, Huntingdon's disease, autoimmune encephalomyelitis, diabetic neuropathy, glaucatomus neuropathy, macular degeneration, action tremors and tardive dyskinesia, panic, anxiety, depression, alcoholism, insomnia, manic behavior, Alzheimer's and epilepsy.

The use of differentiated MSCs may be also indicated for treatment of traumatic lesions of the nervous system including spinal cord injury and also for treatment of stroke caused by bleeding or thrombosis or embolism because of the need to induce neurogenesis and provide survival factors to minimize insult to damaged neurons.

In any of the methods described herein the cells may be obtained from an autologous, semi-autologous or non-autologous (i.e., allogeneic or xenogeneic) human donor or embryo or cord/placenta. For example, cells may be isolated from a human cadaver or a donor subject.

The term semi-autologous refers to donor cells which are partially-mismatched to recipient cells at a major histocompatibility complex (MHC) class I or class II locus.

The cells of the present invention can be administered to the treated individual using a variety of transplantation approaches, the nature of which depends on the site of implantation.

The term or phrase "transplantation", "cell replacement" or "grafting" are used interchangeably herein and refer to the introduction of the cells of the present invention to target tissue. As mentioned, the cells can be derived from the recipient or from an allogeneic, semi-allogeneic or xenogeneic donor.

The cells can be injected systemically into the circulation, administered intrathecally or grafted into the central nervous system, the spinal cord or into the ventricular cavities or subdurally onto the surface of a host brain. Conditions for successful transplantation include: (i) viability of the implant; (ii) retention of the graft at the site of transplantation; and (iii) minimum amount of pathological reaction at the site of transplantation. Methods for transplanting various nerve tissues, for example embryonic brain tissue, into host brains have been described in: "Neural grafting in the mammalian CNS", Bjorklund and Stenevi, eds. (1985); Freed et al., 2001; Olanow et al., 2003). These procedures include intraparenchymal transplantation, i.e. within the host brain (as compared to outside the brain or extraparenchymal transplantation) achieved by injection or deposition of tissue within the brain parenchyma at the time of transplantation.

Intraparenchymal transplantation can be performed using two approaches: (i) injection of cells into the host brain parenchyma or (ii) preparing a cavity by surgical means to expose the host brain parenchyma and then depositing the graft into the cavity.

Both methods provide parenchymal deposition between the graft and host brain tissue at the time of grafting, and both facilitate anatomical integration between the graft and host brain tissue. This is of importance if it is required that the graft becomes an integral part of the host brain and survives for the life of the host.

Alternatively, the graft may be placed in a ventricle, e.g. a cerebral ventricle or subdurally, i.e. on the surface of the host brain where it is separated from the host brain parenchyma by the intervening pia mater or arachnoid and pia mater. Grafting to the ventricle may be accomplished by injection of the donor cells or by growing the cells in a substrate such as 3% collagen to form a plug of solid tissue which may then be implanted into the ventricle to prevent dislocation of the graft. For subdural grafting, the cells may be injected around the surface of the brain after making a slit in the dura.

Injections into selected regions of the host brain may be made by drilling a hole and piercing the dura to permit the needle of a microsyringe to be inserted. The microsyringe is preferably mounted in a stereotaxic frame and three dimensional stereotaxic coordinates are selected for placing the needle into the desired location of the brain or spinal cord. The cells may also be introduced into the putamen, nucleus basalis, hippocampus cortex, striatum, substantia nigra or caudate regions of the brain, as well as the spinal cord.

The cells may also be transplanted to a healthy region of the tissue. In some cases the exact location of the damaged tissue area may be unknown and the cells may be inadvertently transplanted to a healthy region. In other cases, it may be preferable to administer the cells to a healthy region, thereby avoiding any further damage to that region. Whatever the case, following transplantation, the cells preferably migrate to the damaged area.

For transplanting, the cell suspension is drawn up into the syringe and administered to anesthetized transplantation recipients. Multiple injections may be made using this procedure.

The cellular suspension procedure thus permits grafting of the cells to any predetermined site in the brain or spinal cord, is relatively non-traumatic, allows multiple grafting simultaneously in several different sites or the same site using the same cell suspension, and permits mixtures of cells from different anatomical regions.

Multiple grafts may consist of a mixture of cell types, and/or a mixture of transgenes inserted into the cells. Preferably from approximately $10^4$ to approximately $10^9$ cells are introduced per graft. Cells can be administered concomitantly to different locations such as combined administration intrathecally and intravenously to maximize the chance of targeting into affected areas.

For transplantation into cavities, which may be preferred for spinal cord grafting, tissue is removed from regions close to the external surface of the central nerve system (CNS) to form a transplantation cavity, for example as described by Stenevi et al. (Brain Res. 114:1-20, 1976), by removing bone overlying the brain and stopping bleeding with a material such a gelfoam. Suction may be used to create the cavity. The graft is then placed in the cavity. More than one transplant may be placed in the same cavity using injection of cells or solid tissue implants. Preferably, the site of implantation is dictated by the CNS disorder being treated. Demyelinated MS lesions are distributed across multiple locations throughout the CNS, such that effective treatment of MS may rely more on the migratory ability of the cells to the appropriate target sites.

Intranasal administration of the cells described herein is also contemplated.

MSCs typically down regulate MHC class 2 and are therefore less immunogenic. Embryonal or newborn cells obtained from the cord blood, cord's Warton's gelly or placenta are further less likely to be strongly immunogenic and therefore less likely to be rejected, especially since such cells are immunosuppressive and immunoregulatory to start with.

Notwithstanding, since non-autologous cells may induce an immune reaction when administered to the body several approaches have been developed to reduce the likelihood of rejection of non-autologous cells. Furthermore, since diseases such as multiple sclerosis are inflammatory based diseases, the problem of immune reaction is exacerbated. These include either administration of cells to privileged sites, or alternatively, suppressing the recipient's immune system, providing anti-inflammatory treatment which may be indicated to control autoimmune disorders to start with and/or encapsulating the non-autologous/semi-autologous cells in immunoisolating, semipermeable membranes before transplantation.

As mentioned herein above, the present inventors also propose use of newborn mesenchymal stem cells to limit the immune reaction.

The following experiments may be performed to confirm the potential use of newborn's MSCs isolated from the cord/placenta for treatment of neurological disorders:

1) Differentiated MSCs (to various neural cells or neural progenitor cells) may serve as stimulators in one way mixed lymphocyte culture with allogeneic T cells and proliferative responses in comparison with T cells responding against allogeneic lymphocytes isolated from the same donor may be evaluated by $^3$H-Thymidine uptake to document hyporesponsiveness.
2) Differentiated MSCs may be added/co-cultured to one way mixed lymphocyte cultures and to cell cultures with T cell mitogens (phytohemmaglutinin and concanavalin A) to confirm the immunosuppressive effects on proliferative responses mediated by T cells.
3) Cord and placenta cells cultured from Brown Norway rats (unmodified and differentiated), may be enriched for MSCs and these cells may be infused into Lewis rats with induced experimental autoimmune encephalomyelitis (EAE). Alternatively, cord and placenta cells cultured from BALB/c mice, (BALB/cxC57BL/6)F1 or xenogeneic cells from Brown Norway rats (unmodified and differentiated), may be enriched for MSCs and these cells may be infused into C57BL/6 or SJL/j recipients with induced experimental autoimmune encephalomyelitis (EAE). The clinical effects against paralysis may be investigated to evaluate the therapeutic effects of xenogeneic, fully MHC mismatched or haploidentically mismatched MSCs. Such experiments may provide the basis for treatment of patients with a genetic disorder or genetically proned disorder with family member's haploidentical MSCs.
4) BALB/c MSCs cultured from cord and placenta may be transfused with pre-miR labeled with GFP or RFP, which will allow the inventors to follow the migration and persistence of these cells in the brain of C57BL/6 recipients with induced EAE. The clinical effects of labeled MHC mismatched differentiated MSCs may be evaluated by monitoring signs of disease, paralysis and histopathology. The migration and localization of such cells may be also monitored by using fluorescent cells from genetically transduced GFP "green" or Red2 "red" donors.

As mentioned, the present invention also contemplates encapsulation techniques to minimize an immune response.

Encapsulation techniques are generally classified as microencapsulation, involving small spherical vehicles and macroencapsulation, involving larger flat-sheet and hollow-fiber membranes (Uludag, H. et al. Technology of mammalian cell encapsulation. Adv Drug Deliv Rev. 2000; 42: 29-64).

Methods of preparing microcapsules are known in the arts and include for example those disclosed by Lu M Z, et al., Cell encapsulation with alginate and alpha-phenoxycinnamylidene-acetylated poly(allylamine). Biotechnol Bioeng. 2000, 70: 479-83, Chang T M and Prakash S. Procedures for microencapsulation of enzymes, cells and genetically engineered microorganisms. Mol. Biotechnol. 2001, 17: 249-60, and Lu M Z, et al., A novel cell encapsulation method using photosensitive poly(allylamine alpha-cyanocinnamylideneacetate). J. Microencapsul. 2000, 17: 245-51.

For example, microcapsules are prepared by complexing modified collagen with a ter-polymer shell of 2-hydroxyethyl methylacrylate (HEMA), methacrylic acid (MAA) and methyl methacrylate (MMA), resulting in a capsule thickness of 2-5 .mu.m.

Such microcapsules can be further encapsulated with additional 2-5 .mu.m ter-polymer shells in order to impart a negatively charged smooth surface and to minimize plasma protein absorption (Chia, S. M. et al. Multi-layered microcapsules for cell encapsulation Biomaterials. 2002 23: 849-56).

Other microcapsules are based on alginate, a marine polysaccharide (Sambanis, A. Encapsulated islets in diabetes treatment. Diabetes Technol. Ther. 2003, 5: 665-8) or its derivatives. For example, microcapsules can be prepared by the polyelectrolyte complexation between the polyanions sodium alginate and sodium cellulose sulphate with the polycation poly(methylene-co-guanidine) hydrochloride in the presence of calcium chloride.

It will be appreciated that cell encapsulation is improved when smaller capsules are used. Thus, the quality control, mechanical stability, diffusion properties, and in vitro activities of encapsulated cells improved when the capsule size was reduced from 1 mm to 400 .mu.m (Canaple L. et al, Improving cell encapsulation through size control. J Biomater Sci Polym Ed. 2002; 13:783-96). Moreover, nanoporous biocapsules with well-controlled pore size as small as 7 nm, tailored surface chemistries and precise microarchitectures were found to successfully immunoisolate microenvironments for cells (Williams D. Small is beautiful: microparticle and nanoparticle technology in medical devices. Med Device Technol. 1999, 10: 6-9; Desai, T. A. Microfabrication technology for pancreatic cell encapsulation. Expert Opin Biol Ther. 2002, 2: 633-46).

Examples of immunosuppressive agents include, but are not limited to, methotrexate, cyclophosphamide, cyclosporine, cyclosporin A, chloroquine, hydroxychloroquine, sulfasalazine (sulphasalazopyrine), gold salts, D-penicillamine, leflunomide, azathioprine, anakinra, infliximab (REMICADE™), etanercept, TNF alpha blockers, a biological agent that targets an inflammatory cytokine, and Non-Steroidal Anti-Inflammatory Drug (NSAIDs). Examples of NSAIDs include, but are not limited to acetyl salicylic acid, choline magnesium salicylate, diflunisal, magnesium salicylate, salsalate, sodium salicylate, diclofenac, etodolac, fenoprofen, flurbiprofen, indomethacin, ketoprofen, ketorolac, meclofenamate, naproxen, nabumetone, phenylbutazone, piroxicam, sulindac, tolmetin, acetaminophen, ibuprofen, Cox-2 inhibitors and tramadol.

In any of the methods described herein, the cells can be administered either per se or, preferably as a part of a pharmaceutical composition that further comprises a pharmaceutically acceptable carrier.

As used herein a "pharmaceutical composition" refers to a preparation of one or more of the cell compositions described herein, with other chemical components such as pharmaceutically suitable carriers and excipients. The purpose of a pharmaceutical composition is to facilitate administration of the cells to a subject.

Hereinafter, the term "pharmaceutically acceptable carrier" refers to a carrier or a diluent that does not cause significant irritation to a subject and does not abrogate the biological activity and properties of the administered compound. Examples, without limitations, of carriers are propylene glycol, saline, emulsions and mixtures of organic solvents with water.

Herein the term "excipient" refers to an inert substance added to a pharmaceutical composition to further facilitate administration of a compound.

Examples, without limitation, of excipients include calcium carbonate, calcium phosphate, various sugars and types of starch, cellulose derivatives, gelatin, vegetable oils and polyethylene glycols.

Techniques for formulation and administration of drugs may be found in "Remington's Pharmaceutical Sciences," Mack Publishing Co., Easton, Pa., latest edition, which is incorporated herein by reference.

Suitable routes of administration include direct administration into the circulation (intravenously or intra-arterial), into the spinal fluid or into the tissue or organ of interest. Thus, for example the cells may be administered directly into the brain.

For any preparation used in the methods of the invention, the therapeutically effective amount or dose can be estimated initially from in vitro and cell culture assays.

Preferably, a dose is formulated in an animal model to achieve a desired concentration or titer. Such information can be used to more accurately determine useful doses in humans.

Toxicity and therapeutic efficacy of the active ingredients described herein can be determined by standard pharmaceutical procedures in vitro, in cell cultures or experimental animals. For example, animal models of demyelinating diseases include shiverer (shi/shi, MBP deleted) mouse, MD rats (PLP deficiency), Jimpy mouse (PLP mutation), dog shaking pup (PLP mutation), twitcher mouse (galactosylceramidase defect, as in human Krabbe disease), trembler mouse (PMP-22 deficiency). Virus induced demyelination model comprise use if Theiler's virus and mouse hepatitis virus.

Autoimmune EAE is a possible model for multiple sclerosis.

The data obtained from these in vitro and cell culture assays and animal studies can be used in formulating a range of dosage for use in human. The dosage may vary depending upon the dosage form employed and the route of administration utilized. The exact formulation, route of administration and dosage can be chosen by the individual physician in view of the patient's condition, (see e.g., Fingl, et al., 1975, in "The Pharmacological Basis of Therapeutics", Ch. 1 p. 1). For example, a multiple sclerosis patient can be monitored symptomatically for improved motor functions indicating positive response to treatment.

For injection, the active ingredients of the pharmaceutical composition may be formulated in aqueous solutions, preferably in physiologically compatible buffers such as Hank's solution, Ringer's solution, or physiological salt buffer.

Dosage amount and interval may be adjusted individually to levels of the active ingredient which are sufficient to effectively treat the brain disease/disorder. Dosages necessary to achieve the desired effect will depend on individual characteristics and route of administration. Detection assays can be used to determine plasma concentrations.

Depending on the severity and responsiveness of the condition to be treated, dosing can be of a single or a plurality of administrations, with course of treatment lasting from several days to several weeks or diminution of the disease state is achieved.

The amount of a composition to be administered will, of course, be dependent on the individual being treated, the severity of the affliction, the manner of administration, the judgment of the prescribing physician, etc. The dosage and timing of administration will be responsive to a careful and continuous monitoring of the individual changing condition. For example, a treated multiple sclerosis patient will be administered with an amount of cells which is sufficient to alleviate the symptoms of the disease, based on the monitoring indications.

The cells of the present invention may be co-administered with therapeutic agents useful in treating neurodegenerative disorders, such as gangliosides; antibiotics, neurotransmitters, neurohormones, toxins, neurite promoting molecules; and antimetabolites and precursors of neurotransmitter molecules such as L-DOPA.

As used herein the term "about" refers to +/−10%.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Various embodiments and aspects of the present invention as delineated hereinabove and as claimed in the claims section below find experimental support in the following examples.

As used herein the term "about" refers to ±10%.

The terms "comprises", "comprising", "includes", "including", "having" and their conjugates mean "including but not limited to".

The term "consisting of" means "including and limited to".

The term "consisting essentially of" means that the composition, method or structure may include additional ingredients, steps and/or parts, but only if the additional ingredients, steps and/or parts do not materially alter the basic and novel characteristics of the claimed composition, method or structure.

As used herein, the singular form "a", "an" and "the" include plural references unless the context clearly dictates otherwise. For example, the term "a compound" or "at least one compound" may include a plurality of compounds, including mixtures thereof.

Throughout this application, various embodiments of this invention may be presented in a range format. It should be understood that the description in range format is merely for convenience and brevity and should not be construed as an inflexible limitation on the scope of the invention. Accordingly, the description of a range should be considered to have specifically disclosed all the possible subranges as well as individual numerical values within that range. For example, description of a range such as from 1 to 6 should be considered to have specifically disclosed subranges such as from 1 to 3, from 1 to 4, from 1 to 5, from 2 to 4, from 2 to 6, from 3 to 6 etc., as well as individual numbers within that range, for example, 1, 2, 3, 4, 5, and 6. This applies regardless of the breadth of the range.

Whenever a numerical range is indicated herein, it is meant to include any cited numeral (fractional or integral) within the indicated range. The phrases "ranging/ranges between" a first indicate number and a second indicate number and "ranging/ranges from" a first indicate number "to" a second indicate number are used herein interchangeably and are meant to include the first and second indicated numbers and all the fractional and integral numerals therebetween.

As used herein the term "method" refers to manners, means, techniques and procedures for accomplishing a given task including, but not limited to, those manners, means, techniques and procedures either known to, or readily developed from known manners, means, techniques and procedures by practitioners of the chemical, pharmacological, biological, biochemical and medical arts.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

It is noted that for each miR described herein the corresponding sequence (mature and pre) is provided in the sequence listing which should be regarded as part of the specification.

Various embodiments and aspects of the present invention as delineated hereinabove and as claimed in the claims section below find experimental support in the following examples.

EXAMPLES

Reference is now made to the following examples, which together with the above descriptions illustrate some embodiments of the invention in a non limiting fashion.

Generally, the nomenclature used herein and the laboratory procedures utilized in the present invention include molecular, biochemical, microbiological and recombinant DNA techniques. Such techniques are thoroughly explained in the literature. See, for example, "Molecular Cloning: A laboratory Manual" Sambrook et al., (1989); "Current Protocols in Molecular Biology" Volumes I-III Ausubel, R. M., ed. (1994); Ausubel et al., "Current Protocols in Molecular Biology", John Wiley and Sons, Baltimore, Md. (1989); Perbal, "A Practical Guide to Molecular Cloning", John Wiley & Sons, New York (1988); Watson et al., "Recombinant DNA", Scientific American Books, New York; Birren et al. (eds) "Genome Analysis: A Laboratory Manual Series", Vols. 1-4, Cold Spring Harbor Laboratory Press, New York (1998); methodologies as set forth in U.S. Pat. Nos. 4,666,828; 4,683,202; 4,801,531; 5,192,659 and 5,272,057; "Cell Biology: A Laboratory Handbook", Volumes I-III Cellis, J. E., ed. (1994); "Culture of Animal Cells—A Manual of Basic Technique" by Freshney, Wiley-Liss, N. Y. (1994), Third Edition; "Current Protocols in Immunology" Volumes I-III Coligan J. E., ed. (1994); Stites et al. (eds), "Basic and Clinical Immunology" (8th Edition), Appleton & Lange, Norwalk, Conn. (1994); Mishell and Shiigi (eds), "Selected Methods in Cellular Immunology", W. H. Freeman and Co., New York (1980); available immunoassays are extensively described in the patent and scientific literature, see, for example, U.S. Pat. Nos. 3,791,932; 3,839,153; 3,850,752; 3,850,578; 3,853,987; 3,867,517; 3,879,262; 3,901,654; 3,935,074; 3,984,533; 3,996,345; 4,034,074; 4,098,876; 4,879,219; 5,011,771 and 5,281,521; "Oligonucleotide Synthesis" Gait, M. J., ed. (1984); "Nucleic Acid Hybridization" Hames, B. D., and Higgins S. J., eds. (1985); "Transcription and Translation" Hames, B. D., and Higgins S. J., eds. (1984); "Animal Cell Culture" Freshney, R. I., ed. (1986); "Immobilized Cells and Enzymes" IRL Press, (1986); "A Practical Guide to Molecular Cloning" Perbal, B., (1984) and "Methods in Enzymology" Vol. 1-317, Academic Press; "PCR Protocols: A Guide To Methods And Applications", Academic Press, San Diego, Calif. (1990); Marshak et al., "Strategies for Protein Purification and Characterization—A Laboratory Course Manual" CSHL Press (1996); all of which are incorporated by reference as if fully set forth herein. Other general references are provided throughout this document. The procedures therein are believed to be well known in the art and are provided for the convenience of the reader. All the information contained therein is incorporated herein by reference.

Example 1

Soluble Factors for the Differentiation of MSCs Towards an Astrocytic Phenotype

Materials and Methods

Differentiation of MSCs to Cells Expressing Astrocytic Phenotypes:

MSCs from the four different sources (bone marrow (BM-MSCs), adipose-derived (AD-MSCs), cord and placenta-derived cells) were employed in these studies. The cells were plated first in DMEM+10% FCS for 1 day and were then transferred for 5 days to NM media containing SHH 250 ng/ml, FGFb (50 ng/ml) and EGF 50 ng/ml. The cells were incubated for an additional 10 days with IBMX (0.5 mM), dbcycAMP (1 mM), PDGF (5 ng/ml) neuregulin (50 ng/ml) and FGFb (20 ng/ml). In the last stage, the cells were incubated for 5 days in G5 media supplemented with the same factors.

The differentiated cells were analyzed for the following markers:

Nestin, Olig2, β-III tubulin, GFAP, glutamine synthase.

Results

Figure 1:
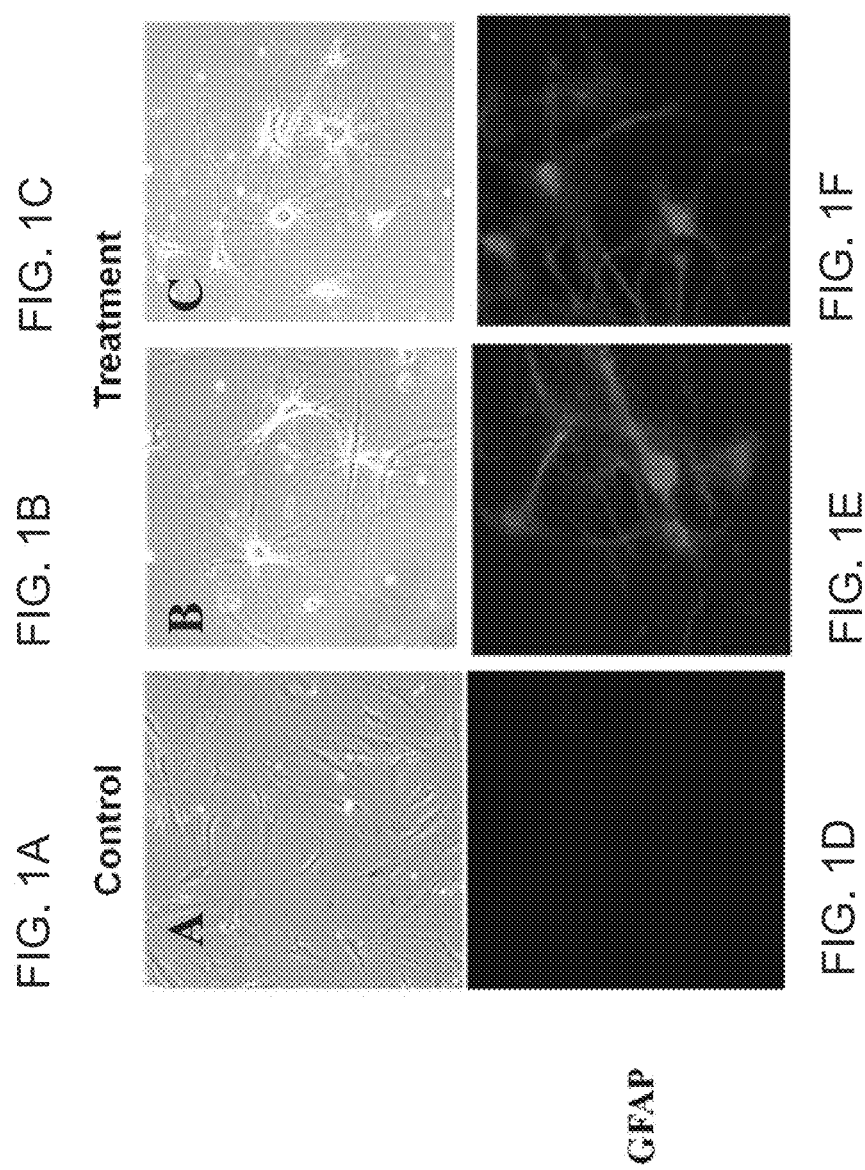

Using the above described differentiation protocols, both BM-MSC (FIG. 1) and the other MSC types (data not shown) exhibited astrocytic morphology and were stained positive for the astrocytic marker GFAP (FIG. 1).

The present inventors further analyzed the differentiated cells and found that they expressed mRNA of GFAP and S100 as well as the glutamate transporters, as shown in FIGS. 2 and 3.

Example 2 miRNAs for the Differentiation of MSCs into Astrocytes

Materials and Methods miRNA Microarray Analysis:

For analyzing the differential expression of specific miRNA in control and differentiated MSCs, the Stem cell microRNA qPCR array was used, with quantiMiR from SBI company (catalog # RA620A-1).

The system allows for the ability to quantitate fold differences of 95 separate microRNAs between 2 separate experimental RNA samples. The array plate also includes the U6 transcript as a normalization signal. All 95 microRNAs chosen for the array have published implications with regard to potential roles in stem cell self-renewal, hematopoiesis, neuronal development and differentiated tissue identification.

Total RNA was isolated from $10^5$-$10^6$ cells of control and differentiated MSCs using miRneasy total RNA isolation kit from Qiagen (catalog #217004) that isolate RNA fraction with sizes <200 bp.

500 ng of total RNA was processed according to "SBI Stem Cell MicroRNA qPCR Array with QuantiMir™" (Cat. # RA620A-1) user protocol, the contents of which are incorporated herein by reference. For the qPCR, the Applied Biosystems Power SYBR master mix (cat#4367659) was used.

For validation, sybr-green qPCR of the specific miRNA of interest was performed on the same RNA samples processed according to QIAGEN miScript System handbook (cat #218061 & 218073).

Hu hsa-miR MicroRNA Profiling Kit (System Biosciences) "SBI Stem Cell MicroRNA qPCR Array with QuantiMir™" (Cat. # RA620A-1) which detects the expression of 96 miRNAs, was used to profile the miRNAs in unmodified BM-MSC compared with MSCs differentiated to astrocytes. 500 ng of total RNA was tagged with poly(A) to its 3' end by poly A polymerase, and reverse-transcribed with oligo-dT adaptors by QuantiMir RT technology. Expression levels of the miRNAs were measured by quantitative PCR using SYBR green reagent and VIIA7, Real-Time PCR System (Applied Biosystems). All miRNAs could be measured with miRNA specific forward primers and a universal reverse primer (SBI). Expression level of the miRNAs was normalized to U6 snRNA, using the comparative CT method for relative quantification as calculated with the following equation: $2^{-[(CT\ astrocyte\ diff\ miRNA - CT\ astrocyte\ endogenous\ control) - (CT\ DMEM\ miRNA - CT\ DMEM\ endogenous\ control)]}$.

Results

To identify miRNAs that may be involved in the differentiation of MSCs into astrocytes, the miRNA signature of control unmodified MSCs was compared to MSCs differentiated into astrocytes.

A qRT-PCR microarray was analyzed that contained 96 miRNAs, all of which were related to stem cells and that were divided into subgroups based on their known association with stem cells, neural-related, hematopoietic and organ-related miRNAs.

As presented in FIGS. 4-7, there were significant changes in the expression of specific miRNA of each group between the control MSCs and the differentiated ones.

qRT-PCR studies were then performed to validate the differences in the miRNA expression that were observed between the control and differentiated cells.

Similar to the results that were obtained with the microarray data, qRT-PCR it was found that the differentiated MSCs demonstrated a decrease in miRs, 32, 133, 221, 145, 302a and 302b and an increase in miRs 9, 20b, 101, 141, 146a and 146b.

The role of specific miRNAs in the astrocytic differentiation of the cells was further examined. It was found that the combination of miR-9 and miR-20b as well as combination of miR-20b, 101 and 146a also increased GFAP expression. Similarly, it was found that inhibiting miR-10b and miR-302 and expressing miR-9, 146 and 101 also increased GFAP expression (data not shown).

Example 3

Identification of Additional miRNAs for the Differentiation of MSCs into an Astrocytic Phenotype Materials and Methods Bone marrow mesenchymal stem cells (BM-MSCs) were transduced with a GFAP-GFP reporter. The cells were then transfected with both antagomiR-138 and miR-101. The cells were viewed under a fluorescence microscope after 10 days.

Additional gene and miR arrays were used to characterize the differentiated cells.

Results

As illustrated in FIGS. 9A-B, silencing of miR-138 together with overexpression of miR-101 leads to the differentiation of MSCs into GFAP positive cells. In addition, these cells also expressed high levels of the glutamate transporters (data not shown).

miR array analysis identified the following miRs that were increased in the differentiated cells: miR-504, miR-891 and miR-874; and the following miRs that were decreased in the differentiated cells: miR-138, miR-182, miR-487, miR-214 and miR-409. Gene array analysis of the differentiated astrocytes demonstrated a decrease in a variety of genes related to osteogenic, adipogenic and chondrogenic differentiation and an increased expression of neural markers. Similarly, it was found that the differentiated astrocytes expressed high levels of NGF, IGF-1, VEGF, BDNF and GDNF. In addition, they expressed high levels of CXCR4, chemokines and IL-8 that play a role in cell migration.

Further miR array results are provided in Table 1 and Table 2 herein below.

Table 1 is a list of additional miRNAs that are up-regulated (over three fold) on differentiation of MSCs to astrocytes as described in Example 1, materials and methods as compared to non-differentiated MSCs. Table 2 is a list of additional miRNAs that are down-regulated (over three fold) on differentiation of MSCs to astrocytes as described in Example 1, materials and methods as compared to non-differentiated MSCs.

TABLE 1 miR-92ap, miR-21, miR-26a, miR-18a, miR-124, miR-99a, miR-30c, miR-301a, miR-145-50, miR-143-3p, miR-373, miR-20b, miR-29c, miR-29b, miR-143, let-7g, let-7a, let-7b, miR-98, miR-30a*, miR-17, miR-1, miR-192, miR-155, miR-516-ap, miR-31, miR-181a, miR-181b, miR-181c, miR-34-c, miR-34b*, miR-103a, miR-210, miR-16, miR-30a, miR-31, miR-222, miR-17, miR-17*, miR-200b, miR-200c, miR-128, miR-503, miR-424, miR-195, miR-1256, miR-203a, miR-199, miR-93, miR-98, miR-125-a, miR-133a, miR-133b, miR-126, miR-194, miR-346, miR-15b, miR-338-3p, miR-373, miR-205, miR-210, miR-125, miR-1226, miR-708, miR-449, miR-422, miR-340, miR-605, miR-522, miR-663, miR-130a, miR-130b, miR-942, miR-572, miR-520, miR-639, miR-654, miR-519, mir-202, mir-767-5p, mir-29a, mir-29b, mir-29c, let-7a, let-7b, let-7c, let-7d, let-7e, let-7f, let-7g, let-7i, mir-4458, mir-4500, mir-98, mir-148a, mir-148b, mir-152, mir-4658, mir-3662, mir-25, mir-32, mir-363, mir-367, mir-92a, mir-92b, mir-520d-5p, mir-524-5p, mir-4724-3p, mir-1294, mir-143, mir-4770, mir-3659, mir-145, mir-3163, mir-181a, mir-181b, mir-181c, mir-181d, mir-4262, mir-4279, mir-144, mir-642b, mir-4742-3p, mir-3177-5p, mir-656, mir-3121-3p, mir-106a, mir-106b, mir-17, mir-20a, mir-20b, mir-519d, mir-93, mir-1297, mir-26a, mir-26b, mir-4465, mir-326, mir-330-5p, mir-3927 and mir-2113.

TABLE 2 miR-204, miR-224, miR-616, miR-122, miR-299, miR-100, miR-138, miR-140, miR-375, miR-217, miR-302, miR-372, miR-96, miR-127-3p, miR-449, miR-135b, miR-101, miR-326, miR-324, miR-335, miR-14, miR-16, mir-410, mir-3163, mir-148a, mir-148b, mir-152, mir-3121-3p, mir-495, mir-203, mir-4680-3p.

Example 4

Down-Regulation of a Synuclein in MSC Using miRNA

α-Synuclein is widely expressed in the adult brain. Mutations within the α-Synuclein gene are associated with autosomal dominant familial PD. The overexpression of the human wild-type form and the expression of α-Synuclein mutant forms exhibit a higher tendency to form insoluble aggregates and constitute the main structure of Lewy Bodies which result in increased susceptibility of neurons to oxidative stress.

Using several target prediction software tools, miR-504 was identified as a putative candidate and potential miR-504 binding sites in the 3' UTR region of α-Synuclein were identified. Using Western blot analysis, it was found that miR-504 that induces differentiation of MSCs to astrocytes, also decreases the expression of α-Synuclein (FIG. 10).

Example 5

Sequences

TABLE 3

| Name | Sequence of mature miRNA | Sequence of premiRNA |
|---|---|---|
| hsa-let-7a | seq id no: 1 | seq id no: 73 |
|  |  | seq id no: 74 |
|  |  | seq id no: 75 |
| hsa-let-7b | seq id no: 2 | seq id no: 76 |
| hsa-let-7c | seq id no: 3 | seq id no: 77 |
| hsa-let-7d | seq id no: 4 | seq id no: 78 |
| hsa-let-7e | seq id no: 5 | seq id no: 79 |
| hsa-let-7f | seq id no: 6 | seq id no: 80 |
| hsa-let-7g | seq id no: 7 | seq id no: 81 |
| hsa-let-7i | seq id no: 8 | seq id no: 82 |
| hsa-mir-106a | seq id no: 9 | seq id no: 83 |
| hsa-mir-106b | seq id no: 10 | seq id no: 84 |
| hsa-mir-1294 | seq id no: 11 | seq id no: 85 |
| hsa-mir-1297 | seq id no: 12 | seq id no: 86 |
| hsa-mir-143 | seq id no: 13 | seq id no: 87 |
| hsa-mir-144 | seq id no: 14 | seq id no: 88 |
| hsa-mir-145 | seq id no: 15 | seq id no: 89 |
| hsa-mir-17 | seq id no: 16 | seq id no: 90 |
| miR-181a | seq id no: 17 | seq id no: 91 |
| miR-181a | seq id no: 18 | seq id no: 92 |
| miR-181b | seq id no: 19 | seq id no: 93 |
| miR-181b | seq id no: 20 | seq id no: 94 |
| miR-181c | seq id no: 21 | seq id no: 95 |
| hsa-mir-181d | seq id no: 22 | seq id no: 96 |
| hsa-mir-199a-3p | seq id no: 23 | seq id no: 97 |
| hsa-mir-199b-3p | seq id no: 24 | seq id no: 98 |
| hsa-mir-202 | seq id no: 25 | seq id no: 99 |
| hsa-mir-20a | seq id no: 26 | seq id no: 100 |
| hsa-mir-20b | seq id no: 27 | seq id no: 101 |
| hsa-mir-2113 | seq id no: 28 | seq id no: 102 |
| hsa-mir-25 | seq id no: 29 | seq id no: 103 |
| hsa-mir-26a | seq id no: 30 | seq id no: 104 |
|  | seq id no: 31 | seq id no: 105 |
| hsa-mir-26b | seq id no: 32 | seq id no: 106 |
| hsa-mir-29a | seq id no: 33 | seq id no: 107 |
| hsa-mir-29b | seq id no: 34 | seq id no: 108 |
|  |  | seq id no: 109 |
| hsa-mir-29c | seq id no: 35 | seq id no: 110 |
| hsa-mir-3129-5p | seq id no: 36 | seq id no: 111 |
| hsa-mir-3177-5p | seq id no: 37 | seq id no: 112 |
| hsa-mir-32 | seq id no: 38 | seq id no: 113 |
| hsa-mir-326 | seq id no: 39 | seq id no: 114 |
| hsa-mir-330-5p | seq id no: 40 | seq id no: 115 |
| hsa-mir-363 | seq id no: 41 | seq id no: 116 |
| hsa-mir-3659 | seq id no: 42 | seq id no: 117 |
| hsa-mir-3662 | seq id no: 43 | seq id no: 118 |
| hsa-mir-367 | seq id no: 44 | seq id no: 119 |
| hsa-mir-372 | seq id no: 45 | seq id no: 120 |
| hsa-mir-373 | seq id no: 46 | seq id no: 121 |
| hsa-mir-3927 | seq id no: 47 | seq id no: 122 |
| hsa-mir-4262 | seq id no: 48 | seq id no: 123 |
| hsa-mir-4279 | seq id no: 49 | seq id no: 124 |
| hsa-mir-4458 | seq id no: 50 | seq id no: 125 |
| hsa-mir-4465 | seq id no: 51 | seq id no: 126 |
| hsa-mir-4500 | seq id no: 52 | seq id no: 127 |
| hsa-mir-4658 | seq id no: 53 | seq id no: 128 |
| hsa-mir-4724-3p | seq id no: 54 | seq id no: 129 |
| hsa-mir-4742-3p | seq id no: 55 | seq id no: 130 |
| hsa-mir-4770 | seq id no: 56 | seq id no: 131 |
| hsa-mir-519d | seq id no: 57 | seq id no: 132 |
| hsa-mir-520a-3p | seq id no: 58 | seq id no: 133 |
| hsa-mir-520b | seq id no: 59 | seq id no: 134 |
| hsa-mir-520c-3p | seq id no: 60 | seq id no: 135 |
| hsa-mir-520d-3p | seq id no: 61 | seq id no: 136 |
| hsa-mir-520d-5p | seq id no: 62 | seq id no: 137 |
| hsa-mir-520e | seq id no: 63 | seq id no: 138 |
| hsa-mir-524-5p | seq id no: 64 | seq id no: 139 |
| hsa-mir-642b | seq id no: 65 | seq id no: 140 |
| hsa-mir-656 | seq id no: 66 | seq id no: 141 |
| hsa-mir-767-5p | seq id no: 67 | seq id no: 142 |

TABLE 3-continued

| Name | Sequence of mature miRNA | Sequence of premiRNA |
|---|---|---|
| hsa-mir-92a | seq id no: 68 | seq id no: 143 |
|  | seq id no: 69 | seq id no: 144 |
| hsa-mir-92b | seq id no: 70 | seq id no: 145 |
| hsa-mir-93 | seq id no: 71 | seq id no: 146 |
| hsa-mir-98 | seq id no: 72 | seq id no: 147 |

TABLE 4

| Name | Sequence of mature | Sequence of premiRNA |
|---|---|---|
| hsa-mir-410 | seq id no: 148 | seq id no: 156 |
| hsa-mir-3163 | seq id no: 149 | seq id no: 157 |
| hsa-mir-148a | seq id no: 150 | seq id no: 158 |
| hsa-mir-148b | seq id no: 151 | seq id no: 159 |
| hsa-mir-152 | seq id no: 152 | seq id no: 160 |
| hsa-mir-3121-3p | seq id no: 153 | seq id no: 161 |
| hsa-mir-495 | seq id no: 154 | seq id no: 162 |
| hsa-mir-4680-3p | seq id no: 155 | seq id no: 163 |

TABLE 5

| Name | Sequence of mature | PMIR id | Sequence of premiRNA |
|---|---|---|---|
| miR-92ap | seq id no: 164 | MI0000093 | seq id no: 269 |
|  | seq id no: 165 | MI0000094 | seq id no: 270 |
| miR-21 | seq id no: 166 | MI0000077 | seq id no: 271 |
| miR-26a 5P | seq id no: 167 | MI0000083 | seq id no: 272 |
|  | seq id no: 168 | MI0000750 | seq id no: 273 |
| miR-18a | seq id no: 169 | MI0000072 | seq id no: 274 |
| miR-124 | seq id no: 170 | MI0000445 | seq id no: 275 |
|  | seq id no: 171 | MI0000443 | seq id no: 276 |
|  | seq id no: 172 | MI0000444 | seq id no: 277 |
| miR-99a | seq id no: 173 | MI0000101 | seq id no: 278 |
| miR-30c | seq id no: 174 | MI0000736 | seq id no: 279 |
|  |  | MI0000254 | seq id no: 280 |
| miR-301a 3P | seq id no: 175 | MI0000745 | seq id no: 281 |
| miR-145-50 | seq id no: 176 | MI0000461 | seq id no: 282 |
| miR-143-3p | seq id no: 177 | MI0000459 | seq id no: 283 |
| miR-373 3P | seq id no: 178 | MI0000781 | seq id no: 284 |
| miR-20b | seq id no: 179 | MI0001519 | seq id no: 285 |
| miR-29c 3P | seq id no: 180 | MI0000735 | seq id no: 286 |
| miR-29b 3P | seq id no: 181 | MI0000105 | seq id no: 287 |
|  |  | MI0000107 | seq id no: 288 |
| miR-143 |  |  |  |
| let-7g | seq id no: 182 | MI0000433 | seq id no: 289 |
| let-7a | seq id no: 183 | MI0000060 | seq id no: 290 |
|  |  | MI0000061 | seq id no: 291 |
|  |  | MI0000062 | seq id no: 292 |
| let-7b | seq id no: 184 | MI0000063 | seq id no: 293 |
| miR-98 | seq id no: 185 | MI0000100 | seq id no: 294 |
| miR-30a* | seq id no: 186 | MI0000088 | seq id no: 295 |
| miR-17 | seq id no: 187 | MI0000071 | seq id no: 296 |
| miR-1-1 | seq id no: 188 | MI0000651 | seq id no: 297 |
| miR-1-2 | seq id no: 189 | MI0000437 | seq id no: 298 |
| miR-192 | seq id no: 190 | MI0000234 | seq id no: 299 |
| miR-155 | seq id no: 191 | MI0000681 | seq id no: 300 |
| miR-516-ap a1-5p-- | seq id no: 192 | MI0003180 | seq id no: 301 |
| a2-3p-- | seq id no: 193 | MI0003181 | seq id no: 302 |
| miR-31 | seq id no: 194 | MI0000089 | seq id no: 303 |
| miR-181a | seq id no: 195 | MI0000289 | seq id no: 304 |
|  | seq id no: 196 | MI0000269 | seq id no: 305 |
| miR-181b | seq id no: 197 | MI0000270 | seq id no: 306 |
|  | seq id no: 198 | MI0000683 | seq id no: 307 |
| miR-181c | seq id no: 199 | MI0000271 | seq id no: 308 |
| miR-34-c | seq id no: 200 | MI0000743 | seq id no: 309 |
| miR-34b* | seq id no: 201 | MI0000742 | seq id no: 310 |
| miR-103a | seq id no: 202 | MI0000109 | seq id no: 311 |
|  | seq id no: 203 | MI0000108 | seq id no: 312 |
| miR-210 | seq id no: 204 | MI0000286 | seq id no: 313 |

TABLE 5-continued

| Name | Sequence of mature | PMIR id | Sequence of premiRNA |
|---|---|---|---|
| miR-16 | seq id no: 205 | MI0000070 | seq id no: 314 |
|  | seq id no: 206 | MI0000115 | seq id no: 315 |
| miR-30a | seq id no: 207 | MI0000088 | seq id no: 316 |
| miR-31 | seq id no: 208 | MI0000089 | seq id no: 317 |
| miR-222 | seq id no: 209 | MI0000299 | seq id no: 318 |
| miR-17 | seq id no: 210 | MI0000071 | seq id no: 319 |
| miR-17* | seq id no: 211 | MI0000071 | seq id no: 320 |
| miR-200b | seq id no: 212 | MI0000342 | seq id no: 321 |
| miR-200c | seq id no: 213 | MI0000650 | seq id no: 322 |
| miR-128 | seq id no: 214 | MI0000447 | seq id no: 323 |
|  |  | MI0000727 | seq id no: 324 |
| miR-503 | seq id no: 215 | MI0003188 | seq id no: 325 |
| miR-424 | seq id no: 216 | MI0001446 | seq id no: 326 |
| miR-195 | seq id no: 217 | MI0000489 | seq id no: 327 |
| miR-1256 | seq id no: 218 | MI0006390 | seq id no: 328 |
| miR-203a | seq id no: 219 | MI0000283 | seq id no: 329 |
| miR-199 |  |  |  |
| hsa-miR-199a-3p_st | seq id no: 220 | MI0000242 | seq id no: 330 |
| hsa-miR-199a-5p_st | seq id no: 221 | MI0000242 | seq id no: 331 |
| hsa-miR-199b-3p_st | seq id no: 222 | MI0000282 | seq id no: 332 |
| miR-93 | seq id no: 223 | MI0000095 | seq id no: 333 |
| miR-98 | seq id no: 224 | MI0000100 | seq id no: 334 |
| miR-125-a | seq id no: 225 | MI0000469 | seq id no: 335 |
| miR-133a | seq id no: 226 | MI0000450 | seq id no: 336 |
|  |  | MI0000451 | seq id no: 337 |
| miR-133b | seq id no: 227 | MI0000822 | seq id no: 338 |
| miR-126 | seq id no: 228 | MI0000471 | seq id no: 339 |
| miR-194 | seq id no: 229 | MI0000488 | seq id no: 340 |
|  |  | MI0000732 | seq id no: 341 |
| miR-346 | seq id no: 230 | MI0000826 | seq id no: 342 |
| miR-15b | seq id no: 231 | MI0000438 | seq id no: 343 |
| miR-338-3p | seq id no: 232 | MI0000814 | seq id no: 344 |
| miR-373 |  |  |  |
| miR-205 | seq id no: 233 | MI0000285 | seq id no: 345 |
| miR-210 |  |  |  |
| miR-125 |  |  |  |
| miR-1226 | seq id no: 234 | MI0006313 | seq id no: 346 |
| miR-708 | seq id no: 235 | MI0005543 | seq id no: 347 |
| miR-449 | seq id no: 236 | MI0001648 | seq id no: 348 |
| miR-422 | seq id no: 237 | MI0001444 | seq id no: 349 |
| miR-340 | seq id no: 238 | MI0000802 | seq id no: 350 |
| miR-605 | seq id no: 239 | MI0003618 | seq id no: 351 |
| miR-522 | seq id no: 240 | MI0003177 | seq id no: 352 |
| miR-663 | seq id no: 241 | MI0003672 | seq id no: 353 |
| miR-130a | seq id no: 242 | MI0000448 | seq id no: 354 |
| miR-130b | seq id no: 243 | MI0000748 | seq id no: 355 |
| miR-942 | seq id no: 244 | MI0005767 | seq id no: 356 |
| miR-572 | seq id no: 245 | MI0003579 | seq id no: 357 |
| miR-520 |  |  |  |
| miR-639 | seq id no: 246 | MI0003654 | seq id no: 358 |
| miR-654 | seq id no: 247 | MI0003676 | seq id no: 359 |
| miR-519 |  |  |  |
| miR-204 |  | seq id no: 248 | MI0000284 |
| miR-224 | seq id no: 249 | MI0000301 | seq id no: 360 |
| miR-616 | seq id no: 250 | MI0003629 | seq id no: 361 |
| miR-122 | seq id no: 251 | MI0000442 | seq id no: 362 |
| miR-299 3p-5p- | seq id no: 252 | MI0000744 | seq id no: 363 |
|  | seq id no: 253 |  | seq id no: 364 |
| miR-100 | seq id no: 254 | MI0000102 |  |
| miR-138 | seq id no: 255 | MI0000476 | seq id no: 365 |
| miR-140 | seq id no: 256 | MI0000456 | seq id no: 366 |
| miR-375 | seq id no: 257 | MI0000783 | seq id no: 367 |
| miR-217 | seq id no: 258 | MI0000293 | seq id no: 368 |
| miR-302 |  |  | seq id no: 369 |
| miR-372 |  | MI0000780 |  |
| miR-96 | seq id no: 259 | MI0000098 | seq id no: 370 |
| miR-127-3p | seq id no: 260 | MI0000472 | seq id no: 371 |
| miR-449 |  |  | seq id no: 372 |
| miR-135b | seq id no: 261 | MI0000810 |  |
| miR-101 | seq id no: 262 | MI0000103 | seq id no: 373 |
|  | seq id no: 263 | MI0000739 | seq id no: 374 |
| miR-326 | seq id no: 264 | MI0000808 | seq id no: 375 |
| miR-3245p-3p- | seq id no: 265 | MI0000813 | seq id no: 376 |
|  | seq id no: 266 | MI0000813 | seq id no: 377 |
| miR-335 | seq id no: 267 | MI0000816 | seq id no: 378 |
| miR-141 | seq id no: 268 | MI0000457 | seq id no: 379 |

TABLE 6

| Name | Sequence of mature miRNA | Sequence of premiRNA |
|---|---|---|
| miR-1275 | seq id no: 381 | seq id no: 414 |
| miR-891a | seq id no: 382 | seq id no: 415 |
| miR-154 | seq id no: 383 | seq id no: 416 |
| miR-1202 | seq id no: 384 | seq id no: 417 |
| miR-572 | seq id no: 385 | seq id no: 418 |
| miR-935a | seq id no: 386 | seq id no: 419 |
| miR-4317 | seq id no: 387 | seq id no: 420 |
| miR-153 | seq id no: 388 | seq id no: 421 |
|  |  | seq id no: 422 |
| miR-4288 | seq id no: 389 | seq id no: 423 |
| miR-409-5p | seq id no: 390 | seq id no: 424 |
| miR-193a-5p | seq id no: 391 | seq id no: 425 |
| miR-648 | seq id no: 392 | seq id no: 426 |
| miR-368 |  |  |
| miR-365 | seq id no: 393 | seq id no: 427 |
| miR-500 | seq id no: 394 | seq id no: 428 |
| miR-491 | seq id no: 395 | seq id no: 429 |
| hsa-miR-199a-3p_st | seq id no: 396 | seq id no: 430 |
|  | seq id no: 397 | seq id no: 431 |
| hsa-miR-199a-5p_st | seq id no: 398 | seq id no: 432 |
|  | seq id no: 399 | seq id no: 433 |
| miR-2113 | seq id no: 400 | seq id no: 434 |
| miR-372 | seq id no: 401 | seq id no: 435 |
| miR-373 | seq id no: 402 | seq id no: 436 |
| miR-942 | seq id no: 403 | seq id no: 437 |
| miR-1293 | seq id no: 404 | seq id no: 438 |
| miR-18 | seq id no: 405 | seq id no: 439 |
| miR-1182 | seq id no: 406 | seq id no: 440 |
| miR-1185 | seq id no: 407 | seq id no: 441 |
|  |  | seq id no: 442 |
| miR-1276 | seq id no: 408 | seq id no: 443 |
| miR-193b | seq id no: 409 | seq id no: 444 |
| miR-1238 | seq id no: 410 | seq id no: 445 |

TABLE 6-continued

| Name | Sequence of mature miRNA | Sequence of premiRNA |
|---|---|---|
| miR-889 | seq id no: 411 | seq id no: 446 |
| miR-370 | seq id no: 412 | seq id no: 447 |
| miR-548-d1 | seq id no: 413 | seq id no: 448 |

TABLE 7

| Name | Sequence of mature miRNA |
|---|---|
| hsa-miR-20b | seq id no: 449 |
| hsa-miR-18 | seq id no: 450 |
| hsa-miR-17-5p | seq id no: 451 |
| hsa-miR-141 | seq id no: 452 |
| hsa-miR-302b | seq id no: 453 |
| hsa-miR-101 | seq id no: 454 |
| hsa-miR-126 | seq id no: 455 |
| hsa-miR-146a | seq id no: 456 |
| hsa-miR-146b | seq id no: 457 |
| hsa-miR-26 | seq id no: 458 |
| hsa-miR-29 | seq id no: 459 |
| hsa-miR-132 | seq id no: 460 |
| hsa-miR-9 | seq id no: 461 |
| hsa-miR-146 | seq id no: 462 |
| hsa-miR-10b | seq id no: 463 |
| hsa-miR-222 | seq id no: 464 |
| hsa-miR-193b | seq id no: 465 |
| hsa-miR-221 | seq id no: 466 |

TABLE 7-continued

| Name | Sequence of mature miRNA |
|---|---|
| hsa-miR-135a | seq id no: 467 |
| hsa-miR-149 | seq id no: 468 |
| hsa-miR-199a | seq id no: 469 |
| hsa-miR-302a | seq id no: 470 |
| hsa-miR-302c | seq id no: 471 |
| hsa-miR-302d | seq id no: 472 |
| hsa-miR-369-3p | seq id no: 473 |
| hsa-miR-370 | seq id no: 474 |
| hsa-miR-let7a | seq id no: 475 |
| hsa-miR-let7b | seq id no: 476 |
| hsa-miR-10b | seq id no: 477 |
| hsa-miR-23a | seq id no: 478 |
| hsa-miR-23b | seq id no: 479 |
| hsa-miR-32 | seq id no: 480 |

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

All publications, patents and patent applications mentioned in this specification are herein incorporated in their entirety by reference into the specification, to the same extent as if each individual publication, patent or patent application was specifically and individually indicated to be incorporated herein by reference. In addition, citation or identification of any reference in this application shall not be construed as an admission that such reference is available as prior art to the present invention. To the extent that section headings are used, they should not be construed as necessarily limiting.

What is claimed is:

1. An isolated population of genetically modified mesenchymal stem cells (MSCs) differentiated toward an astrocytic phenotype wherein each MSC comprises a combination of an exogenous microRNA (miR)-146 (SEQ ID NO:462) and an antagomir or RNA oligonucleotide that hybridizes to and inhibits an endogenous miR-302 (SEQ ID NO:369), wherein at least 50% of the MSCs express glial fibrillary acidic protein.

2. The isolated population of MSCs of claim 1, wherein the at least 50% of the population of MSCs differentiated toward an astrocytic phenotype is further identified by expression of a marker selected from the group consisting of protein S100, glutamine synthetase, excitatory amino acid transporter 1 (EAAT1) and EAAT2.

3. A pharmaceutical composition comprising the isolated population of cells of claim 1 and a pharmaceutically acceptable carrier.

4. The isolated population of MSCs of claim 1, wherein the at least 50% of the population of MSCs differentiated toward an astrocytic phenotype is further identified by astrocytic morphology.

5. A method of generating an isolated population of genetically modified mesenchymal stem cells (MSCs) differentiated toward an astrocytic phenotype, wherein at least 50% of the MSCs express glial fibrillary acidic protein, the method comprising introducing and expressing in MSCs a combination of an exogenous microRNA (miR)-146 (SEQ ID NO:462) and an antagomir or RNA oligonucleotide that hybridizes to and inhibits an endogenous miR-302 (SEQ ID NO:369), thereby generating an isolated population of genetically modified mesenchymal stem cells (MSCs) differentiated toward an astrocytic phenotype.

6. The method of claim 5, wherein said MSCs are isolated from a tissue selected from the group consisting of bone marrow, adipose tissue, placenta, cord blood and umbilical cord.

7. The method of claim 5, wherein said introducing comprises transfecting said MSCs with an expression vector which comprises a polynucleotide sequence which encodes a pre-miRNA of said miR-146 or a polynucleotide sequence which encodes said miR-146.

8. The method of claim 5 further comprising analyzing an expression of at least one marker selected from the group consisting of S100, glutamine sythetase, excitatory amino acid transporter 1 and EAAT2 following said generating.

9. The method of claim 5, further comprising incubating said MSCs in a differentiation medium comprising at least one agent selected from the group consisting of platelet derived growth factor (PDGF), neuregulin, fibroblast growth factor 2 (FGF-b) and a c-AMP inducing agent following, prior to or concomitant with said expressing.

* * * * *

SEQUENCE LISTING

```
<160> NUMBER OF SEQ ID NOS: 480

<210> SEQ ID NO 1
<211> LENGTH: 22
<212> TYPE: RNA
<213> ORGANISM: Homo sapiens

<400> SEQUENCE: 1
ugagguagua gguuguauag uu                                             22

<210> SEQ ID NO 2
<211> LENGTH: 22
<212> TYPE: RNA
<213> ORGANISM: Homo sapiens

<400> SEQUENCE: 2
```
ugagguagua gguugugugg uu					22

<210> SEQ ID NO 3
<211> LENGTH: 22
<212> TYPE: RNA
<213> ORGANISM: Homo sapiens

<400> SEQUENCE: 3
ugagguagua gguuguaugg uu					22

<210> SEQ ID NO 4
<211> LENGTH: 22
<212> TYPE: RNA
<213> ORGANISM: Homo sapiens

<400> SEQUENCE: 4
agagguagua gguugcauag uu					22

<210> SEQ ID NO 5
<211> LENGTH: 22
<212> TYPE: RNA
<213> ORGANISM: Homo sapiens

<400> SEQUENCE: 5
ugagguagga gguuguauag uu					22

<210> SEQ ID NO 6
<211> LENGTH: 22
<212> TYPE: RNA
<213> ORGANISM: Homo sapiens

<400> SEQUENCE: 6
ugagguagua gauuguauag uu					22

<210> SEQ ID NO 7
<211> LENGTH: 22
<212> TYPE: RNA
<213> ORGANISM: Homo sapiens

<400> SEQUENCE: 7
ugagguagua guuguacag uu					22

<210> SEQ ID NO 8
<211> LENGTH: 22
<212> TYPE: RNA
<213> ORGANISM: Homo sapiens

<400> SEQUENCE: 8
ugagguagua guuugugcug uu					22

<210> SEQ ID NO 9
<211> LENGTH: 23
<212> TYPE: RNA
<213> ORGANISM: Homo sapiens

<400> SEQUENCE: 9
aaaagugcuu acagugcagg uag					23

<210> SEQ ID NO 10
<211> LENGTH: 21
<212> TYPE: RNA
<213> ORGANISM: Homo sapiens

```
<400> SEQUENCE: 10
uaaagugcug acagugcaga u                                    21

<210> SEQ ID NO 11
<211> LENGTH: 22
<212> TYPE: RNA
<213> ORGANISM: Homo sapiens

<400> SEQUENCE: 11
ugugagguug gcauuguugu cu                                   22

<210> SEQ ID NO 12
<211> LENGTH: 17
<212> TYPE: RNA
<213> ORGANISM: Homo sapiens

<400> SEQUENCE: 12
uucaaguaau ucaggug                                         17

<210> SEQ ID NO 13
<211> LENGTH: 22
<212> TYPE: RNA
<213> ORGANISM: Homo sapiens

<400> SEQUENCE: 13
ggugcagugc ugcaucucug gu                                   22

<210> SEQ ID NO 14
<211> LENGTH: 20
<212> TYPE: RNA
<213> ORGANISM: Homo sapiens

<400> SEQUENCE: 14
uacaguauag augauguacu                                      20

<210> SEQ ID NO 15
<211> LENGTH: 23
<212> TYPE: RNA
<213> ORGANISM: Homo sapiens

<400> SEQUENCE: 15
guccaguuuu cccaggaauc ccu                                  23

<210> SEQ ID NO 16
<211> LENGTH: 23
<212> TYPE: RNA
<213> ORGANISM: Homo sapiens

<400> SEQUENCE: 16
caaagugcuu acagugcagg uag                                  23

<210> SEQ ID NO 17
<211> LENGTH: 23
<212> TYPE: RNA
<213> ORGANISM: Homo sapiens

<400> SEQUENCE: 17
aacauucaac gcugucggug agu                                  23

<210> SEQ ID NO 18
<211> LENGTH: 23
<212> TYPE: RNA
<213> ORGANISM: Homo sapiens
```

```
<400> SEQUENCE: 18
aacauucaac gcugucggug agu                                        23

<210> SEQ ID NO 19
<211> LENGTH: 23
<212> TYPE: RNA
<213> ORGANISM: Homo sapiens

<400> SEQUENCE: 19
aacauucauu gcugucggug ggu                                        23

<210> SEQ ID NO 20
<211> LENGTH: 23
<212> TYPE: RNA
<213> ORGANISM: Homo sapiens

<400> SEQUENCE: 20
aacauucauu gcugucggug ggu                                        23

<210> SEQ ID NO 21
<211> LENGTH: 22
<212> TYPE: RNA
<213> ORGANISM: Homo sapiens

<400> SEQUENCE: 21
aacauucaac cugucgguga gu                                         22

<210> SEQ ID NO 22
<211> LENGTH: 23
<212> TYPE: RNA
<213> ORGANISM: Homo sapiens

<400> SEQUENCE: 22
aacauucauu guugucggug ggu                                        23

<210> SEQ ID NO 23
<211> LENGTH: 22
<212> TYPE: RNA
<213> ORGANISM: Homo sapiens

<400> SEQUENCE: 23
acaguagucu gcacauuggu ua                                         22

<210> SEQ ID NO 24
<211> LENGTH: 22
<212> TYPE: RNA
<213> ORGANISM: Homo sapiens

<400> SEQUENCE: 24
acaguagucu gcacauuggu ua                                         22

<210> SEQ ID NO 25
<211> LENGTH: 20
<212> TYPE: RNA
<213> ORGANISM: Homo sapiens

<400> SEQUENCE: 25
agagguauag ggcaugggaa                                            20

<210> SEQ ID NO 26
<211> LENGTH: 23
<212> TYPE: RNA
```

<213> ORGANISM: Homo sapiens

<400> SEQUENCE: 26
uaaagugcuu auagugcagg uag                                           23

<210> SEQ ID NO 27
<211> LENGTH: 23
<212> TYPE: RNA
<213> ORGANISM: Homo sapiens

<400> SEQUENCE: 27
caaagugcuc auagugcagg uag                                           23

<210> SEQ ID NO 28
<211> LENGTH: 21
<212> TYPE: RNA
<213> ORGANISM: Homo sapiens

<400> SEQUENCE: 28
auuugugcuu ggcucuguca c                                             21

<210> SEQ ID NO 29
<211> LENGTH: 22
<212> TYPE: RNA
<213> ORGANISM: Homo sapiens

<400> SEQUENCE: 29
cauugcacuu gucucggucu ga                                            22

<210> SEQ ID NO 30
<211> LENGTH: 22
<212> TYPE: RNA
<213> ORGANISM: Homo sapiens

<400> SEQUENCE: 30
uucaaguaau ccaggauagg cu                                            22

<210> SEQ ID NO 31
<211> LENGTH: 22
<212> TYPE: RNA
<213> ORGANISM: Homo sapiens

<400> SEQUENCE: 31
uucaaguaau ccaggauagg cu                                            22

<210> SEQ ID NO 32
<211> LENGTH: 21
<212> TYPE: RNA
<213> ORGANISM: Homo sapiens

<400> SEQUENCE: 32
uucaaguaau ucaggauagg u                                             21

<210> SEQ ID NO 33
<211> LENGTH: 22
<212> TYPE: RNA
<213> ORGANISM: Homo sapiens

<400> SEQUENCE: 33
uagcaccauc ugaaaucggu ua                                            22

<210> SEQ ID NO 34
<211> LENGTH: 23

```
<212> TYPE: RNA
<213> ORGANISM: Homo sapiens

<400> SEQUENCE: 34
uagcaccauu ugaaaucagu guu                                              23

<210> SEQ ID NO 35
<211> LENGTH: 22
<212> TYPE: RNA
<213> ORGANISM: Homo sapiens

<400> SEQUENCE: 35
uagcaccauu ugaaaucggu ua                                               22

<210> SEQ ID NO 36
<211> LENGTH: 22
<212> TYPE: RNA
<213> ORGANISM: Homo sapiens

<400> SEQUENCE: 36
gcaguagugu agagauuggu uu                                               22

<210> SEQ ID NO 37
<211> LENGTH: 23
<212> TYPE: RNA
<213> ORGANISM: Homo sapiens

<400> SEQUENCE: 37
uguguacaca cgugccaggc gcu                                              23

<210> SEQ ID NO 38
<211> LENGTH: 22
<212> TYPE: RNA
<213> ORGANISM: Homo sapiens

<400> SEQUENCE: 38
uauugcacau uacuaaguug ca                                               22

<210> SEQ ID NO 39
<211> LENGTH: 20
<212> TYPE: RNA
<213> ORGANISM: Homo sapiens

<400> SEQUENCE: 39
ccucugggcc cuuccuccag                                                  20

<210> SEQ ID NO 40
<211> LENGTH: 23
<212> TYPE: RNA
<213> ORGANISM: Homo sapiens

<400> SEQUENCE: 40
gcaaagcaca cggccugcag aga                                              23

<210> SEQ ID NO 41
<211> LENGTH: 22
<212> TYPE: RNA
<213> ORGANISM: Homo sapiens

<400> SEQUENCE: 41
aauugcacgg uauccaucug ua                                               22

<210> SEQ ID NO 42
```

```
<211> LENGTH: 21
<212> TYPE: RNA
<213> ORGANISM: Homo sapiens

<400> SEQUENCE: 42
ugaguguugu cuacgagggc a                                          21

<210> SEQ ID NO 43
<211> LENGTH: 24
<212> TYPE: RNA
<213> ORGANISM: Homo sapiens

<400> SEQUENCE: 43
gaaaaugaug aguagugacu gaug                                       24

<210> SEQ ID NO 44
<211> LENGTH: 22
<212> TYPE: RNA
<213> ORGANISM: Homo sapiens

<400> SEQUENCE: 44
aauugcacuu uagcaauggu ga                                         22

<210> SEQ ID NO 45
<211> LENGTH: 23
<212> TYPE: RNA
<213> ORGANISM: Homo sapiens

<400> SEQUENCE: 45
aaagugcugc gacauuugag cgu                                        23

<210> SEQ ID NO 46
<211> LENGTH: 23
<212> TYPE: RNA
<213> ORGANISM: Homo sapiens

<400> SEQUENCE: 46
gaagugcuuc gauuuugggg ugu                                        23

<210> SEQ ID NO 47
<211> LENGTH: 22
<212> TYPE: RNA
<213> ORGANISM: Homo sapiens

<400> SEQUENCE: 47
cagguagaua uuugauaggc au                                         22

<210> SEQ ID NO 48
<211> LENGTH: 17
<212> TYPE: RNA
<213> ORGANISM: Homo sapiens

<400> SEQUENCE: 48
gacauucaga cuaccug                                               17

<210> SEQ ID NO 49
<211> LENGTH: 16
<212> TYPE: RNA
<213> ORGANISM: Homo sapiens

<400> SEQUENCE: 49
cucuccuccc ggcuuc                                                16
```

-continued

```
<210> SEQ ID NO 50
<211> LENGTH: 19
<212> TYPE: RNA
<213> ORGANISM: Homo sapiens

<400> SEQUENCE: 50
agagguaggu guggaagaa                                                  19

<210> SEQ ID NO 51
<211> LENGTH: 22
<212> TYPE: RNA
<213> ORGANISM: Homo sapiens

<400> SEQUENCE: 51
cucaaguagu cugaccaggg ga                                              22

<210> SEQ ID NO 52
<211> LENGTH: 17
<212> TYPE: RNA
<213> ORGANISM: Homo sapiens

<400> SEQUENCE: 52
ugagguagua guuucuu                                                    17

<210> SEQ ID NO 53
<211> LENGTH: 23
<212> TYPE: RNA
<213> ORGANISM: Homo sapiens

<400> SEQUENCE: 53
gugagugugg auccuggagg aau                                             23

<210> SEQ ID NO 54
<211> LENGTH: 21
<212> TYPE: RNA
<213> ORGANISM: Homo sapiens

<400> SEQUENCE: 54
guaccuucug guucagcuag u                                               21

<210> SEQ ID NO 55
<211> LENGTH: 23
<212> TYPE: RNA
<213> ORGANISM: Homo sapiens

<400> SEQUENCE: 55
ucuguauucu ccuuugccug cag                                             23

<210> SEQ ID NO 56
<211> LENGTH: 18
<212> TYPE: RNA
<213> ORGANISM: Homo sapiens

<400> SEQUENCE: 56
ugagaugaca cuguagcu                                                   18

<210> SEQ ID NO 57
<211> LENGTH: 22
<212> TYPE: RNA
<213> ORGANISM: Homo sapiens

<400> SEQUENCE: 57
caaagugccu cccuuuagag ug                                              22
```

```
<210> SEQ ID NO 58
<211> LENGTH: 22
<212> TYPE: RNA
<213> ORGANISM: Homo sapiens

<400> SEQUENCE: 58
aaagugcuuc ccuuuggacu gu                                              22

<210> SEQ ID NO 59
<211> LENGTH: 21
<212> TYPE: RNA
<213> ORGANISM: Homo sapiens

<400> SEQUENCE: 59
aaagugcuuc cuuuuagagg g                                               21

<210> SEQ ID NO 60
<211> LENGTH: 22
<212> TYPE: RNA
<213> ORGANISM: Homo sapiens

<400> SEQUENCE: 60
aaagugcuuc cuuuuagagg gu                                              22

<210> SEQ ID NO 61
<211> LENGTH: 22
<212> TYPE: RNA
<213> ORGANISM: Homo sapiens

<400> SEQUENCE: 61
aaagugcuuc ucuuuggugg gu                                              22

<210> SEQ ID NO 62
<211> LENGTH: 20
<212> TYPE: RNA
<213> ORGANISM: Homo sapiens

<400> SEQUENCE: 62
cuacaaaggg aagcccuuuc                                                 20

<210> SEQ ID NO 63
<211> LENGTH: 21
<212> TYPE: RNA
<213> ORGANISM: Homo sapiens

<400> SEQUENCE: 63
aaagugcuuc cuuuuugagg g                                               21

<210> SEQ ID NO 64
<211> LENGTH: 22
<212> TYPE: RNA
<213> ORGANISM: Homo sapiens

<400> SEQUENCE: 64
cuacaaaggg aagcacuuuc uc                                              22

<210> SEQ ID NO 65
<211> LENGTH: 22
<212> TYPE: RNA
<213> ORGANISM: Homo sapiens

<400> SEQUENCE: 65
agacacauuu ggagagggac cc                                              22
```

```
<210> SEQ ID NO 66
<211> LENGTH: 21
<212> TYPE: RNA
<213> ORGANISM: Homo sapiens

<400> SEQUENCE: 66
aauauuauac agucaaccuc u                                              21

<210> SEQ ID NO 67
<211> LENGTH: 23
<212> TYPE: RNA
<213> ORGANISM: Homo sapiens

<400> SEQUENCE: 67
ugcaccaugg uugucugagc aug                                            23

<210> SEQ ID NO 68
<211> LENGTH: 22
<212> TYPE: RNA
<213> ORGANISM: Homo sapiens

<400> SEQUENCE: 68
uauugcacuu gucccggccu gu                                             22

<210> SEQ ID NO 69
<211> LENGTH: 22
<212> TYPE: RNA
<213> ORGANISM: Homo sapiens

<400> SEQUENCE: 69
uauugcacuu gucccggccu gu                                             22

<210> SEQ ID NO 70
<211> LENGTH: 22
<212> TYPE: RNA
<213> ORGANISM: Homo sapiens

<400> SEQUENCE: 70
uauugcacuc gucccggccu cc                                             22

<210> SEQ ID NO 71
<211> LENGTH: 23
<212> TYPE: RNA
<213> ORGANISM: Homo sapiens

<400> SEQUENCE: 71
caaagugcug uucgugcagg uag                                            23

<210> SEQ ID NO 72
<211> LENGTH: 22
<212> TYPE: RNA
<213> ORGANISM: Homo sapiens

<400> SEQUENCE: 72
ugagguagua aguuguauug uu                                             22

<210> SEQ ID NO 73
<211> LENGTH: 80
<212> TYPE: RNA
<213> ORGANISM: Homo sapiens

<400> SEQUENCE: 73
```

| | |
|---|---|
| ugggaugagg uaguagguug uauaguuuua gggucacacc caccacuggg agauaacuau | 60 |
| acaaucuacu gucuuccua | 80 |

<210> SEQ ID NO 74
<211> LENGTH: 72
<212> TYPE: RNA
<213> ORGANISM: Homo sapiens

<400> SEQUENCE: 74

| | |
|---|---|
| agguugaggu aguagguugu auaguuuaga auuacaucaa gggagauaac uguacagccu | 60 |
| ccuagcuuuc cu | 72 |

<210> SEQ ID NO 75
<211> LENGTH: 74
<212> TYPE: RNA
<213> ORGANISM: Homo sapiens

<400> SEQUENCE: 75

| | |
|---|---|
| gggugaggua guagguugua uaguuuggg cucugcccug cuaugggaua acuauacaau | 60 |
| cuacugucuu uccu | 74 |

<210> SEQ ID NO 76
<211> LENGTH: 83
<212> TYPE: RNA
<213> ORGANISM: Homo sapiens

<400> SEQUENCE: 76

| | |
|---|---|
| cggggugagg uaguagguug uguggguuca gggcagugau uugcccuc ggaagauaac | 60 |
| uauacaaccu acugccuucc cug | 83 |

<210> SEQ ID NO 77
<211> LENGTH: 84
<212> TYPE: RNA
<213> ORGANISM: Homo sapiens

<400> SEQUENCE: 77

| | |
|---|---|
| gcauccgggu ugagguagua gguuguaugg uuuagaguua cacccuggga guuaacugua | 60 |
| caaccuucua gcuuuccuug gagc | 84 |

<210> SEQ ID NO 78
<211> LENGTH: 87
<212> TYPE: RNA
<213> ORGANISM: Homo sapiens

<400> SEQUENCE: 78

| | |
|---|---|
| ccuaggaaga gguaguaggu ugcauaguuu uagggcaggg auuuugccca caaggaggua | 60 |
| acuauacgac cugcugccuu ucuuagg | 87 |

<210> SEQ ID NO 79
<211> LENGTH: 79
<212> TYPE: RNA
<213> ORGANISM: Homo sapiens

<400> SEQUENCE: 79

| | |
|---|---|
| cccgggcuga gguaggaggu uguauaguug aggaggacac ccaaggagau cacuauacgg | 60 |
| ccuccuagcu uuccccagg | 79 |

<210> SEQ ID NO 80
<211> LENGTH: 87

<212> TYPE: RNA
<213> ORGANISM: Homo sapiens

<400> SEQUENCE: 80
ucagagugag guaguagauu guauaguugu gggguaguga uuuuacccug uucaggagau      60
aacuauacaa ucuauugccu uccucuga                                         87

<210> SEQ ID NO 81
<211> LENGTH: 84
<212> TYPE: RNA
<213> ORGANISM: Homo sapiens

<400> SEQUENCE: 81
aggcugaggu aguaguuugu acaguuugag ggucuaugau accacccggu acaggagaua      60
acuguacagg ccacugccuu gcca                                             84

<210> SEQ ID NO 82
<211> LENGTH: 84
<212> TYPE: RNA
<213> ORGANISM: Homo sapiens

<400> SEQUENCE: 82
cuggcugagg uaguaguuug ugcuguuggu cggguguga cauugcccgc uguggagaua       60
acugcgcaag cuacugccuu gcua                                             84

<210> SEQ ID NO 83
<211> LENGTH: 81
<212> TYPE: RNA
<213> ORGANISM: Homo sapiens

<400> SEQUENCE: 83
ccuuggccau guaaaagugc uuacagugca gguagcuuuu ugagaucuac ugcaauguaa      60
gcacuucuua cauuaccaug g                                                81

<210> SEQ ID NO 84
<211> LENGTH: 82
<212> TYPE: RNA
<213> ORGANISM: Homo sapiens

<400> SEQUENCE: 84
ccugccgggg cuaaagugcu gacagugcag auaguggucc ucuccgugcu accgcacugu      60
ggguacuugc ugcuccagca gg                                               82

<210> SEQ ID NO 85
<211> LENGTH: 142
<212> TYPE: RNA
<213> ORGANISM: Homo sapiens

<400> SEQUENCE: 85
caccuaaugu gugccaagau cuguucauuu augaucucac cgagcccugu gaagguuggca     60 uuguugucug gcauugucug auauacaaca gugccaaccu cacaggacuc agugaggug a    120 aacugaggau uaggaaggug ua                                              142

<210> SEQ ID NO 86
<211> LENGTH: 77
<212> TYPE: RNA
<213> ORGANISM: Homo sapiens

<400> SEQUENCE: 86

```
uguuuaucuc uagggUUgau cuauuagaau uacuuaucug agccaaagua auucaaguaa    60
uucaggugua gugaaac                                                    77

<210> SEQ ID NO 87
<211> LENGTH: 106
<212> TYPE: RNA
<213> ORGANISM: Homo sapiens

<400> SEQUENCE: 87
gcgcagcgcc cugucuccca gccugaggug cagugcugca ucucggUca guugggaguc    60 ugagaugaag cacuguagcu caggaagaga gaaguuguuc ugcagc                  106

<210> SEQ ID NO 88
<211> LENGTH: 86
<212> TYPE: RNA
<213> ORGANISM: Homo sapiens

<400> SEQUENCE: 88
uggggcccug gcugggauau caucauauac uguaaguuug cgaugagaca cuacaguaua    60
gaugauguac uagUccgggc accccc                                         86

<210> SEQ ID NO 89
<211> LENGTH: 88
<212> TYPE: RNA
<213> ORGANISM: Homo sapiens

<400> SEQUENCE: 89
caccuugucc ucacggucca guuuucccag gaaucccuua gaugcuaaga uggggauucc    60
uggaaauacu guucuugagg ucauggUu                                       88

<210> SEQ ID NO 90
<211> LENGTH: 84
<212> TYPE: RNA
<213> ORGANISM: Homo sapiens

<400> SEQUENCE: 90
gucagaauaa ugucaaagug cuuacagugc agguagugau augugcaucu acugcaguga    60
aggcacuugu agcauuaugg ugac                                           84

<210> SEQ ID NO 91
<211> LENGTH: 110
<212> TYPE: RNA
<213> ORGANISM: Homo sapiens

<400> SEQUENCE: 91
ugaguuuuga gguugcuuca gugaacauuc aacgcugucg gugaguuugg aauuaaaauc    60
aaaaccaucg accguugauu guacccuaug gcuaaccauc aucuacucca               110

<210> SEQ ID NO 92
<211> LENGTH: 110
<212> TYPE: RNA
<213> ORGANISM: Homo sapiens

<400> SEQUENCE: 92
agaagggcua ucaggccagc cuucagagga cuccaaggaa cauucaacgc ugucggugag    60
uuugggauuu gaaaaaacca cugaccguug acuguaccuu ggggucccUUa               110

<210> SEQ ID NO 93
<211> LENGTH: 110
```

```
<212> TYPE: RNA
<213> ORGANISM: Homo sapiens

<400> SEQUENCE: 93
ccugugcaga gauuauuuuu uaaaagguca caaucaacau ucauugcugu cgguggguug      60
aacugugugg acaagcucac ugaacaauga augcaacugu ggccccgcuu               110

<210> SEQ ID NO 94
<211> LENGTH: 89
<212> TYPE: RNA
<213> ORGANISM: Homo sapiens

<400> SEQUENCE: 94
cugauggcug cacucaacau ucauugcugu cggugggu uu gagucugaau caacucacug     60
aucaaugaau gcaaacugcg gaccaaaca                                       89

<210> SEQ ID NO 95
<211> LENGTH: 110
<212> TYPE: RNA
<213> ORGANISM: Homo sapiens

<400> SEQUENCE: 95
cggaaaauuu gccaaggguu uggggggaaca uucaaccugu cggugaguuu gggcagcuca     60
ggcaaaccau cgaccguuga guggacccug aggccuggaa uugccauccu               110

<210> SEQ ID NO 96
<211> LENGTH: 137
<212> TYPE: RNA
<213> ORGANISM: Homo sapiens

<400> SEQUENCE: 96
guccccuccc cuaggccaca gccgagguca caaucaacau ucauuguugu cgguggguug      60
ugaggacuga ggccagaccc accggggau gaaugucacu guggcugggc cagacacggc     120
uuaaggggaa uggggac                                                   137

<210> SEQ ID NO 97
<211> LENGTH: 71
<212> TYPE: RNA
<213> ORGANISM: Homo sapiens

<400> SEQUENCE: 97
gccaacccag uguucagacu accuguucag gaggcucuca auguguacag uagucugcac      60
auugguuagg c                                                          71

<210> SEQ ID NO 98
<211> LENGTH: 110
<212> TYPE: RNA
<213> ORGANISM: Homo sapiens

<400> SEQUENCE: 98
ccagaggaca ccuccacucc gucuacccag uguuuagacu aucuguucag gacucccaaa      60
uuguacagua gucugcacau ugguuaggcu gggcuggguu agacccucgg               110

<210> SEQ ID NO 99
<211> LENGTH: 110
<212> TYPE: RNA
<213> ORGANISM: Homo sapiens

<400> SEQUENCE: 99
```

```
cgccucagag ccgcccgccg uuccuuuuuc cuaugcauau acuucuuuga ggaucuggcc    60
uaaagaggua uagggcaugg gaaaacgggg cggucgdguc cuccccagcg              110
```

<210> SEQ ID NO 100
<211> LENGTH: 71
<212> TYPE: RNA
<213> ORGANISM: Homo sapiens

<400> SEQUENCE: 100

```
guagcacuaa agugcuuaua gugcagguag uguuuaguua ucuacugcau uaugagcacu    60
uaaaguacug c                                                        71
```

<210> SEQ ID NO 101
<211> LENGTH: 69
<212> TYPE: RNA
<213> ORGANISM: Homo sapiens

<400> SEQUENCE: 101

```
aguaccaaag ugcucauagu gcagguaguu uuggcaugac cuacuguag uaugggcacu    60 uccaguacu                                                           69
```

<210> SEQ ID NO 102
<211> LENGTH: 91
<212> TYPE: RNA
<213> ORGANISM: Homo sapiens

<400> SEQUENCE: 102

```
uuuucaaagc aaugugugac agguacaggg acaaauccccg uuaauaagua agaggauuug    60
ugcuuggcuc ugucacaugc cacuuugaaa a                                  91
```

<210> SEQ ID NO 103
<211> LENGTH: 84
<212> TYPE: RNA
<213> ORGANISM: Homo sapiens

<400> SEQUENCE: 103

```
ggccagugu u gagaggcgga gacuuggggca auugcuggac gcugcccugg gcauugcacu    60
ugucucgguc ugacagugcc ggcc                                          84
```

<210> SEQ ID NO 104
<211> LENGTH: 77
<212> TYPE: RNA
<213> ORGANISM: Homo sapiens

<400> SEQUENCE: 104

```
guggccucgu ucaaguaauc caggauaggc ugugcagguc ccaaugggcc uauucuuggu    60
uacuugcacg gggacgc                                                  77
```

<210> SEQ ID NO 105
<211> LENGTH: 84
<212> TYPE: RNA
<213> ORGANISM: Homo sapiens

<400> SEQUENCE: 105

```
ggcuguggcu ggauucaagu aauccaggau aggcuguuuc caucugugag gccuauucuu    60
gauuacuugu uucuggaggc agcu                                          84
```

<210> SEQ ID NO 106
<211> LENGTH: 77

```
<212> TYPE: RNA
<213> ORGANISM: Homo sapiens

<400> SEQUENCE: 106
ccgggaccca guucaaguaa uucaggauag guugugugcu guccagccug uucuccauua    60
cuuggcucgg ggaccgg                                                  77

<210> SEQ ID NO 107
<211> LENGTH: 64
<212> TYPE: RNA
<213> ORGANISM: Homo sapiens

<400> SEQUENCE: 107
augacugauu ucuuuggug uucagaguca auauaauuuu cuagcaccau cugaaaucgg    60
uuau                                                                64

<210> SEQ ID NO 108
<211> LENGTH: 81
<212> TYPE: RNA
<213> ORGANISM: Homo sapiens

<400> SEQUENCE: 108
cuucaggaag cugguuucau auggugguuu agauuuaaau agugauuguc uagcaccauu    60
ugaaaucagu guucuugggg g                                             81

<210> SEQ ID NO 109
<211> LENGTH: 81
<212> TYPE: RNA
<213> ORGANISM: Homo sapiens

<400> SEQUENCE: 109
cuucuggaag cugguuucac augguggcuu agauuuuucc aucuuuguau cuagcaccau    60
uugaaaucag uguuuuagga g                                             81

<210> SEQ ID NO 110
<211> LENGTH: 88
<212> TYPE: RNA
<213> ORGANISM: Homo sapiens

<400> SEQUENCE: 110
aucucuuaca caggcugacc gauuucuccu gguguucaga gucuguuuuu gucuagcacc    60
auuugaaauc gguuaugaug uaggggga                                      88

<210> SEQ ID NO 111
<211> LENGTH: 76
<212> TYPE: RNA
<213> ORGANISM: Homo sapiens

<400> SEQUENCE: 111
guacuugggc aguaguguag agauuggu uu gccuguuaau gaauucaaac uaaucucuac    60
acugcugccc aagagc                                                   76

<210> SEQ ID NO 112
<211> LENGTH: 82
<212> TYPE: RNA
<213> ORGANISM: Homo sapiens

<400> SEQUENCE: 112
ccacgugcca uguguacaca cgugccaggc gcugucuuga gacauucgcg cagugcacgg    60
```

-continued

```
cacuggggac acguggcacu gg                                              82

<210> SEQ ID NO 113
<211> LENGTH: 70
<212> TYPE: RNA
<213> ORGANISM: Homo sapiens

<400> SEQUENCE: 113
ggagauauug cacauuacua aguugcaugu ugucacggcc ucaaugcaau uuagugugug     60
ugauauuuuc                                                           70

<210> SEQ ID NO 114
<211> LENGTH: 95
<212> TYPE: RNA
<213> ORGANISM: Homo sapiens

<400> SEQUENCE: 114
cucaucuguc uguugggcug gaggcagggc cuuugugaag gcggguggug cucagaucgc     60
cucugggccc uuccuccagc cccgaggcgg auuca                               95

<210> SEQ ID NO 115
<211> LENGTH: 94
<212> TYPE: RNA
<213> ORGANISM: Homo sapiens

<400> SEQUENCE: 115
cuuuggcgau cacugccucu cugggccugu gucuuaggcu cugcaagauc aaccgagcaa     60
agcacacggc cugcagagag gcagcgcucu gccc                                94

<210> SEQ ID NO 116
<211> LENGTH: 75
<212> TYPE: RNA
<213> ORGANISM: Homo sapiens

<400> SEQUENCE: 116
uguugucggg uggaucacga ugcaauuuug augaguauca uaggagaaaa auugcacggu     60
auccaucugu aaacc                                                     75

<210> SEQ ID NO 117
<211> LENGTH: 99
<212> TYPE: RNA
<213> ORGANISM: Homo sapiens

<400> SEQUENCE: 117
ucuacaagca gauacaagga ugcccuugua cacaacacac gugcugcuug uauagacaug     60 aguuugucu acgagggcau ccuugugucu gugugugug                            99

<210> SEQ ID NO 118
<211> LENGTH: 95
<212> TYPE: RNA
<213> ORGANISM: Homo sapiens

<400> SEQUENCE: 118
uguguuuucc ucaacgcuca caguuacacu ucuuacucuc aauccauuca uauugaaaau     60
gaugaguagu gacugaugaa gcacaaauca gccaa                               95

<210> SEQ ID NO 119
<211> LENGTH: 68
<212> TYPE: RNA
<213> ORGANISM: Homo sapiens
```

```
<400> SEQUENCE: 119
ccauuacugu ugcuaauaug caacucuguu gaauauaaau uggaauugca cuuuagcaau      60
ggugaugg                                                              68

<210> SEQ ID NO 120
<211> LENGTH: 67
<212> TYPE: RNA
<213> ORGANISM: Homo sapiens

<400> SEQUENCE: 120
gugggccuca aaugguggagc acuauucuga ugccaagug aaagugcug cgacauuuga      60 gcgucac                                                               67

<210> SEQ ID NO 121
<211> LENGTH: 69
<212> TYPE: RNA
<213> ORGANISM: Homo sapiens

<400> SEQUENCE: 121
gggauacuca aaaugggggc gcuuccuuu uugucuguac ugggaagugc uucgauuuug      60
ggugucccc                                                             69

<210> SEQ ID NO 122
<211> LENGTH: 71
<212> TYPE: RNA
<213> ORGANISM: Homo sapiens

<400> SEQUENCE: 122
ugccaaugcc uaucacauau cugccugucc uaugacaaac auggcaggua gauauuugau    60
aggcauuggc a                                                          71

<210> SEQ ID NO 123
<211> LENGTH: 54
<212> TYPE: RNA
<213> ORGANISM: Homo sapiens

<400> SEQUENCE: 123
gaaagcugca ggugcugaug uugggggggac auucagacua ccugcagcag agcc         54

<210> SEQ ID NO 124
<211> LENGTH: 58
<212> TYPE: RNA
<213> ORGANISM: Homo sapiens

<400> SEQUENCE: 124
ugcucugugg agcugaggag cagauucucu cucucuccuc ccggcuucac cuccugag      58

<210> SEQ ID NO 125
<211> LENGTH: 75
<212> TYPE: RNA
<213> ORGANISM: Homo sapiens

<400> SEQUENCE: 125
gagcgcacag agguaggugu ggaagaaagu gaaacacuau uuuagguuuu aguuacacuc    60 ugcugugguug ugcug                                                     75

<210> SEQ ID NO 126
<211> LENGTH: 70
<212> TYPE: RNA
```

<213> ORGANISM: Homo sapiens

<400> SEQUENCE: 126

```
cauguguccc cuggcacgcu auuugagguu uacuauggaa ccucaaguag ucugaccagg    60
ggacacauga                                                           70
```

<210> SEQ ID NO 127
<211> LENGTH: 76
<212> TYPE: RNA
<213> ORGANISM: Homo sapiens

<400> SEQUENCE: 127

```
caggagagaa aguacugccc agaagcuaaa guguagauca aacgcauaau ggcugaggua    60
guaguuucuu gaacuu                                                    76
```

<210> SEQ ID NO 128
<211> LENGTH: 65
<212> TYPE: RNA
<213> ORGANISM: Homo sapiens

<400> SEQUENCE: 128

```
gcugcccuuc acucagagca ucuacaccca cuaccgguga guguggaucc uggaggaauc    60
guggc                                                                65
```

<210> SEQ ID NO 129
<211> LENGTH: 89
<212> TYPE: RNA
<213> ORGANISM: Homo sapiens

<400> SEQUENCE: 129

```
acgcaaaaug aacugaacca ggagugagcu ucguguacau uaucuauuag aaaaugaagu    60
accuucuggu ucagcuaguc ccugugcgu                                      89
```

<210> SEQ ID NO 130
<211> LENGTH: 85
<212> TYPE: RNA
<213> ORGANISM: Homo sapiens

<400> SEQUENCE: 130

```
ucaggcaaag ggauauuuac agauacuuuu uaaaauuugu uugaguugag gcagauuaaa    60
uaucuguauu cuccuuugcc ugcag                                          85
```

<210> SEQ ID NO 131
<211> LENGTH: 58
<212> TYPE: RNA
<213> ORGANISM: Homo sapiens

<400> SEQUENCE: 131

```
gaguuauggg gucaucuauc cuucccuugg aaaaugaucu gagaugacac uguagcuc      58
```

<210> SEQ ID NO 132
<211> LENGTH: 88
<212> TYPE: RNA
<213> ORGANISM: Homo sapiens

<400> SEQUENCE: 132

```
ucccaugcug ugacccucca aagggaagcg cuuucuguuu guuuucucuu aaacaaagug    60
ccucccuuua gaguguuacc guuuggga                                       88
```

```
<210> SEQ ID NO 133
<211> LENGTH: 85
<212> TYPE: RNA
<213> ORGANISM: Homo sapiens

<400> SEQUENCE: 133
cucaggcugu gacccuccag agggaaguac uuucuguugu cugagagaaa agaaagugcu      60
ucccuuugga cuguuucggu uugag                                           85

<210> SEQ ID NO 134
<211> LENGTH: 61
<212> TYPE: RNA
<213> ORGANISM: Homo sapiens

<400> SEQUENCE: 134
cccucuacag ggaagcgcuu ucguugucu gaaagaaaag aaagugcuuc cuuuuagagg       60
g                                                                     61

<210> SEQ ID NO 135
<211> LENGTH: 87
<212> TYPE: RNA
<213> ORGANISM: Homo sapiens

<400> SEQUENCE: 135
ucucaggcug ucguccucua gagggaagca cuuucuguug ucugaaagaa agaaagugc       60 uuccuuuuag aggguuaccg uuugaga                                         87

<210> SEQ ID NO 136
<211> LENGTH: 87
<212> TYPE: RNA
<213> ORGANISM: Homo sapiens

<400> SEQUENCE: 136
ucucaagcug ugagucuaca aagggaagcc cuuucuguug ucuaaagaa aagaaagugc       60 uucucuuugg ugggguuacgg uuugaga                                        87

<210> SEQ ID NO 137
<211> LENGTH: 87
<212> TYPE: RNA
<213> ORGANISM: Homo sapiens

<400> SEQUENCE: 137
ucucaagcug ugagucuaca aagggaagcc cuuucuguug ucuaaagaa aagaaagugc       60 uucucuuugg ugggguuacgg uuugaga                                        87

<210> SEQ ID NO 138
<211> LENGTH: 87
<212> TYPE: RNA
<213> ORGANISM: Homo sapiens

<400> SEQUENCE: 138
ucuccugcug ugacccucaa gauggaagca guuucuguug ucgaaaggaa agaaagugc       60 uuccuuuuug aggguuacug uuugaga                                         87

<210> SEQ ID NO 139
<211> LENGTH: 87
<212> TYPE: RNA
<213> ORGANISM: Homo sapiens

<400> SEQUENCE: 139
```

```
ucucaugcug ugacccuaca aagggaagca cuuucucuug uccaaaggaa aagaaggcgc    60
uucccuuugg aguguuacgg uuugaga                                       87

<210> SEQ ID NO 140
<211> LENGTH: 77
<212> TYPE: RNA
<213> ORGANISM: Homo sapiens

<400> SEQUENCE: 140
gaguugggag guucccucuc caaauguguc uugaucccc accccaagac acauuuggag    60
agggacccuc ccaacuc                                                  77

<210> SEQ ID NO 141
<211> LENGTH: 78
<212> TYPE: RNA
<213> ORGANISM: Homo sapiens

<400> SEQUENCE: 141
cugaaauagg uugccuguga ggguucacu uucuauauga ugaauauuau acagucaacc    60
ucuuuccgau aucgaauc                                                 78

<210> SEQ ID NO 142
<211> LENGTH: 109
<212> TYPE: RNA
<213> ORGANISM: Homo sapiens

<400> SEQUENCE: 142
gcuuuuauau uguagguuuu ugcucaugca ccaugguugu cugagcaugc agcaugcuug    60
ucugcucaua ccccaugguu ucugagcagg aaccuucauu gucuacugc              109

<210> SEQ ID NO 143
<211> LENGTH: 78
<212> TYPE: RNA
<213> ORGANISM: Homo sapiens

<400> SEQUENCE: 143
cuuucuacac agguugggau cgguugcaau gcuguguuuc uguaugguau ugcacuuguc    60
ccggccuguu gaguuugg                                                 78

<210> SEQ ID NO 144
<211> LENGTH: 75
<212> TYPE: RNA
<213> ORGANISM: Homo sapiens

<400> SEQUENCE: 144
ucaucccugg guggggauuu guugcauuac uuguguucua uauaaaguau ugcacuuguc    60
ccggccugug gaaga                                                    75

<210> SEQ ID NO 145
<211> LENGTH: 96
<212> TYPE: RNA
<213> ORGANISM: Homo sapiens

<400> SEQUENCE: 145
cgggccccgg gcgggcggga gggacgggac gcggugcagu guuguuuuuu ccccgccaa    60 uauugcacuc gucccggccu ccggccccccc cggccc                           96

<210> SEQ ID NO 146
<211> LENGTH: 80
```

```
<212> TYPE: RNA
<213> ORGANISM: Homo sapiens

<400> SEQUENCE: 146 cuggggcuc caaagugcug uucgugcagg uagugugauu acccaaccua cugcugagcu    60
agcacuuccc gagccccgg                                                80

<210> SEQ ID NO 147
<211> LENGTH: 119
<212> TYPE: RNA
<213> ORGANISM: Homo sapiens

<400> SEQUENCE: 147
aggauucugc ucaugccagg gugagguagu aaguuguauu guugugggu agggauauua    60 ggccccaauu agaagauaac uauacaacuu acuacuuucc cuggugugug gcauauuca   119

<210> SEQ ID NO 148
<211> LENGTH: 21
<212> TYPE: RNA
<213> ORGANISM: Homo sapiens

<400> SEQUENCE: 148
aauauaacac agauggccug u                                             21

<210> SEQ ID NO 149
<211> LENGTH: 22
<212> TYPE: RNA
<213> ORGANISM: Homo sapiens

<400> SEQUENCE: 149
uauaaaauga gggcaguaag ac                                            22

<210> SEQ ID NO 150
<211> LENGTH: 22
<212> TYPE: RNA
<213> ORGANISM: Homo sapiens

<400> SEQUENCE: 150
ucagugcacu acagaacuuu gu                                            22

<210> SEQ ID NO 151
<211> LENGTH: 22
<212> TYPE: RNA
<213> ORGANISM: Homo sapiens

<400> SEQUENCE: 151
ucagugcauc acagaacuuu gu                                            22

<210> SEQ ID NO 152
<211> LENGTH: 21
<212> TYPE: RNA
<213> ORGANISM: Homo sapiens

<400> SEQUENCE: 152
ucagugcaug acagaacuug g                                             21

<210> SEQ ID NO 153
<211> LENGTH: 22
<212> TYPE: RNA
<213> ORGANISM: Homo sapiens

<400> SEQUENCE: 153
```

-continued

```
uaaauagagu aggcaaagga ca                                            22

<210> SEQ ID NO 154
<211> LENGTH: 22
<212> TYPE: RNA
<213> ORGANISM: Homo sapiens

<400> SEQUENCE: 154
aaacaaacau ggugcacuuc uu                                            22

<210> SEQ ID NO 155
<211> LENGTH: 21
<212> TYPE: RNA
<213> ORGANISM: Homo sapiens

<400> SEQUENCE: 155
ucugaauugu aagaguuguu a                                             21

<210> SEQ ID NO 156
<211> LENGTH: 80
<212> TYPE: RNA
<213> ORGANISM: Homo sapiens

<400> SEQUENCE: 156
gguaccugag aagagguugu cugugaugag uucgcuuuua uuaaugacga auauaacaca   60
gauggccugu uuucaguacc                                               80

<210> SEQ ID NO 157
<211> LENGTH: 73
<212> TYPE: RNA
<213> ORGANISM: Homo sapiens

<400> SEQUENCE: 157
uuccucaucu auaaaaugag ggcaguaaga ccuuccuucc uugucuuacu accccauuu    60 uauagaugag gaa                                                      73

<210> SEQ ID NO 158
<211> LENGTH: 68
<212> TYPE: RNA
<213> ORGANISM: Homo sapiens

<400> SEQUENCE: 158
gaggcaaagu ucugagacac uccgacucug aguaugauag aagucagugc acuacagaac   60
uuugucuc                                                            68

<210> SEQ ID NO 159
<211> LENGTH: 99
<212> TYPE: RNA
<213> ORGANISM: Homo sapiens

<400> SEQUENCE: 159
caagcacgau uagcauuuga ggugaaguuc uguuauacac ucaggcugug gcucucugaa   60
agucagugca ucacagaacu uugucucgaa agcuuucua                          99

<210> SEQ ID NO 160
<211> LENGTH: 87
<212> TYPE: RNA
<213> ORGANISM: Homo sapiens

<400> SEQUENCE: 160 ugucccccc ggcccagguu cugugauaca cuccgacucg gcucuggag cagucagugc    60
```

```
augacagaac uugggcccgg aaggacc                                              87

<210> SEQ ID NO 161
<211> LENGTH: 77
<212> TYPE: RNA
<213> ORGANISM: Homo sapiens

<400> SEQUENCE: 161
aaaugguuau guccuuugcc uauucuauuu aagacacccu guaccuuaaa uagaguaggc          60
aaaggacaga aacauuu                                                        77

<210> SEQ ID NO 162
<211> LENGTH: 82
<212> TYPE: RNA
<213> ORGANISM: Homo sapiens

<400> SEQUENCE: 162
ugguaccuga aaagaaguug cccauguuau uuucgcuuua uaugugacga aacaaacaug          60
gugcacuucu uuucgguau ca                                                   82

<210> SEQ ID NO 163
<211> LENGTH: 66
<212> TYPE: RNA
<213> ORGANISM: Homo sapiens

<400> SEQUENCE: 163
uauaagaacu cuugcagucu uagauguuau aaaaauauau aucugaauug uaagaguugu         60
uagcac                                                                    66

<210> SEQ ID NO 164
<211> LENGTH: 22
<212> TYPE: RNA
<213> ORGANISM: Homo sapiens

<400> SEQUENCE: 164
uauugcacuu gucccggccu gu                                                  22

<210> SEQ ID NO 165
<211> LENGTH: 22
<212> TYPE: RNA
<213> ORGANISM: Homo sapiens

<400> SEQUENCE: 165
uauugcacuu gucccggccu gu                                                  22

<210> SEQ ID NO 166
<211> LENGTH: 22
<212> TYPE: RNA
<213> ORGANISM: Homo sapiens

<400> SEQUENCE: 166
uagcuuauca gacugauguu ga                                                  22

<210> SEQ ID NO 167
<211> LENGTH: 22
<212> TYPE: RNA
<213> ORGANISM: Homo sapiens

<400> SEQUENCE: 167
uucaaguaau ccaggauagg cu                                                  22
```

```
<210> SEQ ID NO 168
<211> LENGTH: 22
<212> TYPE: RNA
<213> ORGANISM: Homo sapiens

<400> SEQUENCE: 168
uucaaguaau ccaggauagg cu                                              22

<210> SEQ ID NO 169
<211> LENGTH: 23
<212> TYPE: RNA
<213> ORGANISM: Homo sapiens

<400> SEQUENCE: 169
uaaggugcau cuagugcaga uag                                             23

<210> SEQ ID NO 170
<211> LENGTH: 20
<212> TYPE: RNA
<213> ORGANISM: Homo sapiens

<400> SEQUENCE: 170
uaaggcacgc ggugaaugcc                                                 20

<210> SEQ ID NO 171
<211> LENGTH: 20
<212> TYPE: RNA
<213> ORGANISM: Homo sapiens

<400> SEQUENCE: 171
uaaggcacgc ggugaaugcc                                                 20

<210> SEQ ID NO 172
<211> LENGTH: 20
<212> TYPE: RNA
<213> ORGANISM: Homo sapiens

<400> SEQUENCE: 172
uaaggcacgc ggugaaugcc                                                 20

<210> SEQ ID NO 173
<211> LENGTH: 22
<212> TYPE: RNA
<213> ORGANISM: Homo sapiens

<400> SEQUENCE: 173
aacccguaga uccgaucuug ug                                              22

<210> SEQ ID NO 174
<211> LENGTH: 23
<212> TYPE: RNA
<213> ORGANISM: Homo sapiens

<400> SEQUENCE: 174
uguaaacauc cuacacucuc agc                                             23

<210> SEQ ID NO 175
<211> LENGTH: 23
<212> TYPE: RNA
<213> ORGANISM: Homo sapiens

<400> SEQUENCE: 175
cagugcaaua guauugucaa agc                                             23
```

```
<210> SEQ ID NO 176
<211> LENGTH: 23
<212> TYPE: RNA
<213> ORGANISM: Homo sapiens

<400> SEQUENCE: 176
guccaguuuu cccaggaauc ccu                                            23

<210> SEQ ID NO 177
<211> LENGTH: 22
<212> TYPE: RNA
<213> ORGANISM: Homo sapiens

<400> SEQUENCE: 177
ggugcagugc ugcaucucug gu                                             22

<210> SEQ ID NO 178
<211> LENGTH: 23
<212> TYPE: RNA
<213> ORGANISM: Homo sapiens

<400> SEQUENCE: 178
gaagugcuuc gauuuugggg ugu                                            23

<210> SEQ ID NO 179
<211> LENGTH: 23
<212> TYPE: RNA
<213> ORGANISM: Homo sapiens

<400> SEQUENCE: 179
caaagugcuc auagugcagg uag                                            23

<210> SEQ ID NO 180
<211> LENGTH: 22
<212> TYPE: RNA
<213> ORGANISM: Homo sapiens

<400> SEQUENCE: 180
uagcaccauu ugaaaucggu ua                                             22

<210> SEQ ID NO 181
<211> LENGTH: 23
<212> TYPE: RNA
<213> ORGANISM: Homo sapiens

<400> SEQUENCE: 181
uagcaccauu ugaaaucagu guu                                            23

<210> SEQ ID NO 182
<211> LENGTH: 22
<212> TYPE: RNA
<213> ORGANISM: Homo sapiens

<400> SEQUENCE: 182
ugagguagua guuuguacag uu                                             22

<210> SEQ ID NO 183
<211> LENGTH: 22
<212> TYPE: RNA
<213> ORGANISM: Homo sapiens

<400> SEQUENCE: 183
```
ugagguagua gguuguauag uu                    22

<210> SEQ ID NO 184
<211> LENGTH: 22
<212> TYPE: RNA
<213> ORGANISM: Homo sapiens

<400> SEQUENCE: 184
ugagguagua gguugugugg uu                    22

<210> SEQ ID NO 185
<211> LENGTH: 22
<212> TYPE: RNA
<213> ORGANISM: Homo sapiens

<400> SEQUENCE: 185
ugagguagua aguuguauug uu                    22

<210> SEQ ID NO 186
<211> LENGTH: 22
<212> TYPE: RNA
<213> ORGANISM: Homo sapiens

<400> SEQUENCE: 186
cuuucagucg gauguuugca gc                    22

<210> SEQ ID NO 187
<211> LENGTH: 23
<212> TYPE: RNA
<213> ORGANISM: Homo sapiens

<400> SEQUENCE: 187
caaagugcuu acagugcagg uag                   23

<210> SEQ ID NO 188
<211> LENGTH: 22
<212> TYPE: RNA
<213> ORGANISM: Homo sapiens

<400> SEQUENCE: 188
uggaauguaa agaaguaugu au                    22

<210> SEQ ID NO 189
<211> LENGTH: 22
<212> TYPE: RNA
<213> ORGANISM: Homo sapiens

<400> SEQUENCE: 189
uggaauguaa agaaguaugu au                    22

<210> SEQ ID NO 190
<211> LENGTH: 21
<212> TYPE: RNA
<213> ORGANISM: Homo sapiens

<400> SEQUENCE: 190
cugaccuaug aauugacagc c                     21

<210> SEQ ID NO 191
<211> LENGTH: 23
<212> TYPE: RNA
<213> ORGANISM: Homo sapiens

<400> SEQUENCE: 191
uuaaugcuaa ucgugauagg ggu                                              23

<210> SEQ ID NO 192
<211> LENGTH: 23
<212> TYPE: RNA
<213> ORGANISM: Homo sapiens

<400> SEQUENCE: 192
uucucgagga aagaagcacu uuc                                              23

<210> SEQ ID NO 193
<211> LENGTH: 18
<212> TYPE: RNA
<213> ORGANISM: Homo sapiens

<400> SEQUENCE: 193
ugcuuccuuu cagagggu                                                    18

<210> SEQ ID NO 194
<211> LENGTH: 21
<212> TYPE: RNA
<213> ORGANISM: Homo sapiens

<400> SEQUENCE: 194
aggcaagaug cuggcauagc u                                                21

<210> SEQ ID NO 195
<211> LENGTH: 23
<212> TYPE: RNA
<213> ORGANISM: Homo sapiens

<400> SEQUENCE: 195
aacauucaac gcugucggug agu                                              23

<210> SEQ ID NO 196
<211> LENGTH: 23
<212> TYPE: RNA
<213> ORGANISM: Homo sapiens

<400> SEQUENCE: 196
aacauucaac gcugucggug agu                                              23

<210> SEQ ID NO 197
<211> LENGTH: 23
<212> TYPE: RNA
<213> ORGANISM: Homo sapiens

<400> SEQUENCE: 197
aacauucauu gcugucggug ggu                                              23

<210> SEQ ID NO 198
<211> LENGTH: 23
<212> TYPE: RNA
<213> ORGANISM: Homo sapiens

<400> SEQUENCE: 198
aacauucauu gcugucggug ggu                                              23

<210> SEQ ID NO 199
<211> LENGTH: 22
<212> TYPE: RNA
<213> ORGANISM: Homo sapiens

```
-continued

<400> SEQUENCE: 199
aacauucaac cugucgguga gu                                          22

<210> SEQ ID NO 200
<211> LENGTH: 23
<212> TYPE: RNA
<213> ORGANISM: Homo sapiens

<400> SEQUENCE: 200
aggcagugua guuagcugau ugc                                         23

<210> SEQ ID NO 201
<211> LENGTH: 23
<212> TYPE: RNA
<213> ORGANISM: Homo sapiens

<400> SEQUENCE: 201
uaggcagugu cauuagcuga uug                                         23

<210> SEQ ID NO 202
<211> LENGTH: 23
<212> TYPE: RNA
<213> ORGANISM: Homo sapiens

<400> SEQUENCE: 202
agcagcauug uacagggcua uga                                         23

<210> SEQ ID NO 203
<211> LENGTH: 23
<212> TYPE: RNA
<213> ORGANISM: Homo sapiens

<400> SEQUENCE: 203
agcagcauug uacagggcua uga                                         23

<210> SEQ ID NO 204
<211> LENGTH: 22
<212> TYPE: RNA
<213> ORGANISM: Homo sapiens

<400> SEQUENCE: 204
cugugcgugu gacagcggcu ga                                          22

<210> SEQ ID NO 205
<211> LENGTH: 22
<212> TYPE: RNA
<213> ORGANISM: Homo sapiens

<400> SEQUENCE: 205
uagcagcacg uaaauauugg cg                                          22

<210> SEQ ID NO 206
<211> LENGTH: 22
<212> TYPE: RNA
<213> ORGANISM: Homo sapiens

<400> SEQUENCE: 206
uagcagcacg uaaauauugg cg                                          22

<210> SEQ ID NO 207
<211> LENGTH: 22
<212> TYPE: RNA
<213> ORGANISM: Homo sapiens
```

<400> SEQUENCE: 207
uguaaacauc cucgacugga ag                                              22

<210> SEQ ID NO 208
<211> LENGTH: 21
<212> TYPE: RNA
<213> ORGANISM: Homo sapiens

<400> SEQUENCE: 208
aggcaagaug cuggcauagc u                                               21

<210> SEQ ID NO 209
<211> LENGTH: 21
<212> TYPE: RNA
<213> ORGANISM: Homo sapiens

<400> SEQUENCE: 209
agcuacaucu ggcuacuggg u                                               21

<210> SEQ ID NO 210
<211> LENGTH: 23
<212> TYPE: RNA
<213> ORGANISM: Homo sapiens

<400> SEQUENCE: 210
caaagugcuu acagugcagg uag                                             23

<210> SEQ ID NO 211
<211> LENGTH: 22
<212> TYPE: RNA
<213> ORGANISM: Homo sapiens

<400> SEQUENCE: 211
acugcaguga aggcacuugu ag                                              22

<210> SEQ ID NO 212
<211> LENGTH: 22
<212> TYPE: RNA
<213> ORGANISM: Homo sapiens

<400> SEQUENCE: 212
uaauacugcc ugguaaugau ga                                              22

<210> SEQ ID NO 213
<211> LENGTH: 23
<212> TYPE: RNA
<213> ORGANISM: Homo sapiens

<400> SEQUENCE: 213
uaauacugcc ggguaaugau gga                                             23

<210> SEQ ID NO 214
<211> LENGTH: 21
<212> TYPE: RNA
<213> ORGANISM: Homo sapiens

<400> SEQUENCE: 214
ucacagugaa ccggucucuu u                                               21

<210> SEQ ID NO 215
<211> LENGTH: 23
<212> TYPE: RNA

-continued

<213> ORGANISM: Homo sapiens

<400> SEQUENCE: 215
uagcagcggg aacaguucug cag                                           23

<210> SEQ ID NO 216
<211> LENGTH: 22
<212> TYPE: RNA
<213> ORGANISM: Homo sapiens

<400> SEQUENCE: 216
cagcagcaau ucauguuuug aa                                            22

<210> SEQ ID NO 217
<211> LENGTH: 21
<212> TYPE: RNA
<213> ORGANISM: Homo sapiens

<400> SEQUENCE: 217
uagcagcaca gaaauauugg c                                             21

<210> SEQ ID NO 218
<211> LENGTH: 22
<212> TYPE: RNA
<213> ORGANISM: Homo sapiens

<400> SEQUENCE: 218
aggcauugac uucucacuag cu                                            22

<210> SEQ ID NO 219
<211> LENGTH: 22
<212> TYPE: RNA
<213> ORGANISM: Homo sapiens

<400> SEQUENCE: 219
gugaaauguu uaggaccacu ag                                            22

<210> SEQ ID NO 220
<211> LENGTH: 22
<212> TYPE: RNA
<213> ORGANISM: Homo sapiens

<400> SEQUENCE: 220
acaguagucu gcacauuggu ua                                            22

<210> SEQ ID NO 221
<211> LENGTH: 23
<212> TYPE: RNA
<213> ORGANISM: Homo sapiens

<400> SEQUENCE: 221
cccaguguuc agacuaccug uuc                                           23

<210> SEQ ID NO 222
<211> LENGTH: 22
<212> TYPE: RNA
<213> ORGANISM: Homo sapiens

<400> SEQUENCE: 222
acaguagucu gcacauuggu ua                                            22

<210> SEQ ID NO 223
<211> LENGTH: 23

```
<212> TYPE: RNA
<213> ORGANISM: Homo sapiens

<400> SEQUENCE: 223
caaagugcug uucgugcagg uag                                    23

<210> SEQ ID NO 224
<211> LENGTH: 22
<212> TYPE: RNA
<213> ORGANISM: Homo sapiens

<400> SEQUENCE: 224
ugagguagua aguuguauug uu                                     22

<210> SEQ ID NO 225
<211> LENGTH: 24
<212> TYPE: RNA
<213> ORGANISM: Homo sapiens

<400> SEQUENCE: 225
ucccugagac ccuuuaaccu guga                                   24

<210> SEQ ID NO 226
<211> LENGTH: 22
<212> TYPE: RNA
<213> ORGANISM: Homo sapiens

<400> SEQUENCE: 226
uuuggucccc uucaaccagc ug                                     22

<210> SEQ ID NO 227
<211> LENGTH: 22
<212> TYPE: RNA
<213> ORGANISM: Homo sapiens

<400> SEQUENCE: 227
uuuggucccc uucaaccagc ua                                     22

<210> SEQ ID NO 228
<211> LENGTH: 22
<212> TYPE: RNA
<213> ORGANISM: Homo sapiens

<400> SEQUENCE: 228
ucguaccgug aguaauaaug cg                                     22

<210> SEQ ID NO 229
<211> LENGTH: 22
<212> TYPE: RNA
<213> ORGANISM: Homo sapiens

<400> SEQUENCE: 229
uguaacagca acuccaugug ga                                     22

<210> SEQ ID NO 230
<211> LENGTH: 23
<212> TYPE: RNA
<213> ORGANISM: Homo sapiens

<400> SEQUENCE: 230
ugucugcccg caugccugcc ucu                                    23

<210> SEQ ID NO 231
```

```
<211> LENGTH: 22
<212> TYPE: RNA
<213> ORGANISM: Homo sapiens

<400> SEQUENCE: 231
uagcagcaca ucaugguuua ca                                              22

<210> SEQ ID NO 232
<211> LENGTH: 22
<212> TYPE: RNA
<213> ORGANISM: Homo sapiens

<400> SEQUENCE: 232
uccagcauca gugauuuugu ug                                              22

<210> SEQ ID NO 233
<211> LENGTH: 22
<212> TYPE: RNA
<213> ORGANISM: Homo sapiens

<400> SEQUENCE: 233
uccuucauuc caccggaguc ug                                              22

<210> SEQ ID NO 234
<211> LENGTH: 22
<212> TYPE: RNA
<213> ORGANISM: Homo sapiens

<400> SEQUENCE: 234
ucaccagccc uguguucccu ag                                              22

<210> SEQ ID NO 235
<211> LENGTH: 23
<212> TYPE: RNA
<213> ORGANISM: Homo sapiens

<400> SEQUENCE: 235
aaggagcuua caaucuagcu ggg                                             23

<210> SEQ ID NO 236
<211> LENGTH: 22
<212> TYPE: RNA
<213> ORGANISM: Homo sapiens

<400> SEQUENCE: 236
uggcagugua uuguuagcug gu                                              22

<210> SEQ ID NO 237
<211> LENGTH: 22
<212> TYPE: RNA
<213> ORGANISM: Homo sapiens

<400> SEQUENCE: 237
acuggacuua gggucagaag gc                                              22

<210> SEQ ID NO 238
<211> LENGTH: 22
<212> TYPE: RNA
<213> ORGANISM: Homo sapiens

<400> SEQUENCE: 238
uuauaaagca augagacuga uu                                              22
```

<210> SEQ ID NO 239
<211> LENGTH: 23
<212> TYPE: RNA
<213> ORGANISM: Homo sapiens

<400> SEQUENCE: 239
uaaaucccau ggugccuucu ccu                                              23

<210> SEQ ID NO 240
<211> LENGTH: 22
<212> TYPE: RNA
<213> ORGANISM: Homo sapiens

<400> SEQUENCE: 240
aaaaugguuc ccuuuagagu gu                                               22

<210> SEQ ID NO 241
<211> LENGTH: 22
<212> TYPE: RNA
<213> ORGANISM: Homo sapiens

<400> SEQUENCE: 241
aggcggggcg ccgcgggacc gc                                               22

<210> SEQ ID NO 242
<211> LENGTH: 22
<212> TYPE: RNA
<213> ORGANISM: Homo sapiens

<400> SEQUENCE: 242
cagugcaaug uuaaaagggc au                                               22

<210> SEQ ID NO 243
<211> LENGTH: 22
<212> TYPE: RNA
<213> ORGANISM: Homo sapiens

<400> SEQUENCE: 243
cagugcaaug augaaagggc au                                               22

<210> SEQ ID NO 244
<211> LENGTH: 22
<212> TYPE: RNA
<213> ORGANISM: Homo sapiens

<400> SEQUENCE: 244
ucuucucugu uuuggccaug ug                                               22

<210> SEQ ID NO 245
<211> LENGTH: 20
<212> TYPE: RNA
<213> ORGANISM: Homo sapiens

<400> SEQUENCE: 245
guccgcucgg cgguggccca                                                  20

<210> SEQ ID NO 246
<211> LENGTH: 23
<212> TYPE: RNA
<213> ORGANISM: Homo sapiens

<400> SEQUENCE: 246
aucgcugcgg uugcgagcgc ugu                                              23

```
<210> SEQ ID NO 247
<211> LENGTH: 22
<212> TYPE: RNA
<213> ORGANISM: Homo sapiens

<400> SEQUENCE: 247
uggugggccg cagaacaugu gc                                              22

<210> SEQ ID NO 248
<211> LENGTH: 22
<212> TYPE: RNA
<213> ORGANISM: Homo sapiens

<400> SEQUENCE: 248
uucccuuugu cauccuaugc cu                                              22

<210> SEQ ID NO 249
<211> LENGTH: 21
<212> TYPE: RNA
<213> ORGANISM: Homo sapiens

<400> SEQUENCE: 249
caagucacua gugguuccgu u                                               21

<210> SEQ ID NO 250
<211> LENGTH: 22
<212> TYPE: RNA
<213> ORGANISM: Homo sapiens

<400> SEQUENCE: 250
agucauugga ggguuugagc ag                                              22

<210> SEQ ID NO 251
<211> LENGTH: 22
<212> TYPE: RNA
<213> ORGANISM: Homo sapiens

<400> SEQUENCE: 251
uggaguguga caauggucuu ug                                              22

<210> SEQ ID NO 252
<211> LENGTH: 22
<212> TYPE: RNA
<213> ORGANISM: Homo sapiens

<400> SEQUENCE: 252 uauguggau gguaaaccgc uu                                               22

<210> SEQ ID NO 253
<211> LENGTH: 22
<212> TYPE: RNA
<213> ORGANISM: Homo sapiens

<400> SEQUENCE: 253
ugguuuaccg ucccacauac au                                              22

<210> SEQ ID NO 254
<211> LENGTH: 22
<212> TYPE: RNA
<213> ORGANISM: Homo sapiens

<400> SEQUENCE: 254
aacccguaga uccgaacuug ug                                              22
```

<210> SEQ ID NO 255
<211> LENGTH: 23
<212> TYPE: RNA
<213> ORGANISM: Homo sapiens

<400> SEQUENCE: 255
agcugguguu gugaaucagg ccg                                           23

<210> SEQ ID NO 256
<211> LENGTH: 22
<212> TYPE: RNA
<213> ORGANISM: Homo sapiens

<400> SEQUENCE: 256
cagugguuuu acccuauggu ag                                            22

<210> SEQ ID NO 257
<211> LENGTH: 22
<212> TYPE: RNA
<213> ORGANISM: Homo sapiens

<400> SEQUENCE: 257
uuuguucguu cggcucgcgu ga                                            22

<210> SEQ ID NO 258
<211> LENGTH: 23
<212> TYPE: RNA
<213> ORGANISM: Homo sapiens

<400> SEQUENCE: 258
uacugcauca ggaacugauu gga                                           23

<210> SEQ ID NO 259
<211> LENGTH: 23
<212> TYPE: RNA
<213> ORGANISM: Homo sapiens

<400> SEQUENCE: 259
aaagugcugc gacauuugag cgu                                           23

<210> SEQ ID NO 260
<211> LENGTH: 23
<212> TYPE: RNA
<213> ORGANISM: Homo sapiens

<400> SEQUENCE: 260
uuuggcacua gcacauuuuu gcu                                           23

<210> SEQ ID NO 261
<211> LENGTH: 22
<212> TYPE: RNA
<213> ORGANISM: Homo sapiens

<400> SEQUENCE: 261
ucggauccgu cugagcuugg cu                                            22

<210> SEQ ID NO 262
<211> LENGTH: 23
<212> TYPE: RNA
<213> ORGANISM: Homo sapiens

<400> SEQUENCE: 262

```
uauggcuuuu cauuccuaug uga                                          23

<210> SEQ ID NO 263
<211> LENGTH: 21
<212> TYPE: RNA
<213> ORGANISM: Homo sapiens

<400> SEQUENCE: 263
uacaguacug ugauaacuga a                                            21

<210> SEQ ID NO 264
<211> LENGTH: 20
<212> TYPE: RNA
<213> ORGANISM: Homo sapiens

<400> SEQUENCE: 264
ccucugggcc cuuccuccag                                              20

<210> SEQ ID NO 265
<211> LENGTH: 23
<212> TYPE: RNA
<213> ORGANISM: Homo sapiens

<400> SEQUENCE: 265
cgcauccccu agggcauugg ugu                                          23

<210> SEQ ID NO 266
<211> LENGTH: 20
<212> TYPE: RNA
<213> ORGANISM: Homo sapiens

<400> SEQUENCE: 266
acugccccag gugcugcugg                                              20

<210> SEQ ID NO 267
<211> LENGTH: 23
<212> TYPE: RNA
<213> ORGANISM: Homo sapiens

<400> SEQUENCE: 267
ucaagagcaa uaacgaaaaa ugu                                          23

<210> SEQ ID NO 268
<211> LENGTH: 22
<212> TYPE: RNA
<213> ORGANISM: Homo sapiens

<400> SEQUENCE: 268
uaacacuguc ugguaaagau gg                                           22

<210> SEQ ID NO 269
<211> LENGTH: 78
<212> TYPE: RNA
<213> ORGANISM: Homo sapiens

<400> SEQUENCE: 269
cuuucuacac agguugggau cgguugcaau gcuguguuuc uguaugguau ugcacuuguc  60
ccggccuguu gaguuugg                                                78

<210> SEQ ID NO 270
<211> LENGTH: 75
<212> TYPE: RNA
<213> ORGANISM: Homo sapiens
```

-continued

<400> SEQUENCE: 270
ucaucccugg gugggauuu guugcauuac uuguguucua uauaaaguau ugcacuuguc    60
ccggccugug gaaga                                                    75

<210> SEQ ID NO 271
<211> LENGTH: 72
<212> TYPE: RNA
<213> ORGANISM: Homo sapiens

<400> SEQUENCE: 271
ugucggguag cuuaucagac ugauguugac uguugaaucu cauggcaaca ccagucgaug    60
ggcugucuga ca                                                       72

<210> SEQ ID NO 272
<211> LENGTH: 77
<212> TYPE: RNA
<213> ORGANISM: Homo sapiens

<400> SEQUENCE: 272
guggccucgu ucaaguaauc caggauaggc ugugcagguc ccaaugggcc uauucuuggu    60
uacuugcacg gggacgc                                                  77

<210> SEQ ID NO 273
<211> LENGTH: 84
<212> TYPE: RNA
<213> ORGANISM: Homo sapiens

<400> SEQUENCE: 273
ggcuguggcu ggauucaagu aauccaggau aggcuguuuc caucugugag gccuauucuu    60
gauuacuugu uucuggaggc agcu                                          84

<210> SEQ ID NO 274
<211> LENGTH: 71
<212> TYPE: RNA
<213> ORGANISM: Homo sapiens

<400> SEQUENCE: 274
uguucuaagg ugcaucuagu gcagauagug aaguagauua gcaucuacug cccuaagugc    60
uccuucuggc a                                                        71

<210> SEQ ID NO 275
<211> LENGTH: 87
<212> TYPE: RNA
<213> ORGANISM: Homo sapiens

<400> SEQUENCE: 275
ugagggcccc ucugcguguu cacagcggac cuugauuuaa ugucuauaca auuaaggcac    60
gcggugaaug ccaagagagg cgccucc                                       87

<210> SEQ ID NO 276
<211> LENGTH: 85
<212> TYPE: RNA
<213> ORGANISM: Homo sapiens

<400> SEQUENCE: 276
aggccucucu cuccguguuc acagcggacc uugauuuaaa uguccauaca auuaaggcac    60
gcggugaaug ccaagaaugg ggcug                                         85

```
<210> SEQ ID NO 277
<211> LENGTH: 109
<212> TYPE: RNA
<213> ORGANISM: Homo sapiens

<400> SEQUENCE: 277
aucaagauua gaggcucugc ucuccguguu cacagcggac cuugauuuaa ugucauacaa      60
uuaaggcacg cggugaaugc caagagcgga gccuacggcu gcacuugaa                 109

<210> SEQ ID NO 278
<211> LENGTH: 81
<212> TYPE: RNA
<213> ORGANISM: Homo sapiens

<400> SEQUENCE: 278
cccauuggca uaaacccgua gauccgaucu uguggugaag uggaccgcac aagcucgcuu      60
cuaugggucu gugucagugu g                                                81

<210> SEQ ID NO 279
<211> LENGTH: 89
<212> TYPE: RNA
<213> ORGANISM: Homo sapiens

<400> SEQUENCE: 279
accaugcugu agugugugua aacauccuac acucucagcu gugagcucaa gguggcuggg      60
agaggguugu uuacuccuuc ugccaugga                                        89

<210> SEQ ID NO 280
<211> LENGTH: 72
<212> TYPE: RNA
<213> ORGANISM: Homo sapiens

<400> SEQUENCE: 280
agauacugua aacauccuac acucucagcu guggaaagua agaaagcugg gagaaggcug      60
uuuacucuuu cu                                                          72

<210> SEQ ID NO 281
<211> LENGTH: 86
<212> TYPE: RNA
<213> ORGANISM: Homo sapiens

<400> SEQUENCE: 281
acugcuaacg aaugcucuga cuuuauugca cuacuguacu uuacagcuag cagugcaaua      60
guauugucaa agcaucugaa agcagg                                           86

<210> SEQ ID NO 282
<211> LENGTH: 88
<212> TYPE: RNA
<213> ORGANISM: Homo sapiens

<400> SEQUENCE: 282
caccuugucc ucacggucca guuucccag gaaucccuua gaugcuaaga ugggauucc        60 uggaaauacu guucuugagg ucaugguu                                         88

<210> SEQ ID NO 283
<211> LENGTH: 106
<212> TYPE: RNA
<213> ORGANISM: Homo sapiens

<400> SEQUENCE: 283
```
gcgcagcgcc cugucuccca gccugaggug cagugcugca ucucggguca guugggaguc    60
ugagaugaag cacuguagcu caggaagaga gaaguuguuc ugcagc                  106

<210> SEQ ID NO 284
<211> LENGTH: 69
<212> TYPE: RNA
<213> ORGANISM: Homo sapiens

<400> SEQUENCE: 284
gggauacuca aaaugggggc gcuuuccuuu uugucuguac ugggaagugc uucgauuuug    60
ggugucccc                                                           69

<210> SEQ ID NO 285
<211> LENGTH: 69
<212> TYPE: RNA
<213> ORGANISM: Homo sapiens

<400> SEQUENCE: 285
aguaccaaag ugcucauagu gcagguaguu uggcaugac ucacuguag uaugggcacu      60 uccaguacu                                                           69

<210> SEQ ID NO 286
<211> LENGTH: 88
<212> TYPE: RNA
<213> ORGANISM: Homo sapiens

<400> SEQUENCE: 286
aucucuuaca caggcugacc gauuucuccu ggguucaga gucuguuuuu gucuagcacc     60
auuugaaauc gguuaugaug uaggggga                                      88

<210> SEQ ID NO 287
<211> LENGTH: 81
<212> TYPE: RNA
<213> ORGANISM: Homo sapiens

<400> SEQUENCE: 287
cuucaggaag cugguuucau auggugguuu agauuuaaau agugauuguc uagcaccauu    60
ugaaaucagu guucuugggg g                                             81

<210> SEQ ID NO 288
<211> LENGTH: 81
<212> TYPE: RNA
<213> ORGANISM: Homo sapiens

<400> SEQUENCE: 288
cuucuggaag cugguuucac auggugggcuu agauuuuucc aucuuuguau cuagcaccau   60
uugaaaucag uguuuuagga g                                             81

<210> SEQ ID NO 289
<211> LENGTH: 84
<212> TYPE: RNA
<213> ORGANISM: Homo sapiens

<400> SEQUENCE: 289
aggcugaggu aguaguuugu acaguuugag ggucuaugau accacccggu acaggagaua    60
acuguacagg ccacugccuu gcca                                          84

<210> SEQ ID NO 290

```
<211> LENGTH: 80
<212> TYPE: RNA
<213> ORGANISM: Homo sapiens

<400> SEQUENCE: 290
ugggaugagg uaguagguug uauaguuuua gggucacacc caccacuggg agauaacuau      60
acaaucuacu gucuuuccua                                                  80

<210> SEQ ID NO 291
<211> LENGTH: 72
<212> TYPE: RNA
<213> ORGANISM: Homo sapiens

<400> SEQUENCE: 291
agguugaggu aguagguugu auaguuuaga auuacaucaa gggagauaac uguacagccu      60
ccuagcuuuc cu                                                          72

<210> SEQ ID NO 292
<211> LENGTH: 74
<212> TYPE: RNA
<213> ORGANISM: Homo sapiens

<400> SEQUENCE: 292
gggugaggua guagguugua uaguuugggg cucugcccug cuagggaua acuauacaau       60 cuacugucuu uccu                                                        74

<210> SEQ ID NO 293
<211> LENGTH: 83
<212> TYPE: RNA
<213> ORGANISM: Homo sapiens

<400> SEQUENCE: 293
cggggugagg uaguagguug ugggguuuca gggcagugau guugcccuc ggaagauaac       60 uauacaaccu acugccuucc cug                                              83

<210> SEQ ID NO 294
<211> LENGTH: 119
<212> TYPE: RNA
<213> ORGANISM: Homo sapiens

<400> SEQUENCE: 294
aggauucugc ucaugccagg gugagguagu aaguuguauu guugugggu agggauauua       60 ggccccaauu agaagauaac uauacaacuu acuacuuucc cuggugugug gcauauuca      119

<210> SEQ ID NO 295
<211> LENGTH: 71
<212> TYPE: RNA
<213> ORGANISM: Homo sapiens

<400> SEQUENCE: 295
gcgacuguaa acauccucga cuggaagcug ugaagccaca gaugggcuuu cagucggaug      60
uuugcagcug c                                                           71

<210> SEQ ID NO 296
<211> LENGTH: 84
<212> TYPE: RNA
<213> ORGANISM: Homo sapiens

<400> SEQUENCE: 296
gucagaauaa ugucaaagug cuuacagugc agguagugau augugcaucu acugcaguga      60
```

```
aggcacuugu agcauuaugg ugac                                          84

<210> SEQ ID NO 297
<211> LENGTH: 71
<212> TYPE: RNA
<213> ORGANISM: Homo sapiens

<400> SEQUENCE: 297
ugggaaacau acuucuuuau augcccauau ggaccugcua agcuauggaa uguaaagaag    60
uauguaucuc a                                                        71

<210> SEQ ID NO 298
<211> LENGTH: 85
<212> TYPE: RNA
<213> ORGANISM: Homo sapiens

<400> SEQUENCE: 298
accuacucag aguacauacu ucuuuaugua cccauaugaa cauacaaugc uauggaaugu    60
aaagaaguau guauuuuugg uaggc                                         85

<210> SEQ ID NO 299
<211> LENGTH: 110
<212> TYPE: RNA
<213> ORGANISM: Homo sapiens

<400> SEQUENCE: 299
gccgagaccg agugcacagg gcucugaccu augaauugac agccagugcu cucgucuccc    60
cucuggcugc caauuccaua ggucacaggu auguucgccu caaugccagc               110

<210> SEQ ID NO 300
<211> LENGTH: 65
<212> TYPE: RNA
<213> ORGANISM: Homo sapiens

<400> SEQUENCE: 300
cuguuaaugc uaaucgugau aggggguuuuu gccuccaacu gacuccuaca uauuagcauu    60
aacag                                                               65

<210> SEQ ID NO 301
<211> LENGTH: 90
<212> TYPE: RNA
<213> ORGANISM: Homo sapiens

<400> SEQUENCE: 301
ucucaggcug ugaccuucuc gaggaaagaa gcacuuucug uugucugaaa gaaaagaaag    60
ugcuuccuuu cagaggguua cgguuugaga                                    90

<210> SEQ ID NO 302
<211> LENGTH: 90
<212> TYPE: RNA
<213> ORGANISM: Homo sapiens

<400> SEQUENCE: 302
ucucagguug ugaccuucuc gaggaaagaa gcacuuucug uugucugaaa gaaaagaaag    60
ugcuuccuuu cagaggguua cgguuugaga                                    90

<210> SEQ ID NO 303
<211> LENGTH: 71
<212> TYPE: RNA
```

<213> ORGANISM: Homo sapiens

<400> SEQUENCE: 303
ggagaggagg caagaugcug gcauagcugu ugaacuggga accugcuaug ccaacauauu    60
gccaucuuuc c    71

<210> SEQ ID NO 304
<211> LENGTH: 110
<212> TYPE: RNA
<213> ORGANISM: Homo sapiens

<400> SEQUENCE: 304
ugaguuuuga gguugcuuca gugaacauuc aacgcugucg gugaguuugg aauuaaaauc    60
aaaaccaucg accguugauu guacccuaug gcuaaccauc aucuacucca    110

<210> SEQ ID NO 305
<211> LENGTH: 110
<212> TYPE: RNA
<213> ORGANISM: Homo sapiens

<400> SEQUENCE: 305
agaagggcua ucaggccagc cuucagagga cuccaaggaa cauucaacgc ugucggugag    60
uuugggauuu gaaaaaacca cugaccguug acuguaccuu ggggguccuua    110

<210> SEQ ID NO 306
<211> LENGTH: 110
<212> TYPE: RNA
<213> ORGANISM: Homo sapiens

<400> SEQUENCE: 306
ccugugcaga gauuauuuuu uaaaaggguca caaucaacau ucauugcugu cggugggguug    60 aacugugugg acaagcucac ugaacaauga augcaacugu ggccccgcuu    110

<210> SEQ ID NO 307
<211> LENGTH: 89
<212> TYPE: RNA
<213> ORGANISM: Homo sapiens

<400> SEQUENCE: 307
cugauggcug cacucaacau ucauugcugu cgguggguuu gagucugaau caacucacug    60
aucaaugaau gcaaacugcg gaccaaaca    89

<210> SEQ ID NO 308
<211> LENGTH: 110
<212> TYPE: RNA
<213> ORGANISM: Homo sapiens

<400> SEQUENCE: 308
cggaaaauuu gccaagggu uggggggaaca uucaaccugu cggugaguuu gggcagcuca    60
ggcaaaccau cgaccguuga guggacccug aggccuggaa uugccauccu    110

<210> SEQ ID NO 309
<211> LENGTH: 77
<212> TYPE: RNA
<213> ORGANISM: Homo sapiens

<400> SEQUENCE: 309
agucuaguua cuaggcagug uaguuagcug auugcuaaua guaccaauca cuaaccacac    60
ggccagguaa aaagauu    77

<210> SEQ ID NO 310
<211> LENGTH: 84
<212> TYPE: RNA
<213> ORGANISM: Homo sapiens

<400> SEQUENCE: 310
gugcucgguu uguaggcagu gucauuagcu gauuguacug uggugguuac aaucacuaac        60
uccacugcca ucaaaacaag gcac                                              84

<210> SEQ ID NO 311
<211> LENGTH: 78
<212> TYPE: RNA
<213> ORGANISM: Homo sapiens

<400> SEQUENCE: 311
uacugcccuc ggcuucuuua cagugcugcc uuguugcaua uggaucaagc agcauuguac        60
agggcuauga aggcauug                                                     78

<210> SEQ ID NO 312
<211> LENGTH: 78
<212> TYPE: RNA
<213> ORGANISM: Homo sapiens

<400> SEQUENCE: 312
uugugcuuuc agcuucuuua cagugcugcc uuguagcauu caggucaagc agcauuguac        60
agggcuauga aagaacca                                                     78

<210> SEQ ID NO 313
<211> LENGTH: 110
<212> TYPE: RNA
<213> ORGANISM: Homo sapiens

<400> SEQUENCE: 313
acccggcagu gccuccaggc gcagggcagc cccugcccac cgcacacugc gcugcoccag        60 acccacugug cgugugacag cggcugaucu ugccugggc agcgcgaccc                  110

<210> SEQ ID NO 314
<211> LENGTH: 89
<212> TYPE: RNA
<213> ORGANISM: Homo sapiens

<400> SEQUENCE: 314
gucagcagug ccuuagcagc acguaaauau uggcguuaag auucuaaaau uaucuccagu        60
auuaacugug cugcugaagu aagguugac                                         89

<210> SEQ ID NO 315
<211> LENGTH: 81
<212> TYPE: RNA
<213> ORGANISM: Homo sapiens

<400> SEQUENCE: 315
guuccacucu agcagcacgu aaauauuggc guagugaaau auauauuaaa caccaauauu        60
acugugcugc uuuaguguga c                                                 81

<210> SEQ ID NO 316
<211> LENGTH: 71
<212> TYPE: RNA
<213> ORGANISM: Homo sapiens

<400> SEQUENCE: 316
gcgacuguaa acauccucga cuggaagcug ugaagccaca gaugggcuuu cagucggaug    60
uuugcagcug c                                                        71

<210> SEQ ID NO 317
<211> LENGTH: 71
<212> TYPE: RNA
<213> ORGANISM: Homo sapiens

<400> SEQUENCE: 317
ggagaggagg caagaugcug gcauagcugu ugaacuggga accugcuaug ccaacauauu    60
gccaucuuuc c                                                        71

<210> SEQ ID NO 318
<211> LENGTH: 110
<212> TYPE: RNA
<213> ORGANISM: Homo sapiens

<400> SEQUENCE: 318
gcugcuggaa gguguaggua cccucaaugg cucaguagcc aguguagauc cugucuuucg    60
uaaucagcag cuacaucugg cuacugggguc ucgauggca ucuucuagcu              110

<210> SEQ ID NO 319
<211> LENGTH: 84
<212> TYPE: RNA
<213> ORGANISM: Homo sapiens

<400> SEQUENCE: 319
gucagaauaa ugucaaagug cuuacagugc agguagugau augugcaucu acugcaguga    60
aggcacuugu agcauuaugg ugac                                          84

<210> SEQ ID NO 320
<211> LENGTH: 84
<212> TYPE: RNA
<213> ORGANISM: Homo sapiens

<400> SEQUENCE: 320
gucagaauaa ugucaaagug cuuacagugc agguagugau augugcaucu acugcaguga    60
aggcacuugu agcauuaugg ugac                                          84

<210> SEQ ID NO 321
<211> LENGTH: 95
<212> TYPE: RNA
<213> ORGANISM: Homo sapiens

<400> SEQUENCE: 321
ccagcucggg cagccguggc caucuuacug ggcagcauug gauggaguca ggucucuaau    60
acugccuggu aaugaugacg gcggagcccu gcacg                              95

<210> SEQ ID NO 322
<211> LENGTH: 68
<212> TYPE: RNA
<213> ORGANISM: Homo sapiens

<400> SEQUENCE: 322
cccucgucuu acccagcagu guuggggugc gguuggagu cucuaauacu gccggguaau     60
gauggagg                                                            68

```
<210> SEQ ID NO 323
<211> LENGTH: 82
<212> TYPE: RNA
<213> ORGANISM: Homo sapiens

<400> SEQUENCE: 323
ugagcuguug gauucggggc cguagcacug ucugagaggu uuacauuucu cacagugaac    60
cggucucuuu uucagcugcu uc                                            82

<210> SEQ ID NO 324
<211> LENGTH: 84
<212> TYPE: RNA
<213> ORGANISM: Homo sapiens

<400> SEQUENCE: 324
ugugcagugg aaggggggc cgauacacug uacgagagug aguagcaggu cucacaguga    60
accggucucu uucccuacug uguc                                          84

<210> SEQ ID NO 325
<211> LENGTH: 71
<212> TYPE: RNA
<213> ORGANISM: Homo sapiens

<400> SEQUENCE: 325
ugcccuagca gcgggaacag uucugcagug agcgaucggu gcucugggu auuguuccg     60 cugccagggu a                                                        71

<210> SEQ ID NO 326
<211> LENGTH: 98
<212> TYPE: RNA
<213> ORGANISM: Homo sapiens

<400> SEQUENCE: 326
cgaggggaua cagcagcaau ucauguuuug aaguguucua aaugguucaa aacgugaggc    60
gcugcuauac ccccucgugg ggaagguaga aggugggg                           98

<210> SEQ ID NO 327
<211> LENGTH: 87
<212> TYPE: RNA
<213> ORGANISM: Homo sapiens

<400> SEQUENCE: 327
agcuucccug gcucuagcag cacagaaaua uuggcacagg gaagcgaguc ugccaauauu    60
ggcugugcug cuccaggcag gguggug                                       87

<210> SEQ ID NO 328
<211> LENGTH: 119
<212> TYPE: RNA
<213> ORGANISM: Homo sapiens

<400> SEQUENCE: 328
agucagccug uugaagcuuu gaagcuuuga ugccaggcau ugacuucuca cuagcuguga    60
aaguccuagc uaaagagaag ucaaugcaug acaucuuguu ucaauagaug gcuguuuca   119

<210> SEQ ID NO 329
<211> LENGTH: 110
<212> TYPE: RNA
<213> ORGANISM: Homo sapiens

<400> SEQUENCE: 329
```

```
guguugggga cucgcgcgcu ggguccagug guucuuaaca guucaacagu ucguuagcgc    60
aauugugaaa uguuuaggac cacuagaccc ggcgggcgcg gcgacagcga              110
```

<210> SEQ ID NO 330
<211> LENGTH: 71
<212> TYPE: RNA
<213> ORGANISM: Homo sapiens

<400> SEQUENCE: 330

```
gccaacccag uguucagacu accuguucag gaggcucuca auguguacag uagucugcac    60
auugguuagg c                                                         71
```

<210> SEQ ID NO 331
<211> LENGTH: 71
<212> TYPE: RNA
<213> ORGANISM: Homo sapiens

<400> SEQUENCE: 331

```
gccaacccag uguucagacu accuguucag gaggcucuca auguguacag uagucugcac    60
auugguuagg c                                                         71
```

<210> SEQ ID NO 332
<211> LENGTH: 110
<212> TYPE: RNA
<213> ORGANISM: Homo sapiens

<400> SEQUENCE: 332

```
ccagaggaca ccuccacucc gucuacccag uguuuagacu aucguucag gacucccaaa     60 uuguacagua gucugcacau ugguuaggcu gggcuggguu agacccucgg              110
```

<210> SEQ ID NO 333
<211> LENGTH: 80
<212> TYPE: RNA
<213> ORGANISM: Homo sapiens

<400> SEQUENCE: 333

```
cuggggcuc caaagugcug uucgugcagg uagugugauu acccaaccua cugcugagcu     60
agcacuuccc gagccccggg                                                80
```

<210> SEQ ID NO 334
<211> LENGTH: 119
<212> TYPE: RNA
<213> ORGANISM: Homo sapiens

<400> SEQUENCE: 334

```
aggauucugc ucaugccagg gugagguagu aaguuguauu guuggggu agggauauua      60 ggccccaauu agaagauaac uauacaacuu acuacuuucc cuggugugug gcauauuca    119
```

<210> SEQ ID NO 335
<211> LENGTH: 86
<212> TYPE: RNA
<213> ORGANISM: Homo sapiens

<400> SEQUENCE: 335

```
ugccagucuc uaggucccug agacccuuua accugugagg acauccaggg ucacagguga    60
gguucuuggg agccuggcgu cuggcc                                         86
```

<210> SEQ ID NO 336
<211> LENGTH: 88

```
<212> TYPE: RNA
<213> ORGANISM: Homo sapiens

<400> SEQUENCE: 336
acaaugcuuu gcuagagcug guaaaaugga accaaaucgc cucuucaaug gauuuggucc      60
ccuucaacca gcuguagcua ugcauuga                                         88

<210> SEQ ID NO 337
<211> LENGTH: 102
<212> TYPE: RNA
<213> ORGANISM: Homo sapiens

<400> SEQUENCE: 337
gggagccaaa ugcuuugcua gagcugguaa aauggaacca aaucgacugu ccaauggauu      60
ugguccccuu caaccagcug uagcugugca uugauggcgc cg                        102

<210> SEQ ID NO 338
<211> LENGTH: 119
<212> TYPE: RNA
<213> ORGANISM: Homo sapiens

<400> SEQUENCE: 338
ccucagaaga aagaugcccc cugcucuggc uggucaaacg gaaccaaguc cgucuuccug      60
agagguuugg uccccuucaa ccagcuacag cagggcuggc aaugcccagu ccuuggaga     119

<210> SEQ ID NO 339
<211> LENGTH: 85
<212> TYPE: RNA
<213> ORGANISM: Homo sapiens

<400> SEQUENCE: 339
cgcuggcgac gggacauuau uacuuuuggu acgcgcugug acacuucaaa cucguaccgu      60
gaguaauaau gcgccguccu cggca                                            85

<210> SEQ ID NO 340
<211> LENGTH: 85
<212> TYPE: RNA
<213> ORGANISM: Homo sapiens

<400> SEQUENCE: 340
augguguuau caaguguaac agcaacucca uguggacugu guaccaauuu ccaguggaga      60
ugcuguuacu uuugaugguu accaa                                            85

<210> SEQ ID NO 341
<211> LENGTH: 85
<212> TYPE: RNA
<213> ORGANISM: Homo sapiens

<400> SEQUENCE: 341
ugguucccgc cccuguaac agcaacucca uguggaagug cccacugguu caguggggc       60 ugcuguuauc uggggcgagg gccag                                            85

<210> SEQ ID NO 342
<211> LENGTH: 95
<212> TYPE: RNA
<213> ORGANISM: Homo sapiens

<400> SEQUENCE: 342
ggucucugug uugggcgucu gucugcccgc augccugccu cucguugcu cugaaggagg       60
```
caggggcugg gccugcagcu gccugggcag agcgg     95

<210> SEQ ID NO 343
<211> LENGTH: 98
<212> TYPE: RNA
<213> ORGANISM: Homo sapiens

<400> SEQUENCE: 343
uugaggccuu aaaguacugu agcagcacau caugguuuac augcuacagu caagaugcga     60
aucauuauuu gcugcucuag aaauuuaagg aaauucau     98

<210> SEQ ID NO 344
<211> LENGTH: 67
<212> TYPE: RNA
<213> ORGANISM: Homo sapiens

<400> SEQUENCE: 344
ucuccaacaa uauccuggug cugagugaug acucaggcga cuccagcauc agugauuuug     60
uugaaga     67

<210> SEQ ID NO 345
<211> LENGTH: 110
<212> TYPE: RNA
<213> ORGANISM: Homo sapiens

<400> SEQUENCE: 345
aaagauccuc agacaaucca ugugcuucuc uuguccuuca uuccaccgga gucugucuca     60
uacccaacca gauuucagug gagugaaguu caggaggcau ggagcugaca     110

<210> SEQ ID NO 346
<211> LENGTH: 75
<212> TYPE: RNA
<213> ORGANISM: Homo sapiens

<400> SEQUENCE: 346
gugagggcau gcaggccugg auggggcagc ugggaugguc caaaagggug gccucaccag     60
cccuguguuc ccuag     75

<210> SEQ ID NO 347
<211> LENGTH: 88
<212> TYPE: RNA
<213> ORGANISM: Homo sapiens

<400> SEQUENCE: 347
aacugcccuc aaggagcuua caaucuagcu gggguaaau gacuugcaca ugaacacaac     60
uagacuguga gcuucuagag ggcaggga     88

<210> SEQ ID NO 348
<211> LENGTH: 91
<212> TYPE: RNA
<213> ORGANISM: Homo sapiens

<400> SEQUENCE: 348
cuguguguga ugagcuggca guguauuguu agcugguuga auaugugaau ggcaucggcu     60
aacaugcaac ugcugucuua uugcauauac a     91

<210> SEQ ID NO 349
<211> LENGTH: 90
<212> TYPE: RNA
<213> ORGANISM: Homo sapiens

```
<400> SEQUENCE: 349
gagagaagca cuggacuuag ggucagaagg ccugagucuc ucugcugcag augggcucuc      60
ugucccugag ccaagcuuug uccucccugg                                      90

<210> SEQ ID NO 350
<211> LENGTH: 95
<212> TYPE: RNA
<213> ORGANISM: Homo sapiens

<400> SEQUENCE: 350
uuguaccugg ugugauuaua aagcaaugag acugauuguc auaugucguu uguggggaucc     60 gucucaguua cuuuauagcc auaccuggua ucuua                                95

<210> SEQ ID NO 351
<211> LENGTH: 83
<212> TYPE: RNA
<213> ORGANISM: Homo sapiens

<400> SEQUENCE: 351
gcccuagcuu gguucuaaau cccaugguge cuucuccuug ggaaaaacag agaaggcacu      60
augagauuua gaaucaaguu agg                                             83

<210> SEQ ID NO 352
<211> LENGTH: 87
<212> TYPE: RNA
<213> ORGANISM: Homo sapiens

<400> SEQUENCE: 352
ucucaggcug ugucccucua gagggaagcg cuuucuguug ucugaaagaa aagaaaaugg      60
uucccuuuag aguguuacgc uuugaga                                         87

<210> SEQ ID NO 353
<211> LENGTH: 93
<212> TYPE: RNA
<213> ORGANISM: Homo sapiens

<400> SEQUENCE: 353
ccuuccggcg ucccaggcgg ggcgccgcgg gaccgcccuc gugucugugg cggugggauc      60
ccgcggccgu guuuuccugg uggcccggcc aug                                  93

<210> SEQ ID NO 354
<211> LENGTH: 89
<212> TYPE: RNA
<213> ORGANISM: Homo sapiens

<400> SEQUENCE: 354
ugcugcuggc cagagcucuu uucacauugu gcuacugucu gcaccuguca cuagcagugc     60
aauguuaaaa gggcauuggc cguguagug                                       89

<210> SEQ ID NO 355
<211> LENGTH: 82
<212> TYPE: RNA
<213> ORGANISM: Homo sapiens

<400> SEQUENCE: 355
ggccugcccg acacucuuuc ccuguugcac uacuauaggc cgcugggaag cagugcaaug     60
augaaagggc aucggucagg uc                                              82
```

```
<210> SEQ ID NO 356
<211> LENGTH: 86
<212> TYPE: RNA
<213> ORGANISM: Homo sapiens

<400> SEQUENCE: 356
auuaggagag uaucuucucu guuuuggcca ugugguacu cacagcccu cacacauggc      60 cgaaacagag aaguuacuuu ccuaau                                         86

<210> SEQ ID NO 357
<211> LENGTH: 95
<212> TYPE: RNA
<213> ORGANISM: Homo sapiens

<400> SEQUENCE: 357
gucgaggccg uggcccggaa guggucgggg ccgcugcggg cggaagggcg ccugugcuuc    60
guccgcucgg cgguggccca gccaggcccg cggga                               95

<210> SEQ ID NO 358
<211> LENGTH: 98
<212> TYPE: RNA
<213> ORGANISM: Homo sapiens

<400> SEQUENCE: 358
uggccgacgg ggcgcgcgcg gccuggaggg gcggggcgga cgcagagccg cguuuagucu    60
aucgcugcgg uugcgagcgc uguagggagc cugugcug                            98

<210> SEQ ID NO 359
<211> LENGTH: 81
<212> TYPE: RNA
<213> ORGANISM: Homo sapiens

<400> SEQUENCE: 359
ggguaagugg aaagauggug ggccgcagaa caugcucuga guucgugcca uaugucugcu    60
gaccaucacc uuuagaagcc c                                              81

<210> SEQ ID NO 360
<211> LENGTH: 110
<212> TYPE: RNA
<213> ORGANISM: Homo sapiens

<400> SEQUENCE: 360
ggcuacaguc uuucuucaug ugacucgugg acuucccuuu gucauccuau gccugagaau    60
auaugaagga ggcugggaag gcaaagggac guucaauugu caucacuggc              110

<210> SEQ ID NO 361
<211> LENGTH: 81
<212> TYPE: RNA
<213> ORGANISM: Homo sapiens

<400> SEQUENCE: 361
gggcuuucaa gucacuagug guuccguuua guagaugauu ugcauuguu ucaaaauggu     60 gcccuaguga cuacaaagcc c                                              81

<210> SEQ ID NO 362
<211> LENGTH: 97
<212> TYPE: RNA
<213> ORGANISM: Homo sapiens

<400> SEQUENCE: 362
```
uuagguaauu ccuccacuca aaacccuuca gugacuucca ugacaugaaa uaggaaguca    60 uuggagggúu ugagcagagg aaugaccugu uuuaaaa    97

<210> SEQ ID NO 363
<211> LENGTH: 85
<212> TYPE: RNA
<213> ORGANISM: Homo sapiens

<400> SEQUENCE: 363
ccuuagcaga gcuguggagu gugacaaugg uguuugguc uaaacuauca aacgccauua    60
ucacacuaaa uagcuacugc uaggc    85

<210> SEQ ID NO 364
<211> LENGTH: 63
<212> TYPE: RNA
<213> ORGANISM: Homo sapiens

<400> SEQUENCE: 364
aagaaauggu uuaccguccc acauacauuu ugaauaugua gugggaugg uaaaccgcuu    60 cuu    63

<210> SEQ ID NO 365
<211> LENGTH: 80
<212> TYPE: RNA
<213> ORGANISM: Homo sapiens

<400> SEQUENCE: 365
ccuguugcca caaacccgua gauccgaacu ugugguauua guccgcacaa gcuuguaucu    60
auagguaugu gucuguuagg    80

<210> SEQ ID NO 366
<211> LENGTH: 99
<212> TYPE: RNA
<213> ORGANISM: Homo sapiens

<400> SEQUENCE: 366
cccuggcaug guguggúggg gcagcuggug uugugaauca ggccguugcc aaucagagaa    60
cggcuacuuc acaacaccag ggccacacca cacuacagg    99

<210> SEQ ID NO 367
<211> LENGTH: 100
<212> TYPE: RNA
<213> ORGANISM: Homo sapiens

<400> SEQUENCE: 367
ugugucucuc ucuguguccu gccaguggúu uuacccuaug guagguuacg ucaugcuguu    60
cuaccacagg guagaaccac ggacaggaua ccggggcacc    100

<210> SEQ ID NO 368
<211> LENGTH: 64
<212> TYPE: RNA
<213> ORGANISM: Homo sapiens

<400> SEQUENCE: 368
ccccgcgacg agccccucgc acaaaccgga ccugagcguu uuguucguuc ggcucgcgug    60
aggc    64

<210> SEQ ID NO 369

```
<211> LENGTH: 110
<212> TYPE: RNA
<213> ORGANISM: Homo sapiens

<400> SEQUENCE: 369
aguauaauua uuacauaguu uuugaugucg cagauacugc aucaggaacu gauuggauaa      60
gaaucaguca ccaucaguuc cuaaugcauu gccuucagca ucuaaacaag                110

<210> SEQ ID NO 370
<211> LENGTH: 67
<212> TYPE: RNA
<213> ORGANISM: Homo sapiens

<400> SEQUENCE: 370
gugggccuca aaugugga gc acuauucuga uguccaagug gaaagugcug cgacauuuga     60
gcgucac                                                                67

<210> SEQ ID NO 371
<211> LENGTH: 78
<212> TYPE: RNA
<213> ORGANISM: Homo sapiens

<400> SEQUENCE: 371
uggccgauuu uggcacuagc acauuuuugc uugugucucu ccgcucugag caaucaugug      60
cagugccaau augggaaa                                                    78

<210> SEQ ID NO 372
<211> LENGTH: 97
<212> TYPE: RNA
<213> ORGANISM: Homo sapiens

<400> SEQUENCE: 372
ugugaucacu gucuccagcc ugcugaagcu cagagggcuc ugauucagaa agaucaucgg      60
auccgucuga gcuuggcugg ucggaagucu caucauc                               97

<210> SEQ ID NO 373
<211> LENGTH: 97
<212> TYPE: RNA
<213> ORGANISM: Homo sapiens

<400> SEQUENCE: 373
cacucugcug uggccuaugg cuuuucauuc cuaugugauu gcugucccaa acucauguag      60
ggcuaaaagc caugggcuac agugaggggc gagcucc                               97

<210> SEQ ID NO 374
<211> LENGTH: 75
<212> TYPE: RNA
<213> ORGANISM: Homo sapiens

<400> SEQUENCE: 374
ugcccuggcu caguuaucac agugcugaug cugucuauuc uaaagguaca guacugau       60 aacugaagga uggca                                                       75

<210> SEQ ID NO 375
<211> LENGTH: 79
<212> TYPE: RNA
<213> ORGANISM: Homo sapiens

<400> SEQUENCE: 375 acugucccuuu uucgguuauc augguaccga ugcuguauau cugaaaggua caguacugug    60
```

-continued

```
auaacugaag aaugguggu                                              79

<210> SEQ ID NO 376
<211> LENGTH: 95
<212> TYPE: RNA
<213> ORGANISM: Homo sapiens

<400> SEQUENCE: 376
cucaucuguc uguugggcug gaggcagggc cuuugugaag gcgggugguig cucagaucgc   60 cucugggccc uuccuccagc cccgaggcgg auuca                              95

<210> SEQ ID NO 377
<211> LENGTH: 83
<212> TYPE: RNA
<213> ORGANISM: Homo sapiens

<400> SEQUENCE: 377
cugacuaugc cuccccgcau ccccuagggc auugguguaa agcuggagac ccacugcccc   60
aggugcugcu gggggiuugua guc                                          83

<210> SEQ ID NO 378
<211> LENGTH: 83
<212> TYPE: RNA
<213> ORGANISM: Homo sapiens

<400> SEQUENCE: 378
cugacuaugc cuccccgcau ccccuagggc auugguguaa agcuggagac ccacugcccc   60
aggugcugcu gggggiuugua guc                                          83

<210> SEQ ID NO 379
<211> LENGTH: 94
<212> TYPE: RNA
<213> ORGANISM: Homo sapiens

<400> SEQUENCE: 379
uguuuugagc gggggucaag agcaauaacg aaaaauguuu gucauaaacc guuuuucauu   60
auugcuccug accuccucuc auuugcuaua uuca                               94

<210> SEQ ID NO 380
<211> LENGTH: 95
<212> TYPE: RNA
<213> ORGANISM: Homo sapiens

<400> SEQUENCE: 380
cggccggccc uggguccauc uuccaguaca guguuggaug gucuaauugu gaagcuccua   60
acacugucug guaaagaugg cucccggguig gguuc                             95

<210> SEQ ID NO 381
<211> LENGTH: 17
<212> TYPE: RNA
<213> ORGANISM: Homo sapiens

<400> SEQUENCE: 381 guggggaga ggcuguc                                                   17

<210> SEQ ID NO 382
<211> LENGTH: 22
<212> TYPE: RNA
<213> ORGANISM: Homo sapiens
```

```
<400> SEQUENCE: 382
ugcaacgaac cugagccacu ga                                     22

<210> SEQ ID NO 383
<211> LENGTH: 22
<212> TYPE: RNA
<213> ORGANISM: Homo sapiens

<400> SEQUENCE: 383
uagguuaucc guguugccuu cg                                     22

<210> SEQ ID NO 384
<211> LENGTH: 21
<212> TYPE: RNA
<213> ORGANISM: Homo sapiens

<400> SEQUENCE: 384
gugccagcug cagugggga g                                       21

<210> SEQ ID NO 385
<211> LENGTH: 20
<212> TYPE: RNA
<213> ORGANISM: Homo sapiens

<400> SEQUENCE: 385
guccgcucgg cgguggccca                                        20

<210> SEQ ID NO 386
<211> LENGTH: 23
<212> TYPE: RNA
<213> ORGANISM: Homo sapiens

<400> SEQUENCE: 386
ccaguuaccg cuuccgcuac cgc                                    23

<210> SEQ ID NO 387
<211> LENGTH: 17
<212> TYPE: RNA
<213> ORGANISM: Homo sapiens

<400> SEQUENCE: 387
acauugccag ggaguuu                                           17

<210> SEQ ID NO 388
<211> LENGTH: 22
<212> TYPE: RNA
<213> ORGANISM: Homo sapiens

<400> SEQUENCE: 388
uugcauaguc acaaaaguga uc                                     22

<210> SEQ ID NO 389
<211> LENGTH: 17
<212> TYPE: RNA
<213> ORGANISM: Homo sapiens

<400> SEQUENCE: 389
uugucugcug aguuucc                                           17

<210> SEQ ID NO 390
<211> LENGTH: 23
<212> TYPE: RNA
<213> ORGANISM: Homo sapiens
```

```
-continued

<400> SEQUENCE: 390
agguuacccg agcaacuuug cau                                            23

<210> SEQ ID NO 391
<211> LENGTH: 22
<212> TYPE: RNA
<213> ORGANISM: Homo sapiens

<400> SEQUENCE: 391
ugggucuuug cgggcgagau ga                                             22

<210> SEQ ID NO 392
<211> LENGTH: 19
<212> TYPE: RNA
<213> ORGANISM: Homo sapiens

<400> SEQUENCE: 392
aagugugcag ggcacuggu                                                 19

<210> SEQ ID NO 393
<211> LENGTH: 22
<212> TYPE: RNA
<213> ORGANISM: Homo sapiens

<400> SEQUENCE: 393
uaaugccccu aaaaauccuu au                                             22

<210> SEQ ID NO 394
<211> LENGTH: 23
<212> TYPE: RNA
<213> ORGANISM: Homo sapiens

<400> SEQUENCE: 394
uaauccuugc uaccugggug aga                                            23

<210> SEQ ID NO 395
<211> LENGTH: 22
<212> TYPE: RNA
<213> ORGANISM: Homo sapiens

<400> SEQUENCE: 395 agugggggaac ccuuccauga gg                                            22

<210> SEQ ID NO 396
<211> LENGTH: 22
<212> TYPE: RNA
<213> ORGANISM: Homo sapiens

<400> SEQUENCE: 396
acaguagucu gcacauuggu ua                                             22

<210> SEQ ID NO 397
<211> LENGTH: 22
<212> TYPE: RNA
<213> ORGANISM: Homo sapiens

<400> SEQUENCE: 397
acaguagucu gcacauuggu ua                                             22

<210> SEQ ID NO 398
<211> LENGTH: 23
<212> TYPE: RNA
```

```
<213> ORGANISM: Homo sapiens

<400> SEQUENCE: 398
cccaguguuc agacuaccug uuc                                        23

<210> SEQ ID NO 399
<211> LENGTH: 23
<212> TYPE: RNA
<213> ORGANISM: Homo sapiens

<400> SEQUENCE: 399
cccaguguuc agacuaccug uuc                                        23

<210> SEQ ID NO 400
<211> LENGTH: 21
<212> TYPE: RNA
<213> ORGANISM: Homo sapiens

<400> SEQUENCE: 400
auuugugcuu ggcucuguca c                                          21

<210> SEQ ID NO 401
<211> LENGTH: 23
<212> TYPE: RNA
<213> ORGANISM: Homo sapiens

<400> SEQUENCE: 401
aaagugcugc gacauuugag cgu                                        23

<210> SEQ ID NO 402
<211> LENGTH: 23
<212> TYPE: RNA
<213> ORGANISM: Homo sapiens

<400> SEQUENCE: 402
gaagugcuuc gauuuugggg ugu                                        23

<210> SEQ ID NO 403
<211> LENGTH: 22
<212> TYPE: RNA
<213> ORGANISM: Homo sapiens

<400> SEQUENCE: 403
ucuucucugu uuuggccaug ug                                         22

<210> SEQ ID NO 404
<211> LENGTH: 22
<212> TYPE: RNA
<213> ORGANISM: Homo sapiens

<400> SEQUENCE: 404
uggguggucu ggagauuugu gc                                         22

<210> SEQ ID NO 405
<211> LENGTH: 23
<212> TYPE: RNA
<213> ORGANISM: Homo sapiens

<400> SEQUENCE: 405
uaaggugcau cuagugcaga uag                                        23

<210> SEQ ID NO 406
<211> LENGTH: 23
```

<212> TYPE: RNA
<213> ORGANISM: Homo sapiens

<400> SEQUENCE: 406
gagggucuug ggagggaugu gac                                    23

<210> SEQ ID NO 407
<211> LENGTH: 21
<212> TYPE: RNA
<213> ORGANISM: Homo sapiens

<400> SEQUENCE: 407
agaggauacc cuuuguaugu u                                      21

<210> SEQ ID NO 408
<211> LENGTH: 20
<212> TYPE: RNA
<213> ORGANISM: Homo sapiens

<400> SEQUENCE: 408
uaaagagccc uguggagaca                                        20

<210> SEQ ID NO 409
<211> LENGTH: 22
<212> TYPE: RNA
<213> ORGANISM: Homo sapiens

<400> SEQUENCE: 409
aacuggcccu caaagucccg cu                                     22

<210> SEQ ID NO 410
<211> LENGTH: 20
<212> TYPE: RNA
<213> ORGANISM: Homo sapiens

<400> SEQUENCE: 410
cuuccucguc ugucugcccc                                        20

<210> SEQ ID NO 411
<211> LENGTH: 21
<212> TYPE: RNA
<213> ORGANISM: Homo sapiens

<400> SEQUENCE: 411
uuaauaucgg acaaccauug u                                      21

<210> SEQ ID NO 412
<211> LENGTH: 22
<212> TYPE: RNA
<213> ORGANISM: Homo sapiens

<400> SEQUENCE: 412
gccugcuggg guggaaccug gu                                     22

<210> SEQ ID NO 413
<211> LENGTH: 22
<212> TYPE: RNA
<213> ORGANISM: Homo sapiens

<400> SEQUENCE: 413
caaaaaccac aguuucuuuu gc                                     22

<210> SEQ ID NO 414

```
<211> LENGTH: 80
<212> TYPE: RNA
<213> ORGANISM: Homo sapiens

<400> SEQUENCE: 414
ccucugugag aaagggugug ggggagaggc ugucuugugu cuguaaguau gccaaacuua      60
uuuuccccaa ggcagaggga                                                 80

<210> SEQ ID NO 415
<211> LENGTH: 79
<212> TYPE: RNA
<213> ORGANISM: Homo sapiens

<400> SEQUENCE: 415
ccuuaauccu ugcaacgaac cugagccacu gauucaguaa aauacucagu ggcacauguu     60
uguugugagg gucaaaaga                                                  79

<210> SEQ ID NO 416
<211> LENGTH: 84
<212> TYPE: RNA
<213> ORGANISM: Homo sapiens

<400> SEQUENCE: 416
gugguacuug aagauagguu auccguguug ccuucgcuuu auuugugacg aaucauacac     60
gguugaccua uuuuucagua ccaa                                            84

<210> SEQ ID NO 417
<211> LENGTH: 83
<212> TYPE: RNA
<213> ORGANISM: Homo sapiens

<400> SEQUENCE: 417
ccugcugcag aggugccagc ugcaguggggg gaggcacugc cagggcugcc cacucugcuu    60
agccagcagg ugccaagaac agg                                             83

<210> SEQ ID NO 418
<211> LENGTH: 95
<212> TYPE: RNA
<213> ORGANISM: Homo sapiens

<400> SEQUENCE: 418
gucgaggccg uggcccggaa guggucgggg ccgcugcggg cggaagggcg ccugugcuuc     60
guccgcucgg cgguggccca gccaggcccg cggga                                95

<210> SEQ ID NO 419
<211> LENGTH: 91
<212> TYPE: RNA
<213> ORGANISM: Homo sapiens

<400> SEQUENCE: 419
ggcgggggcg cgggcggcag uggcgggagc ggccccucgg ccauccuccg ucugcccagu     60
uaccgcuucc gcuaccgccg ccgcucccgc u                                    91

<210> SEQ ID NO 420
<211> LENGTH: 65
<212> TYPE: RNA
<213> ORGANISM: Homo sapiens

<400> SEQUENCE: 420
aaaaggcgag acauugccag ggaguuuauu uuguagcucu cuugauaaaa uguuuuagca     60
```

```
aacac                                                               65

<210> SEQ ID NO 421
<211> LENGTH: 90
<212> TYPE: RNA
<213> ORGANISM: Homo sapiens

<400> SEQUENCE: 421
cucacagcug ccagugucau uuuugugauc ugcagcuagu auucucacuc caguugcaua    60
gucacaaaag ugaucauugg cagguguggc                                    90

<210> SEQ ID NO 422
<211> LENGTH: 87
<212> TYPE: RNA
<213> ORGANISM: Homo sapiens

<400> SEQUENCE: 422
agcgguggcc agugucauuu uugugauguu gcagcuagua auaugagccc aguugcauag    60
ucacaaaagu gaucauugga aacugug                                       87

<210> SEQ ID NO 423
<211> LENGTH: 67
<212> TYPE: RNA
<213> ORGANISM: Homo sapiens

<400> SEQUENCE: 423
auggaggugg agagucauca gcagcacuga gcaggcagug uugucugcug aguuccacg    60 ucauuug                                                             67

<210> SEQ ID NO 424
<211> LENGTH: 79
<212> TYPE: RNA
<213> ORGANISM: Homo sapiens

<400> SEQUENCE: 424
ugguacucgg ggagagguua cccgagcaac uuugcaucug gacgacgaau guugcucggu    60
gaaccccuuu ucgguauca                                                79

<210> SEQ ID NO 425
<211> LENGTH: 88
<212> TYPE: RNA
<213> ORGANISM: Homo sapiens

<400> SEQUENCE: 425
cgaggauggg agcugagggc uggucuuug cgggcgagau gagggugucg gaucaacugg    60
ccuacaaagu cccaguucuc ggccccg                                       88

<210> SEQ ID NO 426
<211> LENGTH: 94
<212> TYPE: RNA
<213> ORGANISM: Homo sapiens

<400> SEQUENCE: 426
aucacagaca ccuccaagug ugcagggcac uggugggggc cggggcaggc ccagcgaaag    60
ugcaggaccu ggcacuuagu cggaagugag ggug                                94

<210> SEQ ID NO 427
<211> LENGTH: 87
<212> TYPE: RNA
```

```
<213> ORGANISM: Homo sapiens

<400> SEQUENCE: 427
accgcaggga aaaugaggga cuuuuggggg cagaugugnu uccauccac uaucauaaug    60 ccccuaaaaa uccuuauugc ucuugca                                      87

<210> SEQ ID NO 428
<211> LENGTH: 84
<212> TYPE: RNA
<213> ORGANISM: Homo sapiens

<400> SEQUENCE: 428 gcuccccuc ucuaauccuu gcuaccuggg ugagagugcu gucugaaugc aaugcaccug    60
ggcaaggauu cugagagcga gagc                                         84

<210> SEQ ID NO 429
<211> LENGTH: 84
<212> TYPE: RNA
<213> ORGANISM: Homo sapiens

<400> SEQUENCE: 429
uugacuuagc ugguaguguu ggaacccuuc caugaggagu agaacacucc uuaugcaaga   60
uucccuucua ccuggcuggg uugg                                         84

<210> SEQ ID NO 430
<211> LENGTH: 71
<212> TYPE: RNA
<213> ORGANISM: Homo sapiens

<400> SEQUENCE: 430
gccaacccag uguucagacu accuguucag gaggcucuca auguguacag uagucugcac   60
auugguuagg c                                                       71

<210> SEQ ID NO 431
<211> LENGTH: 110
<212> TYPE: RNA
<213> ORGANISM: Homo sapiens

<400> SEQUENCE: 431
aggaagcuuc uggagauccu gcuccgucgc cccaguguuc agacuaccug uucaggacaa   60
ugccguugua caguagucug cacauugguu agacugggca agggagagca              110

<210> SEQ ID NO 432
<211> LENGTH: 71
<212> TYPE: RNA
<213> ORGANISM: Homo sapiens

<400> SEQUENCE: 432
gccaacccag uguucagacu accuguucag gaggcucuca auguguacag uagucugcac   60
auugguuagg c                                                       71

<210> SEQ ID NO 433
<211> LENGTH: 110
<212> TYPE: RNA
<213> ORGANISM: Homo sapiens

<400> SEQUENCE: 433
aggaagcuuc uggagauccu gcuccgucgc cccaguguuc agacuaccug uucaggacaa   60
ugccguugua caguagucug cacauugguu agacugggca agggagagca              110
```

<210> SEQ ID NO 434
<211> LENGTH: 91
<212> TYPE: RNA
<213> ORGANISM: Homo sapiens

<400> SEQUENCE: 434
uuuucaaagc aaugugugac agguacaggg acaaaucccg uuaauaagua agaggauuug    60
ugcuuggcuc ugucacaugc cacuuugaaa a                                  91

<210> SEQ ID NO 435
<211> LENGTH: 67
<212> TYPE: RNA
<213> ORGANISM: Homo sapiens

<400> SEQUENCE: 435
gugggccuca aauguggagc acuauucuga uguccaagug gaaagucug cgacauuuga    60 gcgucac                                                             67

<210> SEQ ID NO 436
<211> LENGTH: 69
<212> TYPE: RNA
<213> ORGANISM: Homo sapiens

<400> SEQUENCE: 436
gggauacuca aaauggggc gcuuccuuu uugucuguac ugggaagugc uucgauuug      60 ggugucccc                                                           69

<210> SEQ ID NO 437
<211> LENGTH: 86
<212> TYPE: RNA
<213> ORGANISM: Homo sapiens

<400> SEQUENCE: 437
auuaggagag uaucuucucu guuuuggcca ugugguacu cacagccccu cacacauggc    60
cgaaacagag aaguuacuuu ccuaau                                        86

<210> SEQ ID NO 438
<211> LENGTH: 71
<212> TYPE: RNA
<213> ORGANISM: Homo sapiens

<400> SEQUENCE: 438
agguuguucu ggguggucug gagauuugug cagcuuguac cugcacaaau cuccggacca   60
cuuagucuuu a                                                        71

<210> SEQ ID NO 439
<211> LENGTH: 71
<212> TYPE: RNA
<213> ORGANISM: Homo sapiens

<400> SEQUENCE: 439
uguucuaagg ugcaucuagu gcagauagug aaguagauua gcaucuacug cccuaagugc   60
uccuucuggc a                                                        71

<210> SEQ ID NO 440
<211> LENGTH: 97
<212> TYPE: RNA
<213> ORGANISM: Homo sapiens -continued

<400> SEQUENCE: 440
gggacuuguc acugccuguc uccucccucu ccagcagcga cuggauucug gaguccaucu    60
agagggucuu gggagggaug ugacuguugg aagccc                              97

<210> SEQ ID NO 441
<211> LENGTH: 86
<212> TYPE: RNA
<213> ORGANISM: Homo sapiens

<400> SEQUENCE: 441
uuugguacuu gaagagagga uacccuuugu auguucacuu gauuaauggc gaauauacag    60
ggggagacuc uuauuugcgu aucaaa                                         86

<210> SEQ ID NO 442
<211> LENGTH: 86
<212> TYPE: RNA
<213> ORGANISM: Homo sapiens

<400> SEQUENCE: 442
uuugguacuu aaagagagga uacccuuugu auguucacuu gauuaauggc gaauauacag    60
ggggagacuc ucauuugcgu aucaaa                                         86

<210> SEQ ID NO 443
<211> LENGTH: 83
<212> TYPE: RNA
<213> ORGANISM: Homo sapiens

<400> SEQUENCE: 443
ccccagcuag guaaagagcc cuguggagac accuggauuc agagaacaug ucuccacuga    60
gcacuugggc cuugauggcg gcu                                            83

<210> SEQ ID NO 444
<211> LENGTH: 83
<212> TYPE: RNA
<213> ORGANISM: Homo sapiens

<400> SEQUENCE: 444
guggucucag aaucgggguu uugagggcga gaugaguuua uguuuauccc aacuggcccu    60
caaagucccg cuuuuggggu cau                                            83

<210> SEQ ID NO 445
<211> LENGTH: 83
<212> TYPE: RNA
<213> ORGANISM: Homo sapiens

<400> SEQUENCE: 445
gugaguggga gccccagugu guggguuggg ccauggcggg ugggcagccc agccucugag    60
ccuuccucgu cugucugccc cag                                            83

<210> SEQ ID NO 446
<211> LENGTH: 79
<212> TYPE: RNA
<213> ORGANISM: Homo sapiens

<400> SEQUENCE: 446
gugcuuaaag aauggcuguc cguaguaugg ucucuauauu uaugaugauu aauaucggac    60
aaccauuguu uuaguaucc                                                 79

```
<210> SEQ ID NO 447
<211> LENGTH: 75
<212> TYPE: RNA
<213> ORGANISM: Homo sapiens

<400> SEQUENCE: 447
agacagagaa gccaggucac gucucugcag uuacacagcu cacgagugcc ugcuggggug      60
gaaccugguc ugucu                                                      75

<210> SEQ ID NO 448
<211> LENGTH: 97
<212> TYPE: RNA
<213> ORGANISM: Homo sapiens

<400> SEQUENCE: 448
aaacaaguua uauuagguug gugcaaaagu aauugugguu uuugccugua aaaguaaugg      60
caaaaaccac aguucuuuu gcaccagacu aauaaag                               97

<210> SEQ ID NO 449
<211> LENGTH: 23
<212> TYPE: RNA
<213> ORGANISM: Homo sapiens

<400> SEQUENCE: 449
caaagugcuc auagugcagg uag                                             23

<210> SEQ ID NO 450
<211> LENGTH: 23
<212> TYPE: RNA
<213> ORGANISM: Homo sapiens

<400> SEQUENCE: 450
uaaggugcau cuagugcaga uag                                             23

<210> SEQ ID NO 451
<211> LENGTH: 23
<212> TYPE: RNA
<213> ORGANISM: Homo sapiens

<400> SEQUENCE: 451
caaagugcuu acagugcagg uag                                             23

<210> SEQ ID NO 452
<211> LENGTH: 22
<212> TYPE: RNA
<213> ORGANISM: Homo sapiens

<400> SEQUENCE: 452
uaacacuguc ugguaaagau gg                                              22

<210> SEQ ID NO 453
<211> LENGTH: 22
<212> TYPE: RNA
<213> ORGANISM: Homo sapiens

<400> SEQUENCE: 453
acuuuaacau ggaagugcuu uc                                              22

<210> SEQ ID NO 454
<211> LENGTH: 21
<212> TYPE: RNA
<213> ORGANISM: Homo sapiens
```

<400> SEQUENCE: 454
uacaguacug ugauaacuga a                                              21

<210> SEQ ID NO 455
<211> LENGTH: 21
<212> TYPE: RNA
<213> ORGANISM: Homo sapiens

<400> SEQUENCE: 455
cauuauuacu uuugguacgc g                                              21

<210> SEQ ID NO 456
<211> LENGTH: 22
<212> TYPE: RNA
<213> ORGANISM: Homo sapiens

<400> SEQUENCE: 456
ugagaacuga auccauggg uu                                              22

<210> SEQ ID NO 457
<211> LENGTH: 22
<212> TYPE: RNA
<213> ORGANISM: Homo sapiens

<400> SEQUENCE: 457
ugagaacuga auccauagg cu                                              22

<210> SEQ ID NO 458
<211> LENGTH: 22
<212> TYPE: RNA
<213> ORGANISM: Homo sapiens

<400> SEQUENCE: 458
uucaaguaau ccaggauagg cu                                             22

<210> SEQ ID NO 459
<211> LENGTH: 22
<212> TYPE: RNA
<213> ORGANISM: Homo sapiens

<400> SEQUENCE: 459
uagcaccauc ugaaaucggu ua                                             22

<210> SEQ ID NO 460
<211> LENGTH: 22
<212> TYPE: RNA
<213> ORGANISM: Homo sapiens

<400> SEQUENCE: 460
uaacagucua cagccauggu cg                                             22

<210> SEQ ID NO 461
<211> LENGTH: 23
<212> TYPE: RNA
<213> ORGANISM: Homo sapiens

<400> SEQUENCE: 461
ucuuugguua ucuagcugua uga                                            23

<210> SEQ ID NO 462
<211> LENGTH: 22
<212> TYPE: RNA
<213> ORGANISM: Homo sapiens -continued

```
<400> SEQUENCE: 462
ugagaacuga auccaugggg uu                                        22

<210> SEQ ID NO 463
<211> LENGTH: 23
<212> TYPE: RNA
<213> ORGANISM: Homo sapiens

<400> SEQUENCE: 463
uacccuguag aaccgaauuu gug                                       23

<210> SEQ ID NO 464
<211> LENGTH: 21
<212> TYPE: RNA
<213> ORGANISM: Homo sapiens

<400> SEQUENCE: 464
agcuacaucu ggcuacuggg u                                         21

<210> SEQ ID NO 465
<211> LENGTH: 22
<212> TYPE: RNA
<213> ORGANISM: Homo sapiens

<400> SEQUENCE: 465
aacuggcccu caaagucccg cu                                        22

<210> SEQ ID NO 466
<211> LENGTH: 23
<212> TYPE: RNA
<213> ORGANISM: Homo sapiens

<400> SEQUENCE: 466
agcuacauug ucugcugggu uuc                                       23

<210> SEQ ID NO 467
<211> LENGTH: 23
<212> TYPE: RNA
<213> ORGANISM: Homo sapiens

<400> SEQUENCE: 467
uauggcuuuu uauuccuaug uga                                       23

<210> SEQ ID NO 468
<211> LENGTH: 23
<212> TYPE: RNA
<213> ORGANISM: Homo sapiens

<400> SEQUENCE: 468
ucuggcuccg ugucuucacu ccc                                       23

<210> SEQ ID NO 469
<211> LENGTH: 23
<212> TYPE: RNA
<213> ORGANISM: Homo sapiens

<400> SEQUENCE: 469
cccaguguuc agacuaccug uuc                                       23

<210> SEQ ID NO 470
<211> LENGTH: 23
<212> TYPE: RNA
```

<213> ORGANISM: Homo sapiens

<400> SEQUENCE: 470
acuuaaacgu ggauguacuu gcu                                   23

<210> SEQ ID NO 471
<211> LENGTH: 22
<212> TYPE: RNA
<213> ORGANISM: Homo sapiens

<400> SEQUENCE: 471
uuuaacaugg ggguaccugc ug                                    22

<210> SEQ ID NO 472
<211> LENGTH: 23
<212> TYPE: RNA
<213> ORGANISM: Homo sapiens

<400> SEQUENCE: 472
uaagugcuuc cauguuugag ugu                                   23

<210> SEQ ID NO 473
<211> LENGTH: 21
<212> TYPE: RNA
<213> ORGANISM: Homo sapiens

<400> SEQUENCE: 473
aauaauacau gguugaucuu u                                     21

<210> SEQ ID NO 474
<211> LENGTH: 22
<212> TYPE: RNA
<213> ORGANISM: Homo sapiens

<400> SEQUENCE: 474
gccugcuggg guggaaccug gu                                    22

<210> SEQ ID NO 475
<211> LENGTH: 22
<212> TYPE: RNA
<213> ORGANISM: Homo sapiens

<400> SEQUENCE: 475
ugagguagua gguuguauag uu                                    22

<210> SEQ ID NO 476
<211> LENGTH: 22
<212> TYPE: RNA
<213> ORGANISM: Homo sapiens

<400> SEQUENCE: 476
ugagguagua gguugugugg uu                                    22

<210> SEQ ID NO 477
<211> LENGTH: 23
<212> TYPE: RNA
<213> ORGANISM: Homo sapiens

<400> SEQUENCE: 477
uacccuguag aaccgaauuu gug                                   23

<210> SEQ ID NO 478
<211> LENGTH: 21

```
<212> TYPE: RNA
<213> ORGANISM: Homo sapiens

<400> SEQUENCE: 478
aucacauugc cagggauuuc c                                              21

<210> SEQ ID NO 479
<211> LENGTH: 21
<212> TYPE: RNA
<213> ORGANISM: Homo sapiens

<400> SEQUENCE: 479
aucacauugc cagggauuac c                                              21

<210> SEQ ID NO 480
<211> LENGTH: 22
<212> TYPE: RNA
<213> ORGANISM: Homo sapiens

<400> SEQUENCE: 480
uauugcacau uacuaaguug ca                                             22
```